(12) United States Patent
Ueki et al.

(10) Patent No.: US 9,872,919 B2
(45) Date of Patent: Jan. 23, 2018

(54) PRODRUGS FOR SELECTIVE ANTICANCER THERAPY

(71) Applicants: Nobuhide Ueki, Forest Hills, NY (US); Michael J. Hayman, Patchogue, NY (US)

(72) Inventors: Nobuhide Ueki, Forest Hills, NY (US); Michael J. Hayman, Patchogue, NY (US)

(73) Assignee: THE RESEARCH FOUNDATION FOR THE STATE UNIVERSITY OF NEW YORK, Albany, NY (US)

( * ) Notice: Subject to any disclaimer, the term of this patent is extended or adjusted under 35 U.S.C. 154(b) by 0 days.

(21) Appl. No.: 14/428,501

(22) PCT Filed: Sep. 18, 2013

(86) PCT No.: PCT/US2013/060443
§ 371 (c)(1),
(2) Date: Mar. 16, 2015

(87) PCT Pub. No.: WO2014/047199
PCT Pub. Date: Mar. 27, 2014

(65) Prior Publication Data
US 2015/0224208 A1 Aug. 13, 2015

Related U.S. Application Data

(60) Provisional application No. 61/864,123, filed on Aug. 9, 2013, provisional application No. 61/702,882, filed on Sep. 19, 2012.

(51) Int. Cl.
| | | |
|---|---|---|
| *A61K 47/54* | (2017.01) | |
| *A61K 47/48* | (2006.01) | |
| *C07H 19/06* | (2006.01) | |
| *C07H 19/16* | (2006.01) | |
| *C07K 5/11* | (2006.01) | |
| *C07K 5/09* | (2006.01) | |
| *C07K 5/068* | (2006.01) | |
| *C07H 19/067* | (2006.01) | |
| *C07H 19/073* | (2006.01) | |
| *C07H 19/09* | (2006.01) | |

(Continued)

(52) U.S. Cl.
CPC .... *A61K 47/48246* (2013.01); *A61K 31/7068* (2013.01); *A61K 31/7076* (2013.01); *A61K 47/54* (2017.08); *A61K 47/542* (2017.08); *A61K 47/64* (2017.08); *C07H 19/06* (2013.01); *C07H 19/067* (2013.01); *C07H 19/073* (2013.01); *C07H 19/09* (2013.01); *C07H 19/16* (2013.01); *C07K 5/0215* (2013.01); *C07K 5/06008* (2013.01); *C07K 5/06086* (2013.01); *C07K 5/0817* (2013.01); *C07K 5/1019* (2013.01)

(58) Field of Classification Search
None
See application file for complete search history.

(56) References Cited

U.S. PATENT DOCUMENTS 6,369,030 B1 * 4/2002 Cole ................... C07K 7/06
530/324
7,115,635 B2 * 10/2006 Kiuchi ................ A61K 31/454
514/217.04

(Continued)

FOREIGN PATENT DOCUMENTS

| WO | WO 1981/001145 A1 | 4/1981 |
|---|---|---|
| WO | WO 2007/022535 A2 | 2/2007 |

(Continued)

OTHER PUBLICATIONS

Office Action dated May 31, 2017 in connection with U.S. Appl. No. 14/911,187.

(Continued)

*Primary Examiner* — Thomas S Heard
(74) *Attorney, Agent, or Firm* — Gary J. Gershik; Cooper & Dunham LLP

(57) ABSTRACT

The present invention provides a compound having the structure:

$$X \overset{O}{\underset{R_1}{\overset{\alpha}{\diagup}}} (\phantom{x})_n \overset{H}{\underset{}{N}} \overset{O}{\diagdown} Z$$

wherein
X is a therapeutic agent containing at least one amine nitrogen and the amine nitrogen on the therapeutic agent covalently bonds directly to carbon α;
Z is $CH_3$ or $CF_3$;
$R_1$ is —H, —$NR_2R_3$, —NH—C(=O)—$R_4$, —NH—C (=O)—$OR_4$, —$CH_2$—C(=O)—$NR_5R_6$, —$OR_7$, —$CO_2R_7$, $C_{1-6}$ alkyl, $C_{2-6}$ alkenyl, $C_{2-6}$ alkynyl, aryl, or heteroaryl,
wherein $R_2$, $R_3$, $R_4$, $R_5$, $R_6$ and $R_7$ are each, independently, —H, $C_{1-6}$ alkyl, $C_{2-6}$ alkenyl, $C_{2-6}$ alkynyl, heteroalkyl, cycloalkyl, heterocyclyl, aryl, alkylaryl, heteroaryl, alkylheteroaryl, an amino acid or an oligopeptide;
wherein an amine of the amino acid or oligopeptide is substituted or unsubstituted; and
n is an integer from 0 to 6;
or a diastereomer, enantiomer or pharmaceutically acceptable salt of the compound.

16 Claims, 32 Drawing Sheets

(51) Int. Cl.
    A61K 31/7068    (2006.01)
    A61K 31/7076    (2006.01)
    C07K 5/02       (2006.01)
    C07K 5/06       (2006.01)
    A61K 47/64      (2017.01)

(56) References Cited

U.S. PATENT DOCUMENTS

| 2010/0047333 | A1* | 2/2010 | Muller | A61K 38/02 |
| | | | | 424/450 |
| 2010/0062465 | A1 | 3/2010 | Ronen et al. | |
| 2013/0122535 | A1 | 5/2013 | Salic et al. | |
| 2016/0184459 | A1 | 6/2016 | Ueki et al. | |

FOREIGN PATENT DOCUMENTS

| WO | WO 2007/124435 A2 | 11/2007 |
| WO | WO 2014/021305 A1 | 2/2008 |
| WO | WO 2012/149540 A1 | 11/2012 |
| WO | WO 2014/047199 A1 | 3/2014 |
| WO | WO 2015/021305 A1 | 2/2015 |

OTHER PUBLICATIONS

International Preliminary Report on Patentability dated Feb. 9, 2016 in connection with PCT International Application PCT/US2014/050190.

International Search Report dated Feb. 13, 2014 in connection with PCT International Application No. PCT/US2013/060443.

International Search Report dated Nov. 27, 2014 in connection with PCT International Application No. PCT/US2014/050190.

Written Opinion of the International Searching Authority dated Feb. 14, 2014 in connection with PCT International Application No. PCT/US2013/060443.

International Preliminary Report on Patentability dated Mar. 24, 2015 in connection with PCT International Application PCT/US2013/060443.

Written Opinion of the International Searching Authority dated Nov. 27, 2014 connection with PCT International Application No. PCT/US2014/050190.

Caravan, P. et al. (2009) A lysine walk to high relaxivity collagen-targeted MRI contrast agents. *Chem. Commun.* 430-432.

Eigner, S. et al. (2013) Imaging of Protein Synthesis: In Vitro and In Vivo Evaluation of $^{44}$Sc-DOTA-Puromycin. *Mol. Imaging Biol.* 15, 79-86.

Hirsch, B. M. et al. (2011) Potent sirtuin inhibition bestowed by L-2-amino-7-carboxamidoheptanoic acid (L-ACAH), a $N^\tau$-acetyl-lysine analog. *Med. Chem. Commun.* 2, 291.

Wegener, D. et al. (2003) A Fluorogenic Histone Deacetylase Assay Well Suited for High-Throughput Activity Screening. *Chemistry & Biology*. vol. 10, 61-68.

Wegener, D. et al. (2003). A fluorogenic histone deacetylase assay well suited for high-throughput activity screening. *Chemistry & Biology*, 10, 61-68.

Hirsch, B. M. et al. (2011). Potent sirtuin inhibition bestowed by L-2-amino-7-carboxamidoheptanoic acid (L-ACAH), a $N^\epsilon$-acetyl-lysine analog. *Medicinal Chemistry Communications*, 2, 291-299.

Notification of Transmittal of the International Search Report and the Written Opinion of the International Searching Authority, or the Declaration, including an International Search Report and Written Opinion of the International Searching Authority, dated Feb. 13, 2014 in connection with PCT International Application No. PCT/US2013/060443, filed Sep. 18, 2013.

* cited by examiner

Tumor incidence

| Groups | Tumor > 300mm³ |
|---|---|
| DMSO | 5/6 |
| 67 mg/kg | 1/3 |
| 200 mg/kg | 0/4 |

5-fluorocytidine      Gemcitabine      Cytarabine

Figure 29A-B
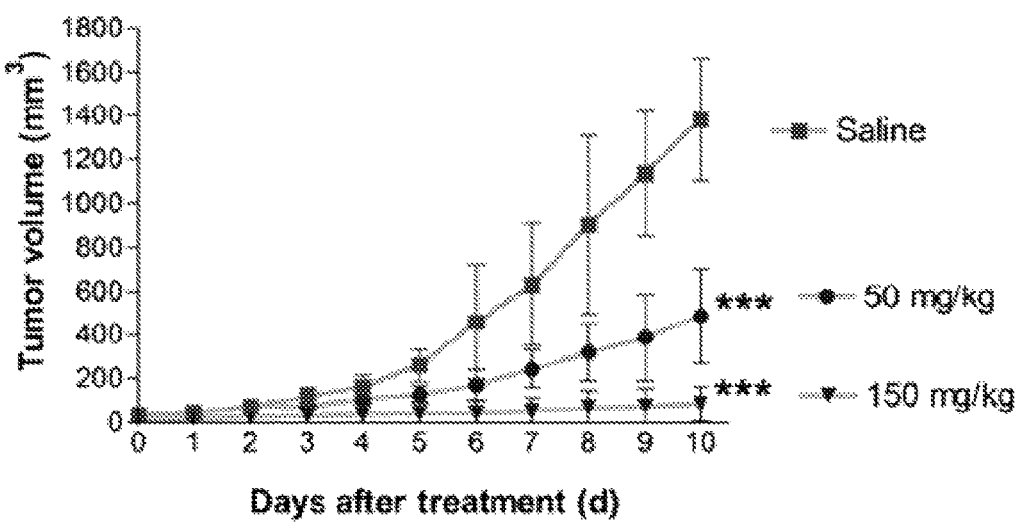
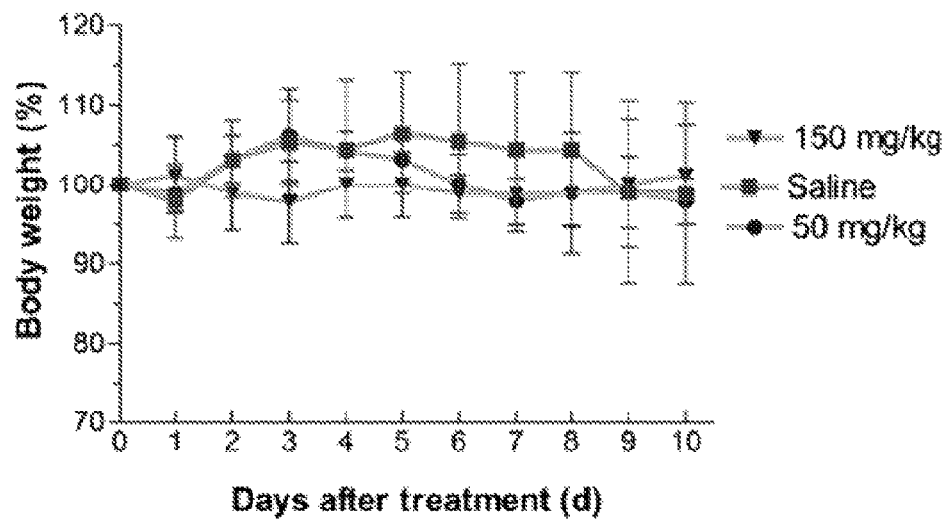

Figure 29C-D
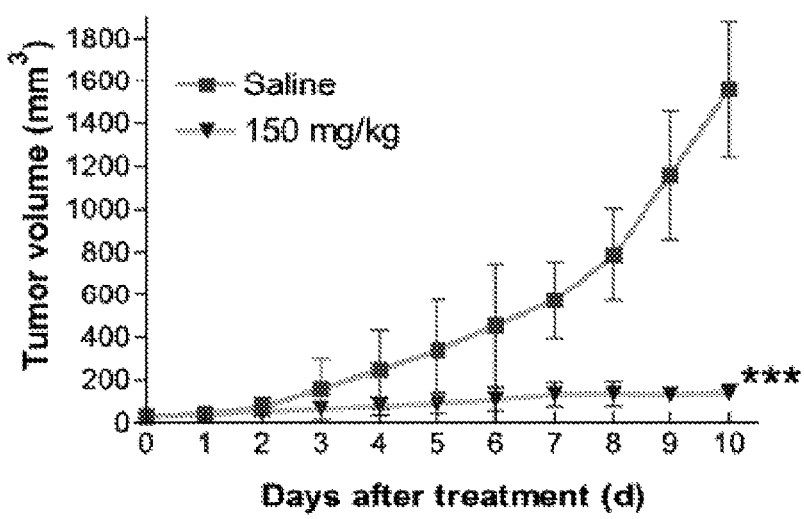
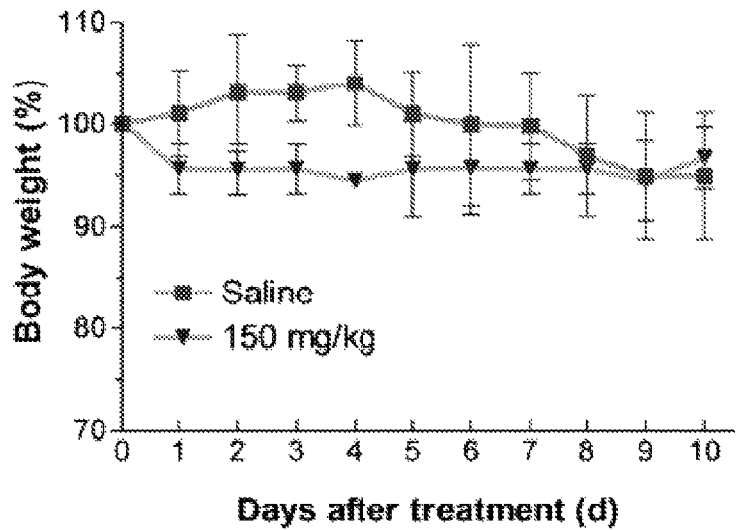

PRODRUGS FOR SELECTIVE ANTICANCER THERAPY

CROSS-REFERENCE TO RELATED APPLICATIONS

This application is a §371 national stage of PCT International Application No. PCT/US2013/060443, filed Sep. 18, 2013, claiming the benefit of U.S. Provisional Applications Nos. 61/864,123, filed Aug. 9, 2013, and 61/702,882, filed Sep. 19, 2012, the contents of each of which are hereby incorporated by reference in their entirety.

This invention was made with government support under grant number CA009176 awarded by the National Institutes of Health. The government has certain rights in the invention Throughout this application, certain publications are referenced in parentheses. Full citations for these publications may be found immediately preceding the claims. The disclosures of these publications in their entireties are hereby incorporated by reference into this application in order to describe more fully the state of the art to which this invention relates.

BACKGROUND OF THE INVENTION

There is a growing interest in developing therapeutic agents with increased selectivity. The ability of a therapeutic agent to affect a particular population of cells in preference over others is a highly desirable property. A therapeutic agent or drug having low selectivity leads to reduced efficacy and higher toxicity. For example, a major limitation of many cancers treatments is their low selectivity for tumor cells. Radiation therapy and alkylating agents perturb many functions that are common to both tumor and normal cells.

HDACs are key enzymes involved in the epigenetic regulation of histone and non-histone proteins (Witt, O. et al. 2009). They modulate protein structure and function through deacetylation of lysine residues. In cancer biology, the involvement of HDACs has been well documented, supporting the notion that altered expression of HDACs could have an active role in tumor development (Haberland, M. et al. 2009; Bolden, J. E. et al. 2006). Consistent with this, the therapeutic potential of HDAC inhibitors (HDACi) is recognized as a new class of drug for cancer (Bolden, J. E. et al. 2006; Minucci, S. et al. 2006; Marks, P. A. & Xu, W. S. 2009). HDAC inhibitors (HDACi), which were developed as single target agents, are a new class of drugs for cancer (Minucci, S. & Pelicci, P. G. 2006; Bolden, J. E. et al. 2006; Marks, P. A. & Xu, W. S. 2009). Currently a number of HDACi are in clinical trials for various hematologic and solid tumors (Marks, P. A. & Xu, W. S. 2009; Wagner, J. M. et al. 20104). In preclinical studies, several HDACi have been found to have potent anticancer effects. However, adverse side effects have been reported in a number of preclinical trials (Bolden, J. E. et al. 2006; Wagner, J. M. et al. 2010). Therefore, selectivity remains a major challenge. Also, since certain HDACs are essential for normal cells, a single target agent using these pharmacologic inhibitors depends on the tolerance levels of normal cells to the damage caused by the treatment (Lee, J. H. et al. 2010; Bhaskara, S. et al. 2010).

Tumor-associated cysteine protease CTSL also plays crucial roles at multiple stages of tumor progression and metastasis (Joyce, J. A. et al. 2004; Jedeszko, C. et al. 2004; Gonzalez-Suarez, I. et al. 2011). Cell lines transformed by certain oncogenes including Ras are known to express high levels of CTSL (Collette, J. et al. 2004; Denhardt, D. T. et al. 1987; Joseph, L. J. et al. 1988). Thus, the upregulation of CTSL is recognized as a hallmark of metastatic cancers and could be utilized as a prognostic marker (Joyce, J. A. et al. 2004; Jedeszko, C. et al. 2004; Gonzalez-Suarez, I. et al. 2011; Tian, Y, et al. 2011; Grotsky, D. A. et al. 2013). Recently, nuclear-localized CTSL involved in cancer has been revealed, suggesting that CTSL may have key roles in the nucleus beyond its known lysosomal and extracellular activities (Gonzalez-Suarez, I. et al. 2011; Grotsky, D. A. et al. 2013; Goulet, B. et al. 2004; Goulet, B. et al. 2007). Although the therapeutic potential of CTSL inhibitors has not been fully characterized in preclinical studies, targeting CTSL activity is considered as a strategy for anticancer therapy (Lankelma, J. M. et al. 2010).

Therefore, drugs with improved selectivity are still urgently needed to combat cancer and various other diseases. Such selectivity allows for a drug with maximal efficacy and minimal adverse effects or toxicity.

SUMMARY OF THE INVENTION

The present invention provides a compound having the structure:

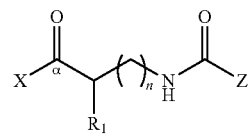

wherein
X is a therapeutic agent containing at least one amine nitrogen and the amine nitrogen on the therapeutic agent covalently bonds directly to carbon α;
Z is $CH_3$ or $CF_3$;
$R_1$ is —H, —$NR_2R_3$, —NH—C(=O)—$R_4$, —NH—C(=O)—$OR_4$, —$CH_2$—C(=O)—$NR_5R_6$, —$OR_7$, —$CO_2R_7$, $C_{1-6}$ alkyl, $C_{2-6}$ alkenyl, $C_{2-6}$ alkynyl, aryl, or heteroaryl,
  wherein $R_2$, $R_3$, $R_4$, $R_5$, $R_6$ and $R_7$ are each, independently, —H, $C_{1-6}$ alkyl, $C_{2-6}$ alkenyl, $C_{2-6}$ alkynyl, heteroalkyl, cycloalkyl, heterocyclyl, aryl, alkylaryl, heteroaryl, alkylheteroaryl, an amino acid or an oligopeptide;
    wherein an amine of the amino acid or oligopeptide is substituted or unsubstituted; and
n is an integer from 0 to 6;
or a diastereomer, enantiomer or pharmaceutically acceptable salt of the compound.

The present invention provides compound having the structure:

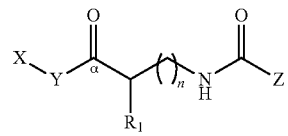

wherein
X is a therapeutic agent;
Y is a chemical linker;
  wherein Y is present or absent, and when present, Y is a chemical linker containing at least one amine nitrogen, wherein the amine nitrogen on the linker covalently bonds directly to carbon α, or Y is a para-aminobenzyl alcohol linker,
  wherein the nitrogen on the linker Y connects directly to carbon α and the oxygen on the linker Y connects to the therapeutic agent X, or the oxygen on the linker Y connects directly to carbon α and the nitrogen on the linker Y connects to the therapeutic agent X through an amide bond;

Z is $CH_3$ or $CF_3$;

$R_1$ is —H, —$NR_2R_3$, —NH—C(=O)—$R_4$, —NH—C(=O)—$OR_4$, —$CH_2$—C(=O)—$NR_5R_6$, —$OR_7$, —$CO_2R_7$, $C_{1-6}$ alkyl, $C_{2-6}$ alkenyl, $C_{2-6}$ alkynyl, aryl, or heteroaryl,
  wherein $R_2$, $R_3$, $R_4$, $R_5$, $R_6$ and $R_7$ are each, independently, —H, $C_{1-6}$ alkyl, $C_{2-6}$ alkenyl, $C_{2-6}$ alkynyl, heteroalkyl, cycloalkyl, heterocyclyl, aryl, alkylaryl, heteroaryl, alkylheteroaryl, an amino acid or an oligopeptide;
    wherein the amine of the amino acid or oligopeptide is substituted or unsubstituted; and n is an integer from 0 to 6;

or a diastereomer, enantiomer or pharmaceutically acceptable salt of the compound.

The invention provides a compound having the structure:

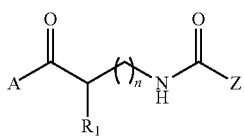

wherein
A is OH, O($C_1$-$C_6$ alkyl) or O($CH_2$-aryl);
Z is $CH_3$ or $CF_3$;
$R_1$ is —H, —$NR_2R_3$, —NH—C(=O)—$R_4$, —NH—C(=O)—$OR_4$, —$CH_2$—C(=O)—$NR_5R_6$, —$OR_7$, —$CO_2R_7$, $C_{1-6}$ alkyl, $C_{2-6}$ alkenyl, $C_{2-6}$ alkynyl, aryl, or heteroaryl,
  wherein $R_2$, $R_3$, $R_4$, $R_5$, $R_6$ and $R_7$ are each, independently, —H, $C_{1-6}$ alkyl, $C_{2-6}$ alkenyl, $C_{2-6}$ alkynyl, heteroalkyl, cycloalkyl, heterocyclyl, aryl, alkylaryl, heteroaryl, alkylheteroaryl, an amino acid or an oligopeptide;
    wherein an amine of the amino acid or oligopeptide is substituted or unsubstituted; and n is an integer from 0 to 6;

or a diastereomer, enantiomer or pharmaceutically acceptable salt of the compound.

BRIEF DESCRIPTION OF THE FIGURES

FIG. 21. HCT116 cells were implanted subcutaneously into female nude mice. When palpable tumors reached 50-150 mm$^3$, animals were randomized and treated by the indicated dose of the compound or vehicle control (DMSO) via intraperitoneal injection. Tumor incidence is presented as number of mice developed tumor (volume>300 mm$^3$) after 2 weeks of daily treatment/number of mice treated. Tumor volume was estimated by the equation vol=(a×b$^2$)/2, where vol, a, and b represent volume, the length of the major axis, and the length of the minor axis, respectively. In vivo anticancer efficacy of BKAc-Puro was demonstrated by the inhibition of tumor incidence in mouse xenograft model. Consistent with the data presented above, no toxicity was observed in the groups treated with the drug.

DETAILED DESCRIPTION OF THE INVENTION

Figure 1:
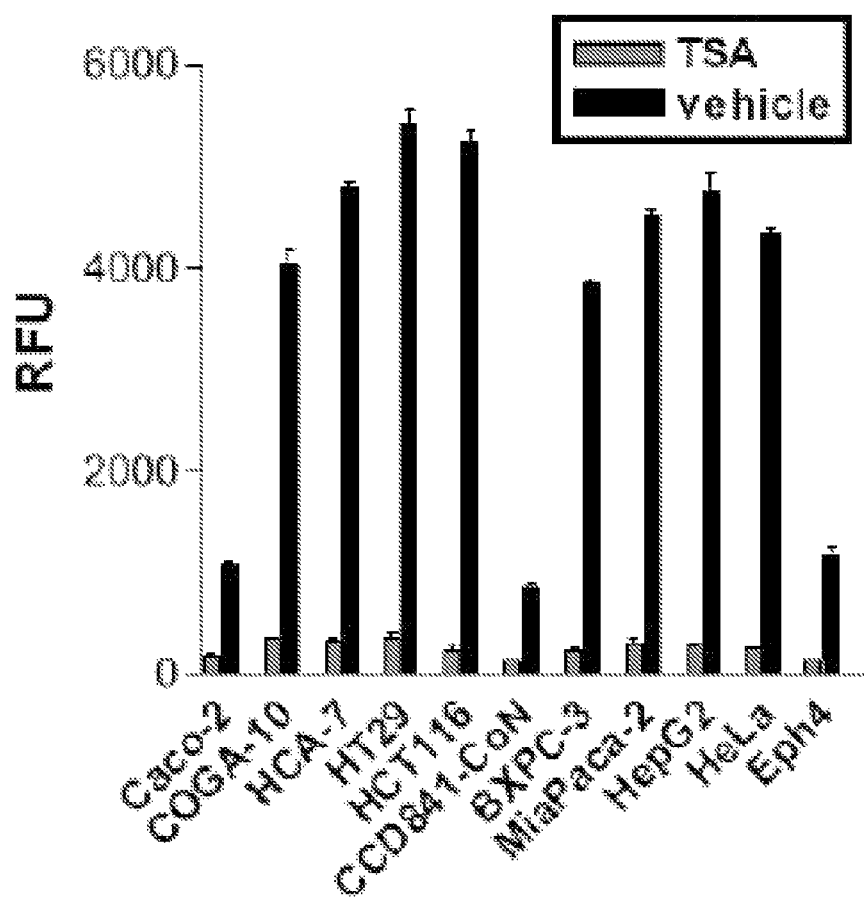
FIG. 1. Comparative HDAC activity of the panel of cancer and normal cell lines measured by a standard HDAC assay using substrate Boc-Lys(Ac)-AMC either with vehicle control DMSO or TSA (1 μM). Data represent mean values of triplicate measurements±s.d. RFU, relative fluorescent units.

The present invention provides a compound having the structure:

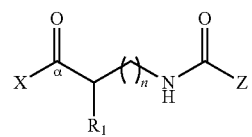

wherein
X is a therapeutic agent containing at least one amine nitrogen and the amine nitrogen on the therapeutic agent covalently bonds directly to carbon α;
Z is $CH_3$ or $CF_3$;
$R_1$ is —H, —$NR_2R_3$, —NH—C(=O)—$R_4$, —NH—C(=O)—$OR_4$, —$CH_2$—C(=O)—$NR_5R_6$, —$OR_7$, —$CO_2R_7$, $C_{1-6}$ alkyl, $C_{2-6}$ alkenyl, $C_{2-6}$ alkynyl, aryl, or heteroaryl,
wherein $R_2$, $R_3$, $R_4$, $R_5$, $R_6$ and $R_7$ are each, independently, —H, $C_{1-6}$ alkyl, $C_{2-6}$ alkenyl, $C_{2-6}$ alkynyl, heteroalkyl, cycloalkyl, heterocyclyl, aryl, alkylaryl, heteroaryl, alkylheteroaryl, an amino acid or an oligopeptide;
wherein an amine of the amino acid or oligopeptide is substituted or unsubstituted; and
n is an integer from 0 to 6;
or a diastereomer, enantiomer or pharmaceutically acceptable salt of the compound.

In some embodiments, the compound having the structure:

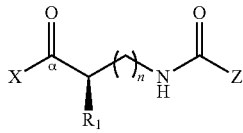

wherein
X is a therapeutic agent containing at least one amine nitrogen and the amine nitrogen on the therapeutic agent covalently bonds directly to carbon α;
Z is $CH_3$ or $CF_3$;
$R_1$ is —H, —$NR_2R_3$, —NH—C(=O)—$R_4$, —NH—C(=O)—$OR_4$, —$CH_2$—C(=O)—$NR_5R_6$, —$OR_7$, —$CO_2R_7$, $C_{1-6}$ alkyl, $C_{2-6}$ alkenyl, $C_{2-6}$ alkynyl, aryl, or heteroaryl,
wherein $R_2$, $R_3$, $R_4$, $R_5$, $R_6$ and $R_7$ are each, independently, —H, $C_{1-6}$ alkyl, $C_{2-6}$ alkenyl, $C_{2-6}$ alkynyl, heteroalkyl, cycloalkyl, heterocyclyl, aryl, alkylaryl, heteroaryl, alkylheteroaryl, an amino acid or an oligopeptide;
wherein an amine of the amino acid or oligopeptide is substituted or unsubstituted; and
n is an integer from 0 to 6;
or a diastereomer, enantiomer or pharmaceutically acceptable salt of the compound.

In some embodiments, the compound having the structure:

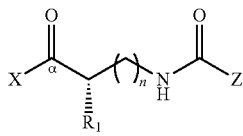

wherein
X is a therapeutic agent containing at least one amine nitrogen and the amine nitrogen on the therapeutic agent covalently bonds directly to carbon α;
Z is $CH_3$ or $CF_3$;
$R_1$ is —H, —$NR_2R_3$, —NH—C(=O)—$R_4$, —NH—C(=O)—$OR_4$, —$CH_2$—C(=O)—$NR_5R_6$, —$OR_7$, —$CO_2R_2$, $C_{1-6}$ alkyl, $C_{2-6}$ alkenyl, $C_{2-6}$ alkynyl, aryl, or heteroaryl,
wherein $R_2$, $R_3$, $R_4$, $R_5$, $R_6$ and $R_7$ are each, independently, —H, $C_{1-6}$ alkyl, $C_{2-6}$ alkenyl, $C_{2-6}$ alkynyl, heteroalkyl, cycloalkyl, heterocyclyl, aryl, alkylaryl, heteroaryl, alkylheteroaryl, an amino acid or an oligopeptide;
wherein an amine of the amino acid or oligopeptide is substituted or unsubstituted; and
n is an integer from 0 to 6;
or a diastereomer, enantiomer or pharmaceutically acceptable salt of the compound.

In some embodiments, the compound wherein
$R_1$ is —$NR_2R_3$, —NH—C(=O)—$R_4$, —NH—C(=O)—$OR_4$,
wherein $R_2$, $R_3$, $R_4$, $R_5$, $R_6$ and $R_7$ are each, independently, —H, $C_{1-6}$ alkyl, $C_{2-6}$ alkenyl, $C_{2-6}$ alkynyl, heteroalkyl, cycloalkyl, heterocyclyl, aryl, alkylaryl, heteroaryl, alkylheteroaryl, an amino acid or oligopeptide;
wherein an amine of the amino acid or oligopeptide is substituted or unsubstituted; and
n is 4.

In some embodiments, the compound wherein n is 3, 4 or 5.

In some embodiments, the compound wherein
$R_1$ is —$NR_2R_3$,
wherein
$R_2$ is —H; and
$R_3$ is an amino acid,
wherein the amino acid is bonded to the nitrogen through an amide bond.

In some embodiments, the compound wherein
$R_1$ is —$NR_2R_3$,
wherein
$R_2$ is —H; and
$R_3$ is an oligopeptide,
wherein the oligopeptide is bonded to the nitrogen through an amide bond.

In some embodiments, the compound wherein
$R_1$ is

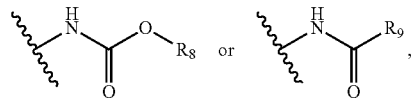

wherein $R_8$ and $R_9$ are each independently —H, —$CH_3$, t-butyl, phenyl, or benzyl.

In some embodiments, the compound wherein
$R_1$ is

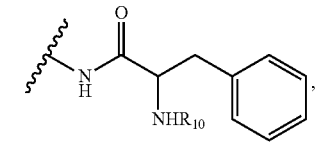

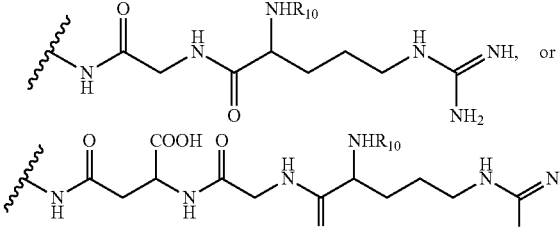

wherein $R_{10}$ is —H, —$CH_3$, Ac, —C(O)—Ot-Bu, —C(O)—$OCH_2Ph$, —CHO, phenyl, or benzyl.

In some embodiments, the compound wherein X is a chemotherapeutic agent containing at least one amine nitrogen.

In some embodiments, the compound wherein X is a nucleoside or deoxynucleoside containing at least one amine nitrogen.

In some embodiments, the compound wherein X is puromycin, 5-fluorocytidine, 2'-deoxy-5-fluorocytidine, 5'-deoxy-5-fluorocytidine, 5'-deoxy-5-fluorocytidine, gemcitabine, cytarabine, cladribine, troxacitabine, adriamycin, alimta, aminolevulinic acid, azacitidine, bleomycin, cerubidine, clofarabine, clofarex, crizotinib, dasatinib, daunorubicin, decitabine, doxil, deoxorubicin, ellence, epirubicin, eribulin mesylate, erlotinib, evacet, fludara, fludarabine phosphate, fluorouracil, fulvestrant, gefitinib, gemcitabine hydrochloride, imiquimod, lapatinib ditosylate, lenalidomide, letrozole, leucovorin, levulan, matulane, methotrexate, mitomycin C, nelarabine, nilotinib, pazopanib, pemetrexed, pralatrexate, prednisone, wellcovorin, xalkori, discodermolide, or blasticidin.

The present invention provides compound having the structure:

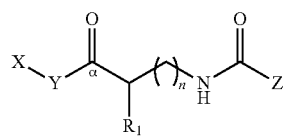

wherein
X is a therapeutic agent;
Y is a chemical linker;
  wherein Y is present or absent, and when present,
  Y is a chemical linker containing at least one amine nitrogen,
    wherein the amine nitrogen on the linker covalently bonds directly to carbon α, or
  Y is a para-aminobenzyl alcohol linker,
    wherein the nitrogen on the linker Y connects directly to carbon α and the oxygen on the linker Y connects to the therapeutic agent X, or the oxygen on the linker Y connects directly to carbon α and the nitrogen on the linker Y connects to the therapeutic agent X through an amide bond;
Z is $CH_3$ or $CF_3$;
$R_1$ is —H, —$NR_2R_3$, —NH—C(=O)—$R_4$, —NH—C(=O)—$OR_4$, —$CH_2$—C(=O)—$NR_5R_6$, —$OR_7$, —$CO_2R_7$, $C_{1-6}$ alkyl, $C_{2-6}$ alkenyl, $C_{2-6}$ alkynyl, aryl, or heteroaryl,
  wherein $R_2$, $R_3$, $R_4$, $R_5$, $R_6$ and $R_7$ are each, independently, —H, $C_{1-6}$ alkyl, $C_{2-6}$ alkenyl, $C_{2-6}$ alkynyl, heteroalkyl, cycloalkyl, heterocyclyl, aryl, alkylaryl, heteroaryl, alkylheteroaryl, an amino acid or an oligopeptide;
    wherein the amine of the amino acid or oligopeptide is substituted or unsubstituted; and
n is an integer from 0 to 6;
or a diastereomer, enantiomer or pharmaceutically acceptable salt of the compound.

In some embodiment, the compound having the structure:

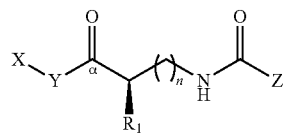

wherein
X is a therapeutic agent;
Y is a chemical linker;
  wherein Y is present or absent, and when present,
  Y is a chemical linker containing at least one amine nitrogen,
    wherein the amine nitrogen on the linker covalently bonds directly to carbon α, or
  Y is a para-aminobenzyl alcohol linker,
    wherein the nitrogen on the linker Y connects directly to carbon α and the oxygen on the linker Y connects to the therapeutic agent X, or the oxygen on the linker Y connects directly to carbon α and the nitrogen on the linker Y connects to the therapeutic agent X through an amide bond;
Z is $CH_3$ or $CF_3$;
$R_1$ is —H, —$NR_2R_3$, —NH—C(=O)—$R_4$, —NH—C(=O)—$OR_4$, —$CH_2$—C(=O)—$NR_5R_6$, —$OR_7$, —$CO_2R_7$, $C_{1-6}$ alkyl, $C_{2-6}$ alkenyl, $C_{2-6}$ alkynyl, aryl, or heteroaryl,
  wherein $R_2$, $R_3$, $R_4$, $R_5$, $R_6$ and $R_7$ are each, independently, —H, $C_{1-6}$ alkyl, $C_{2-6}$ alkenyl, $C_{2-6}$ alkynyl, heteroalkyl, cycloalkyl, heterocyclyl, aryl, alkylaryl, heteroaryl, alkylheteroaryl, an amino acid or an oligopeptide;
    wherein the amine of the amino acid or oligopeptide is substituted or unsubstituted; and
n is an integer from 0 to 6;
or a diastereomer, enantiomer or pharmaceutically acceptable salt of the compound.

In some embodiments the compound having the structure:

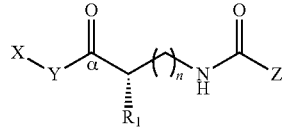

wherein
X is a therapeutic agent;
Y is a chemical linker;
  wherein Y is present or absent, and when present,
  Y is a chemical linker containing at least one amine nitrogen,
    wherein the amine nitrogen on the linker covalently bonds directly to carbon α, or
  Y is a para-aminobenzyl alcohol linker,
    wherein the nitrogen on the linker Y connects directly to carbon α and the oxygen on the linker Y connects to the therapeutic agent X, or the oxygen on the linker Y connects directly to carbon α and the nitrogen on the linker Y connects to the therapeutic agent X through an amide bond;
Z is $CH_3$ or $CF_3$;
$R_1$ is —H, —$NR_2R_3$, —NH—C(=O)—$R_4$, —NH—C(=O)—$OR_4$, —$CH_2$—C(=O)—$NR_5R_6$, —$OR_7$, —$CO_2R_7$, $C_{1-6}$ alkyl, $C_{2-6}$ alkenyl, $C_{2-6}$ alkynyl, aryl, or heteroaryl,
  wherein $R_2$, $R_3$, $R_4$, $R_5$, $R_6$ and $R_7$ are each, independently, —H, $C_{1-6}$ alkyl, $C_{2-6}$ alkenyl, $C_{2-6}$ alkynyl, heteroalkyl, cycloalkyl, heterocyclyl, aryl, alkylaryl, heteroaryl, alkylheteroaryl, an amino acid or an oligopeptide;
    wherein the amine of the amino acid or oligopeptide is substituted or unsubstituted; and
n is an integer from 0 to 6;
or a diastereomer, enantiomer or pharmaceutically acceptable salt of the compound.

In some embodiments, the compound wherein
R₁ is —NR₂R₃, —NH—C(=O)—R₄, —NH—C(=O)—OR₄, —CH₂—C(=O)—NR₅R₆, —OR₇, —CO₂R₇, C₂₋₆ alkyl, C₂₋₆ alkenyl, C₂₋₆ alkynyl, aryl, or heteroaryl,
wherein R₂, R₃, R₄, R₅, R₆ and R₇ are each, independently, —H, C₁₋₆ alkyl, C₂₋₆ alkenyl, C₂₋₆ alkynyl, heteroalkyl, cycloalkyl, heterocyclyl, aryl, alkylaryl, heteroaryl, alkylheteroaryl, an amino acid or an oligopeptide;
wherein the amine of the amino acid or oligopeptide is substituted or unsubstituted; and
n is 4.

In some embodiments, the compound wherein
Y is present, and Y is a chemical linker containing at least one amine nitrogen,
wherein the amine nitrogen on the linker covalently bonds directly to carbon α.

In some embodiments, the compound wherein
Y is present, and Y is a para-aminobenzyl alcohol linker,
wherein the nitrogen on the linker Y connects to directly to carbon α and the oxygen on the linker Y connects to the therapeutic agent X, or the oxygen on the linker Y connects directly to carbon α and the nitrogen on the linker Y connects to the therapeutic agent X through an amide bond.

In some embodiments, the compound wherein the nitrogen on the linker Y connects to directly to carbon α and the oxygen on the linker Y connects to the therapeutic agent X.

In some embodiments, the compound wherein the oxygen on the linker Y connects directly to carbon α and the nitrogen on the linker Y connects to the therapeutic agent X through an amide bond.

In some embodiments, the compound wherein n is 3, 4 or 5.

In some embodiments, the compound wherein
Y is absent.

In some embodiments, the compound wherein
Y is present.

In some embodiments, the compound wherein
Y is present and

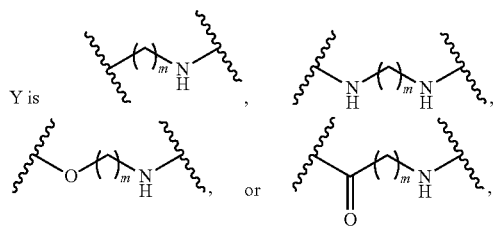

wherein
m is 0 to 6; and
a nitrogen on the linker Y connects to directly to carbon α.

In some embodiments, the compound wherein
R₁ is —NR₂R₃,
wherein
R₂ is —H; and
R₃ is an amino acid,
wherein the amino acid is bonded to the nitrogen through an amide bond.

In some embodiments, the compound wherein
R₁ is —NR₂R₃,
wherein
R₂ is —H; and
R₃ is an oligopeptide,
wherein the oligopeptide is bonded to the nitrogen through an amide bond.

In some embodiments, the compound wherein
R₁ is

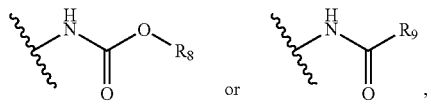

wherein R₈ and R₉ are each independently —H, —CH₃, t-butyl, phenyl, or benzyl.

In some embodiments, the compound wherein
R₁ is

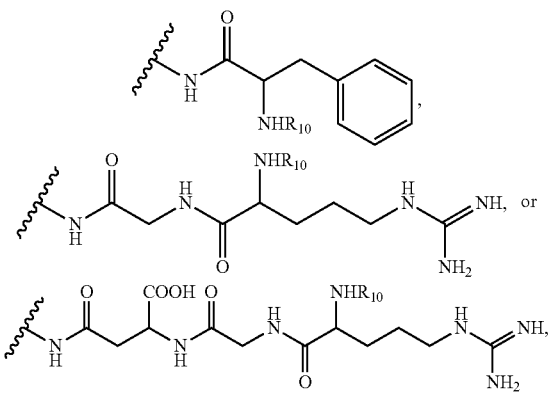

wherein R₁₀ is —H, —CH₃, Ac, —C(O)—Ot—Bu, —C(O)—OCH₂Ph, —CHO, phenyl, or benzyl.

In some embodiments, the compound wherein Y is absent, and the therapeutic agent X contains at least one amine and an amine nitrogen on the therapeutic agent X connects directly to carbon α.

In some embodiments, the compound wherein X is a chemotherapeutic agent.

In some embodiments, the compound wherein X is a nucleoside or deoxynucleoside.

In some embodiments, the compound wherein X is puromycin, 5-fluorocytidine, 2'-deoxy-5-fluorocytidine, 5'-deoxy-5-fluorocytidine, 5'-deoxy-5-fluorocytidine, gemcitabine, cytarabine, cladribine, troxacitabine, abiraterone acetate, abraxane, adriamycin, afinitor, alimta, aloxi, amboclorin, aminolevulinic acid, anastrozole, aprepitant, aromasin, axitinib, azacitidine, bendamustine hydrochloride, bexarotene, bleomycin, bortezomib, cabazitaxel, capecitabine, cerubidine, clofarabine, clofarex, crizotinib, dacarbazine, dasatinib, daunorubicin hydrochloride, decitabine, degarelix, dexrazoxane hydrochloride, docetaxel, doxil, deoxorubicin, ellence, epirubicin hydrochloride, eribulin mesylate, erlotinib hydrochloride, etoposide, evacet, everolimus, fludara, fludarabine phosphate, fluorouracil, fulvestrant, gefitinib, gemcitabine hydrochloride, imatinib mesylate, imiquimod, irinotecan hydrochloride, ixabepilone, lapatinib ditosylate, lenalidomide, letrozole, leucovorin calcium, leuprorelin, levulan, lomustine, lupron, matulane, methotrexate, mitomycin C, navelbine, nelarabine, nexavar, nilotinib, nolvadex, palonosetron hydrochloride, pazopanib hydrochloride, pemetrexed disodium, pralatrexate, prednisone, procarbazine hydrochloride, raloxifene hydrochloride, ruxolitinib phosphate, sorafenib tosylate, sunitinib malate, tamoxifen citrate, taxol, taxotere, temozolomide, temsirolimus, topotecan hydrochloride, toremifene, vandetanib, vemurafenib, vinblastine sulfate, vincristine sulfate, vinorelbine tartrate, vismodegib, wellcovorin, xalkori, zevalin, zinecard, zoledronic acid, discodermolide, or blasticidin.

In some embodiments, the compound wherein Z is $CH_3$.

In some embodiments, the compound wherein Z is $CF_3$.

In some embodiments, the compound wherein $R_1$ is

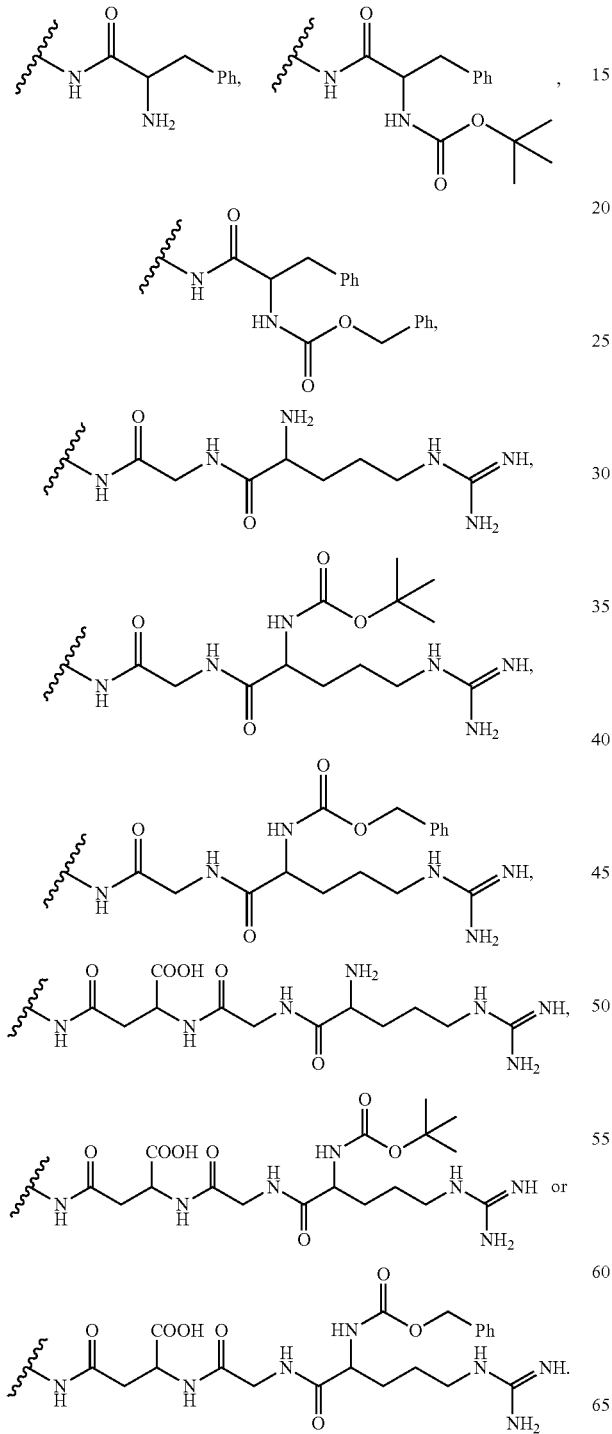

In some embodiments, the compound having the structure:

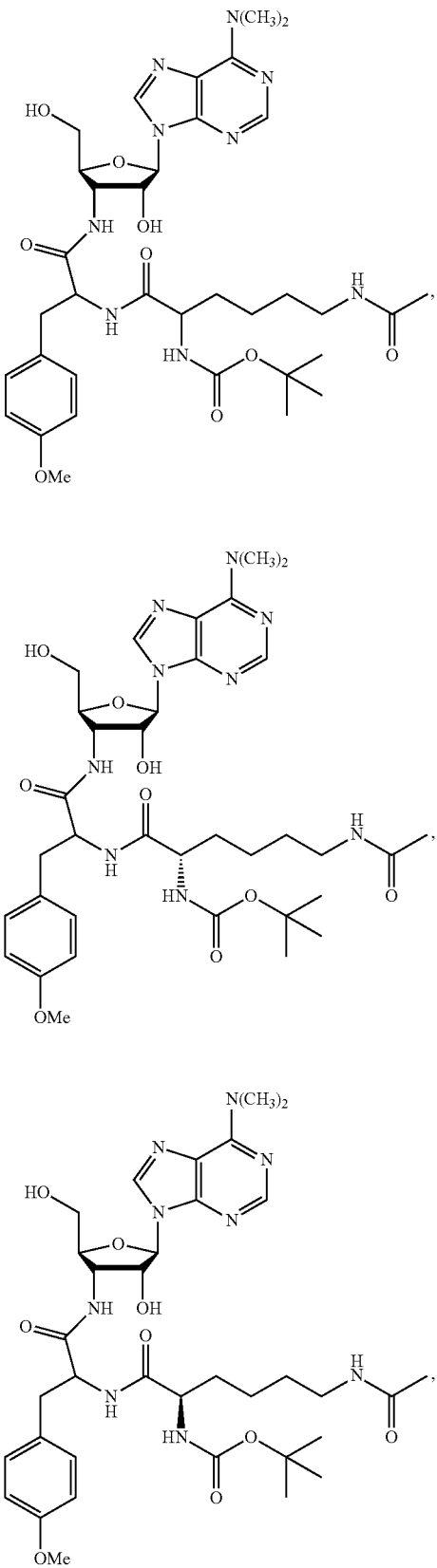

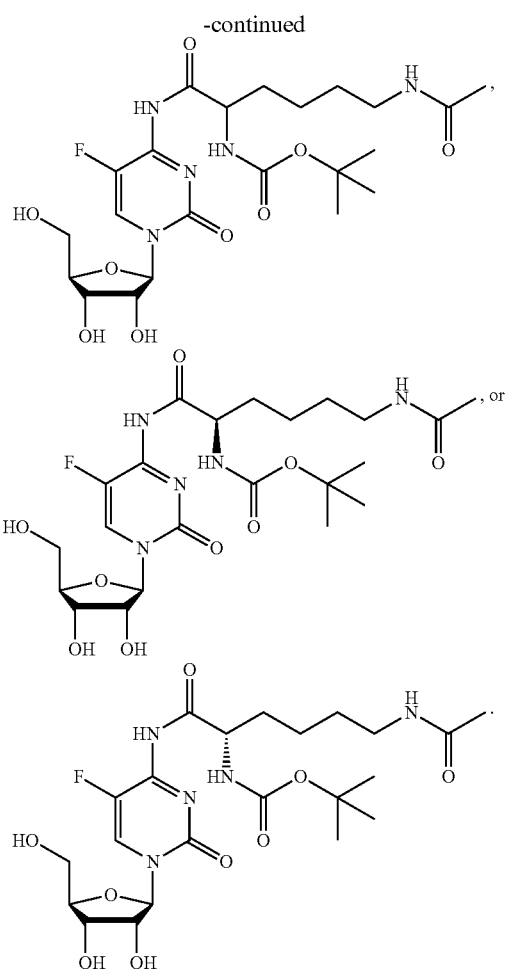
In some embodiments, the compound having the structure:
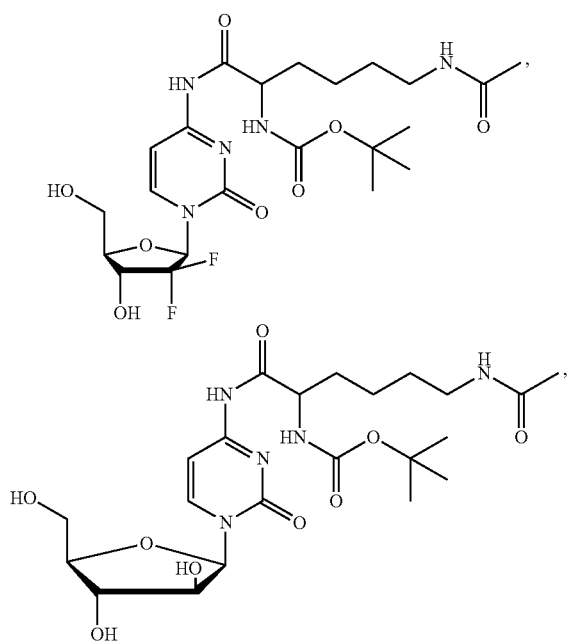
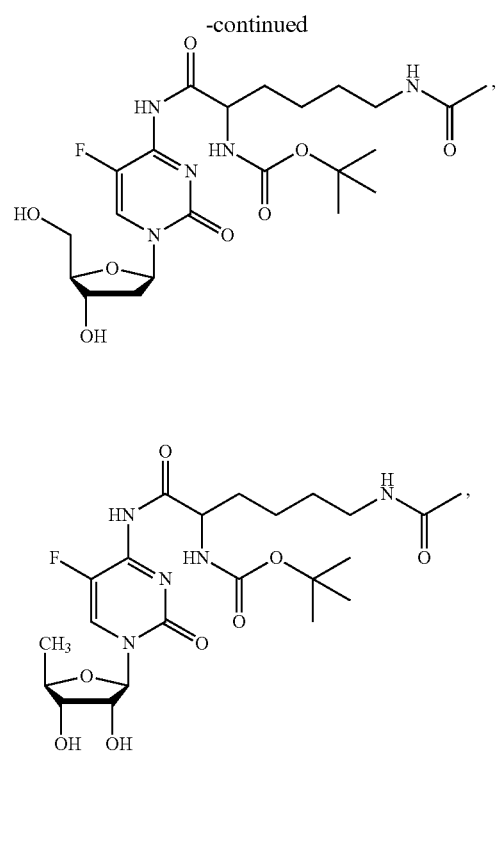
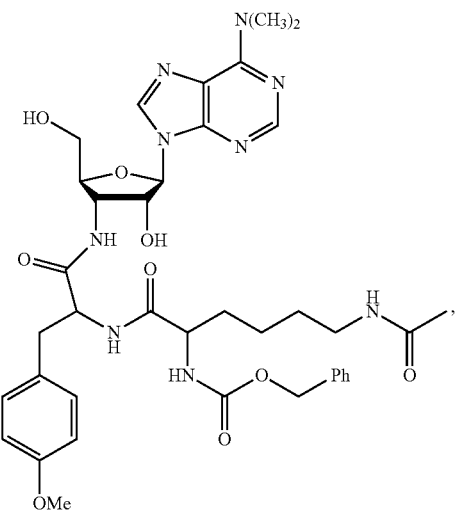
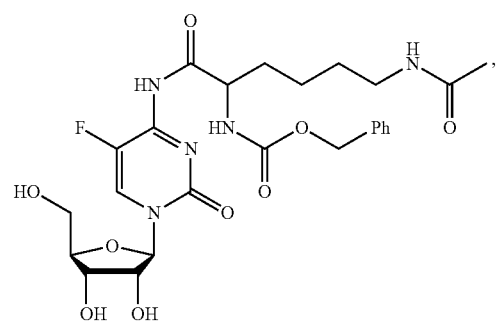

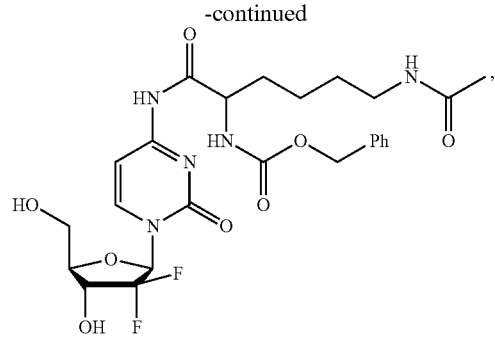
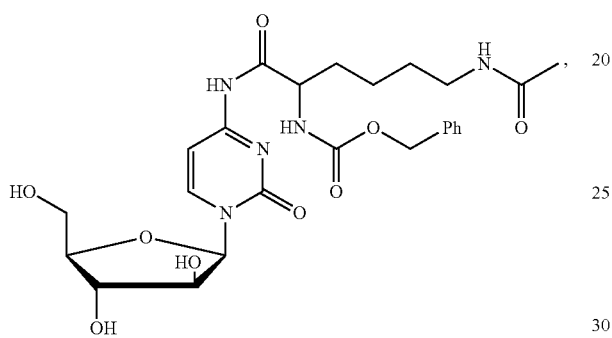
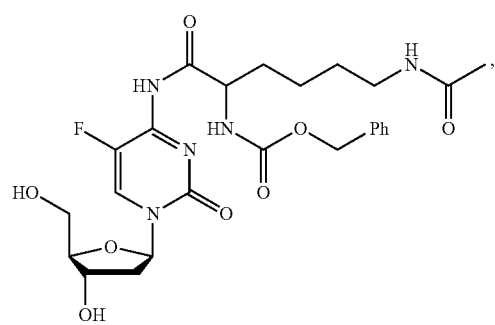
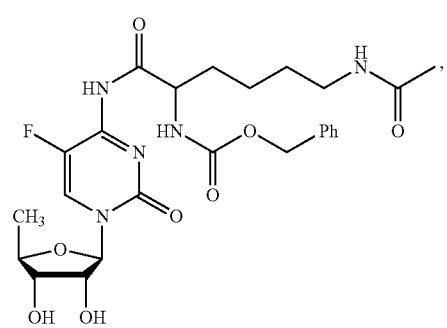
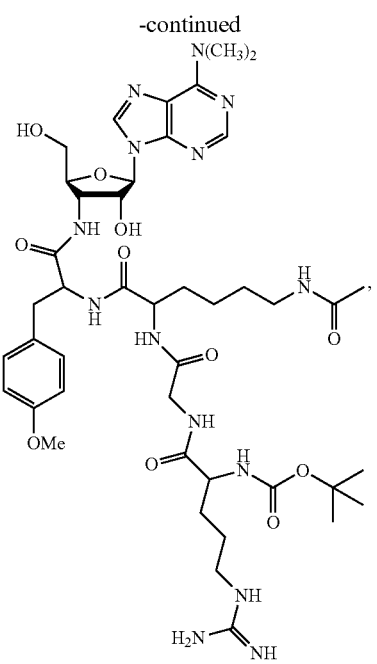
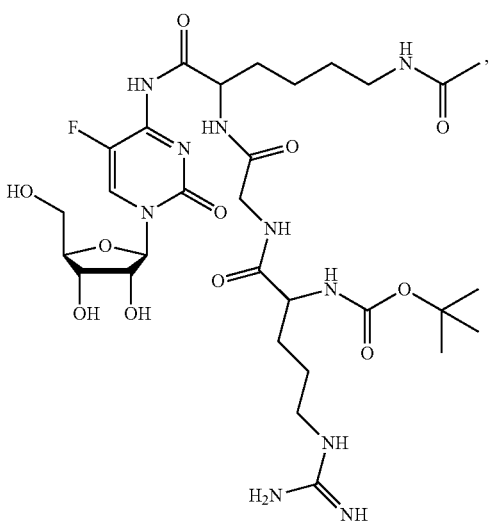

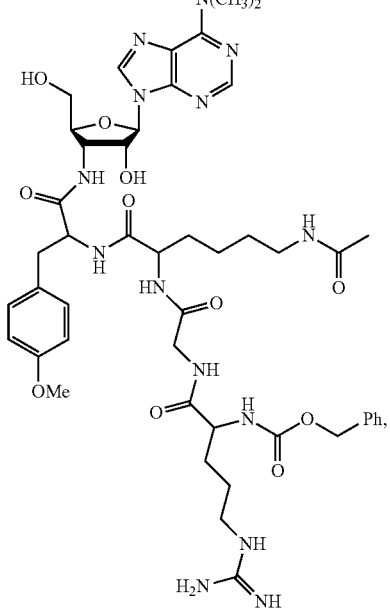

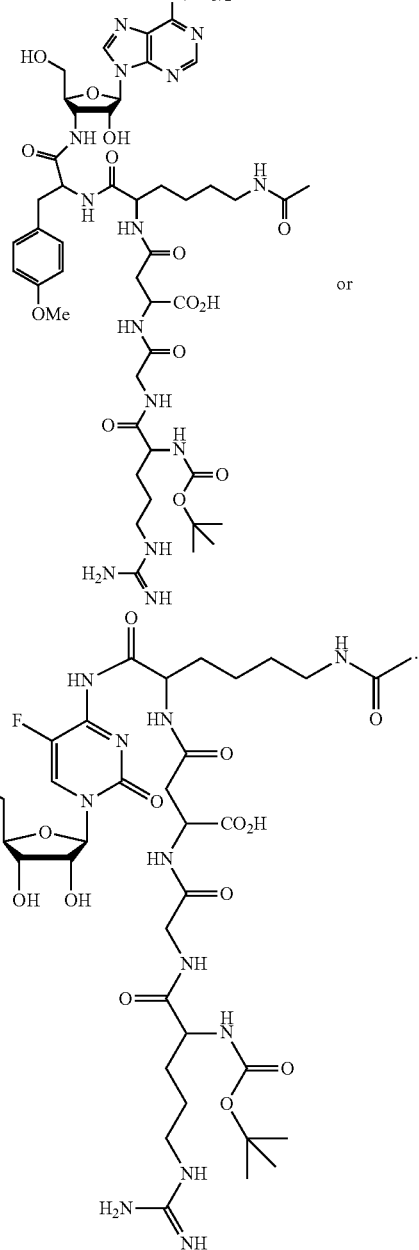

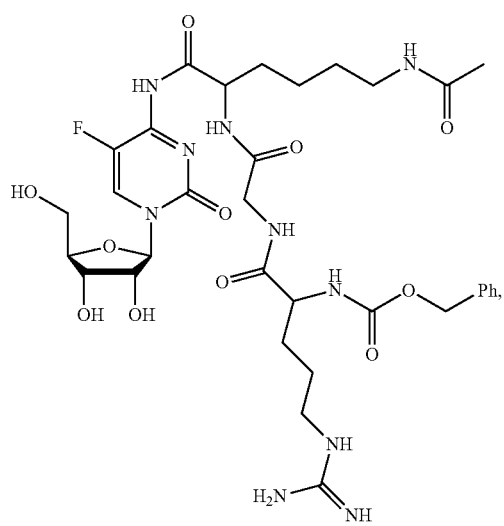

In some embodiments, the compound wherein
R$_1$ is —NHBoc;
n is 4;
X is puromycin or 5-fluorocytidine; and
Z is CH$_3$.

In some embodiments, a pharmaceutical composition comprising the compound of the present invention and a pharmaceutically acceptable carrier.

In some embodiments, a method for reducing one or more symptoms of disease in a subject, comprising administering an effective amount of the compound of the present invention or the composition of the present invention to the subject so as to treat the disease in the subject.

In some embodiments, the disease is characterized by or caused by cells which have elevated levels of histone deacetylases or proteases or both.

In some embodiments, the disease is cancer.

In some embodiments, the compound or composition inhibits cancer cell metastasis.

In some embodiments, the compound or composition inhibits cancer cell proliferation.

In some embodiments, the cancer cells have elevated levels of histone deacetylases or proteases or both.

In some embodiments, the cancer is colon, pancreatic, liver, breast, prostate, or cervical cancer.

In some embodiments, a method for inhibiting growth of a tumor comprising contacting the tumor with a compound of the present invention or the composition of the present invention.

In some embodiments, a method for reducing the size a tumor comprising contacting the tumor with a compound of the present invention or the composition of the present invention.

In some embodiments, the compound or composition of the present invention for use in treating a subject suffering from cancer.

In some embodiments, the compound or composition of the present invention for use in treating cancer.

In some embodiments, the compound or composition of the present invention for use in inhibiting growth of a tumor.

In some embodiments, the compound or composition of the present invention for use in reducing the size a tumor.

In some embodiments, the compound or composition of the present invention for use in treating a disease that is caused by cells which have elevated levels of histone deacetylases or proteases or both.

The invention provides a compound having the structure:

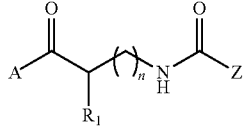

wherein
A is OH, O($C_1$-$C_4$ alkyl) or O($CH_2$-aryl);
Z is $CH_3$ or $CF_3$;
$R_1$ is —H, —$NR_2R_3$, —NH—C(=O)—$R_4$, —NH—C(=O)—$OR_4$, —$CH_2$—C(=O)—$NR_5R_6$, —$OR_7$, —$CO_2R_7$, $C_{1-6}$ alkyl, $C_{2-6}$ alkenyl, $C_{2-6}$ alkynyl, aryl, or heteroaryl,
wherein $R_2$, $R_3$, $R_4$, $R_5$, $R_6$ and $R_7$ are each, independently, —H, $C_{1-6}$ alkyl, $C_{2-6}$ alkenyl, $C_{2-6}$ alkynyl, heteroalkyl, cycloalkyl, heterocyclyl, aryl, alkylaryl, heteroaryl, alkylheteroaryl, an amino acid or an oligopeptide;
wherein an amine of the amino acid or oligopeptide is substituted or unsubstituted; and
n is an integer from 0 to 6;
or a diastereomer, enantiomer or pharmaceutically acceptable salt of the compound.

In some embodiments, the compound having the structure:

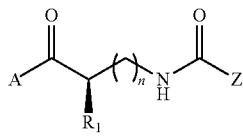

wherein
A is OH, O($C_1$-$C_6$ alkyl) or O($CH_2$-aryl);
Z is $CH_3$ or $CF_3$;
$R_1$ is —H, —$NR_2R_3$, —NH—C(=O)—$R_4$, —NH—C(=O)—$OR_4$, —$CH_2$—C(=O)—$NR_5R_6$, —$OR_7$, —$CO_2R_7$, $C_{1-6}$ alkyl, $C_{2-6}$ alkenyl, $C_{2-6}$ alkynyl, aryl, or heteroaryl,
wherein $R_2$, $R_3$, $R_4$, $R_5$, $R_6$ and $R_7$ are each, independently, —H, $C_{1-6}$ alkyl, $C_{2-6}$ alkenyl, $C_{2-6}$ alkynyl, heteroalkyl, cycloalkyl, heterocyclyl, aryl, alkylaryl, heteroaryl, alkylheteroaryl, an amino acid or an oligopeptide;
wherein an amine of the amino acid or oligopeptide is substituted or unsubstituted; and
n is an integer from 0 to 6;
or a diastereomer, enantiomer or pharmaceutically acceptable salt of the compound.

In some embodiments, the compound having the structure:

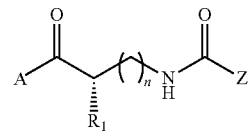

wherein
A is OH, O($C_1$-$C_6$ alkyl) or O($CH_2$-aryl);
Z is $CH_3$ or $CF_3$;
$R_1$ is —H, —$NR_2R_3$, —NH—C(=O)—$R_4$, —NH—C(=O)—$OR_4$, —$CH_2$—C(=O)—$NR_5R_6$, —$OR_7$, —$CO_2R_7$, $C_{1-6}$ alkyl, $C_{2-6}$ alkenyl, $C_{2-6}$ alkynyl, aryl, or heteroaryl,
wherein $R_2$, $R_3$, $R_4$, $R_5$, $R_6$ and $R_7$ are each, independently, —H, $C_{1-6}$ alkyl, $C_{2-6}$ alkenyl, $C_{2-6}$ alkynyl, heteroalkyl, cycloalkyl, heterocyclyl, aryl, alkylaryl, heteroaryl, alkylheteroaryl, an amino acid or an oligopeptide;
wherein an amine of the amino acid or oligopeptide is substituted or unsubstituted; and
n is an integer from 0 to 6;
or a diastereomer, enantiomer or pharmaceutically acceptable salt of the compound.

In some embodiments, the invention provides a method of reducing one or more symptoms of any disease that involves carcinomas or cancer including but not limited to lung cancer, breast cancer, prostate cancer, cervical cancer, pancreatic cancer, colon cancer, ovarian cancer; stomach cancer, esophagus cancer, mouth cancer, tongue cancer, gum cancer, skin cancer (e.g., melanoma, basal cell carcinoma, Kaposi's sarcoma, etc.), muscle cancer, heart cancer, liver cancer, bronchial cancer, cartilage cancer, bone cancer, testis cancer, kidney cancer, endometrium cancer, uterus cancer, bladder cancer, bone marrow cancer, lymphoma cancer, spleen cancer, thymus cancer, thyroid cancer, brain cancer, neuron cancer, mesothelioma, gall bladder cancer, ocular cancer (e.g., cancer of the cornea, cancer of uvea, cancer of the choroids, cancer of the macula, vitreous humor cancer, etc.), joint cancer (such as synovium cancer), glioblastoma, lymphoma, and leukemia. Malignant neoplasms are further exemplified by sarcomas (such as osteosarcoma and Kaposi's sarcoma).

As used herein, the term "amino acid" refers to any natural or unnatural amino acid including its salt form, ester derivative, protected amine derivative and/or its isomeric forms. Amino Acids comprise, by way of non-limiting example: Agmatine, Alanine Beta-Alanine, Arginine, Asparagine, Aspartic Acid, Cysteine, Glutamine, Glutamic Acid, Glycine, Histidine, Isoleucine, Leucine, Lysine, Methionine, Phenylalanine, Phenyl Beta-Alanine, Proline, Serine, Threonine, Tryptophan, Tyrosine, and Valine. The amino acids may be L or D amino acids.

As used herein, the term "oligopeptide" refers to a peptide comprising of between 2 and 20 amino acids and includes dipeptides, tripeptides, tetrapeptides, pentapeptides, etc.

An amino acid or oligopeptide may be covalently bonded to an amine of another molecule through an amide linkage, resulting in the loss of an "OH" from the amino acid or oligopeptide.

As used herein, the term "para-aminobenzyl alcohol linker" refers to

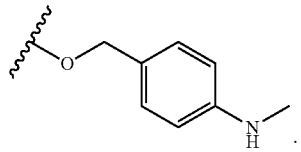 [SMILES: *OCc1ccc(NC)cc1]

As used herein, the term "therapeutic agent" refers to any agent used to treat a disease or that provides a beneficial therapeutic effect to a subject.

As used herein, the term "chemotherapeutic agent" refers to any agent used to treat cancer or that provides a beneficial therapeutic effect to a subject suffering from cancer.

Certain embodiments of the invention provide compositions or compounds containing therapeutic agents such as a cytotoxin, e.g., a cytostatic or cytocidal agent. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, coichicin, doxorubicin, daunorubicin, dihydroxy anthracin dione, mitoxantrone, mithramycin, actinomycin D, I-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II), (DDP) cisplatin), anthracyclines (e.g., daunorubicin (formerly daunomycin) and doxorubicin), antibiotics (e.g., dactinomycin (fonnerly actinomycin), bleomycin, mithramycin, and anthramycin), and anti-mitotic agents (e.g., vincristine and vinblastine).

Certain embodiments of the invention provide compositions or compounds containing chemotherapeutic agents, which are any agents detrimental to cancer cells. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mito-xantrone, amsacrine, chlorambucil, methylcyclohexylnitrosurea, nitrogen mustards, melphalan, cyclophosphamide, 6-mercaptopurine, 6-thioguanine, cyt-arabine, 5-azacytidine, hydroxyurea, deoxycoformycin, 4-hydroxyperoxycyclophosphor-amide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). See, generally, The Merck Manual of Diagnosis and Therapy, 15th Ed. 1987, pp. 1206-1228, Berkow et al., eds., Rahway, N.J. When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to non-steroidal anti-inflammatory drugs and corticosteroids, and antiviral drugs, including but not limited to ribivirin, vidarabine, acyclovir and ganciclovir, may also be combined in compositions of the invention. See, generally, The Merck Manual of Diagnosis and Therapy, 15th Ed., Berkow et al., eds., 1987, Rahway, N.J., pages 2499-2506 and 46-49, respectively). Other chemotherapeutic agents are also within the scope of this invention. Two or more combined compounds may be used together or sequentially.

The therapeutic or chemotherapeutic agent is not to be construed as limited to classical chemical therapeutic or chemotherapeutic agents. For example, the agent may be a protein, nucleotide or polypeptide possessing a desired biological activity.

However, the term "therapeutic agent" does not include fluorogenic probes, optical probes, radiolabeled probes, dyes, or other agents that function as imaging or contrast agents.

As used herein, the term "histone deacetylase" or "HDAC" refers to any member of the classes of enzymes capable of cleaving an acetyl group (—C(=O)CH$_3$) from proteins, which include, but are not limited to, histones and microtubules. A histone deacetylase may be zinc-dependent. Examples of HDACs include, but are not limited to, HDAC1, HDAC2, HDAC3, HDAC4, HDAC5, HDAC6, HDAC7, HDAC8, HDAC9, HDAC10, and HDAC11. Additional examples of histone decetylases include, but are not limited to, the Sir2 proteins SIRT1, SIRT2, SIRT3, SIRT4, SIRT5, SIRT6 and SIRT7.

As used herein, "protease" refers to any enzyme that conducts proteolysis.

As used herein, "proteolysis" refers to the hydrolysis or cleavage of a peptide or amide bond.

As used herein, the term "activity" refers to the activation, production, expression, synthesis, intercellular effect, and/or pathological or aberrant effect of the referenced molecule, either inside and/or outside of a cell. Such molecules include, but are not limited to, cytokines, enzymes, growth factors, pro-growth factors, active growth factors, and pro-enzymes. Molecules such as cytokines, enzymes, growth factors, pro-growth factors, active growth factors, and pro-enzymes may be produced, expressed, or synthesized within a cell where they may exert an effect. Such molecules may also be transported outside of the cell to the extracellular matrix where they may induce an effect on the extracellular matrix or on a neighboring cell. It is understood that activation of inactive cytokines, enzymes and pro-enzymes may occur inside and/or outside of a cell and that both inactive and active forms may be present at any point inside and/or outside of a cell. It is also understood that cells may possess basal levels of such molecules for normal function and that abnormally high or low levels of such active molecules may lead to pathological or aberrant effects that may be corrected by pharmacological intervention.

This invention also provides isotopic variants of the compounds disclosed herein, including wherein the isotopic atom is $^2$H and/or wherein the isotopic atom $^{13}$C. Accordingly, in the compounds provided herein hydrogen can be enriched in the deuterium isotope. It is to be understood that the invention encompasses all such isotopic forms.

It is understood that the structures described in the embodiments of the methods hereinabove can be the same as the structures of the compounds described hereinabove.

It is understood that where a numerical range is recited herein, the present invention contemplates each integer between, and including, the upper and lower limits, unless otherwise stated.

Except where otherwise specified, if the structure of a compound of this invention includes an asymmetric carbon atom, it is understood that the compound occurs as a racemate, racemic mixture, and isolated single enantiomer. All such isomeric forms of these compounds are expressly included in this invention. Except where otherwise specified, each stereogenic carbon may be of the R or S configuration. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis, such as those described in "Enantiomers, Racemates and Resolutions" by J. Jacques, A. Collet and S. Wilen, Pub. John Wiley & Sons, NY, 1981. For example, the resolution may be carried out by preparative chromatography on a chiral column.

The subject invention is also intended to include all isotopes of atoms occurring on the compounds disclosed herein. Isotopes include those atoms having the same atomic number but different mass numbers. By way of general example and without limitation, isotopes of hydrogen include tritium and deuterium. Isotopes of carbon include C-13 and C-14.

It will be noted that any notation of a carbon in structures throughout this application, when used without further notation, are intended to represent all isotopes of carbon, such as $^{12}$C, $^{13}$C, or $^{14}$C. Furthermore, any compounds containing $^{13}$C or $^{14}$C may specifically have the structure of any of the compounds disclosed herein.

It will also be noted that any notation of a hydrogen in structures throughout this application, when used without further notation, are intended to represent all isotopes of hydrogen, such as $^1$H, $^2$H, or $^3$H. Furthermore, any compounds containing $^2$H or $^3$H may specifically have the structure of any of the compounds disclosed herein.

Isotopically-labeled compounds can generally be prepared by conventional techniques known to those skilled in the art using appropriate isotopically-labeled reagents in place of the non-labeled reagents employed.

In the compounds used in the method of the present invention, the substituents may be substituted or unsubstituted, unless specifically defined otherwise.

In the compounds used in the method of the present invention, alkyl, heteroalkyl, monocycle, bicycle, aryl, heteroaryl and heterocycle groups can be further substituted by replacing one or more hydrogen atoms with alternative non-hydrogen groups. These include, but are not limited to, halo, hydroxy, mercapto, amino, carboxy, cyano and carbamoyl.

It is understood that substituents and substitution patterns on the compounds used in the method of the present invention can be selected by one of ordinary skill in the art to provide compounds that are chemically stable and that can be readily synthesized by techniques known in the art from readily available starting materials. If a substituent is itself substituted with more than one group, it is understood that these multiple groups may be on the same carbon or on different carbons, so long as a stable structure results.

In choosing the compounds used in the method of the present invention, one of ordinary skill in the art will recognize that the various substituents, i.e. $R_1$, $R_2$, etc. are to be chosen in conformity with well-known principles of chemical structure connectivity.

As used herein, "alkyl" includes both branched and straight-chain saturated aliphatic hydrocarbon groups having the specified number of carbon atoms and may be unsubstituted or substituted. Thus, $C_1$-$C_n$ as in "$C_1$-$C_n$ alkyl" is defined to include groups having 1, 2, . . . , n−1 or n carbons in a linear or branched arrangement. For example, $C_1$-$C_6$, as in "$C_1$-$C_6$ alkyl" is defined to include groups having 1, 2, 3, 4, 5, or 6 carbons in a linear or branched arrangement, and specifically includes methyl, ethyl, n-propyl, isopropyl, n-butyl, t-butyl, pentyl, hexyl, and octyl.

As used herein, "alkenyl" refers to a non-aromatic hydrocarbon radical, straight or branched, containing at least 1 carbon to carbon double bond, and up to the maximum possible number of non-aromatic carbon-carbon double bonds may be present, and may be unsubstituted or substituted. For example, "$C_2$-$C_6$ alkenyl" means an alkenyl radical having 2, 3, 4, 5, or 6 carbon atoms, and up to 1, 2, 3, 4, or 5 carbon-carbon double bonds respectively. Alkenyl groups include ethenyl, propenyl, butenyl and cyclohexenyl.

The term "alkynyl" refers to a hydrocarbon radical straight or branched, containing at least 1 carbon to carbon triple bond, and up to the maximum possible number of non-aromatic carbon-carbon triple bonds may be present, and may be unsubstituted or substituted. Thus, "$C_2$-$C_6$ alkynyl" means an alkynyl radical having 2 or 3 carbon atoms and 1 carbon-carbon triple bond, or having 4 or 5 carbon atoms and up to 2 carbon-carbon triple bonds, or having 6 carbon atoms and up to 3 carbon-carbon triple bonds. Alkynyl groups include ethynyl, propynyl and butynyl.

"Alkylene", "alkenylene" and "alkynylene" shall mean, respectively, a divalent alkane, alkene and alkyne radical, respectively. It is understood that an alkylene, alkenylene, and alkynylene may be straight or branched. An alkylene, alkenylene, and alkynylene may be unsubstituted or substituted.

As used herein, "aryl" is intended to mean any stable monocyclic, bicyclic or polycyclic carbon ring of up to 10 atoms in each ring, wherein at least one ring is aromatic, and may be unsubstituted or substituted. Examples of such aryl elements include phenyl, p-toluenyl (4-methylphenyl), naphthyl, tetrahydro-naphthyl, indanyl, biphenyl, phenanthryl, anthryl or acenaphthyl. In cases where the aryl substituent is bicyclic and one ring is non-aromatic, it is understood that attachment is via the aromatic ring.

As used herein, the term "polycyclic" refers to unsaturated or partially unsaturated multiple fused ring structures, which may be unsubstituted or substituted.

The term "alkylaryl" refers to alkyl groups as described above wherein one or more bonds to hydrogen contained therein are replaced by a bond to an aryl group as described above. It is understood that an "alkylaryl" group is connected to a core molecule through a bond from the alkyl group and that the aryl group acts as a substituent on the alkyl group. Examples of arylalkyl moieties include, but are not limited to, benzyl(phenylmethyl), p-trifluoromethylbenzyl(4-trifluoromethylphenylmethyl), 1-phenylethyl, 2-phenylethyl, 3-phenylpropyl, 2-phenylpropyl and the like.

The term "heteroaryl", as used herein, represents a stable monocyclic, bicyclic or polycyclic ring of up to 10 atoms in each ring, wherein at least one ring is aromatic and contains from 1 to 4 heteroatoms selected from the group consisting of O, N and S. Bicyclic aromatic heteroaryl groups include phenyl, pyridine, pyrimidine or pyridizine rings that are (a) fused to a 6-membered aromatic (unsaturated) heterocyclic ring having one nitrogen atom; (b) fused to a 5- or 6-membered aromatic (unsaturated) heterocyclic ring having two nitrogen atoms; (c) fused to a 5-membered aromatic (unsaturated) heterocyclic ring having one nitrogen atom together with either one oxygen or one sulfur atom; or (d) fused to a 5-membered aromatic (unsaturated) heterocyclic ring having one heteroatom selected from O, N or S. Heteroaryl groups within the scope of this definition include but are not limited to: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrazolyl, tetrazolopyridyl, thiadiazolyl, thiazolyl, thienyl, triazolyl, azetidinyl, aziridinyl, 1,4-dioxanyl, hexahydroazepinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, tetrahydrothienyl, acridinyl, carbazolyl, cinnolinyl, quinoxalinyl, pyrrazolyl, indolyl, benzotriazolyl, benzothiazolyl, benzoxazolyl, isoxazolyl, isothiazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetra-hydroquinoline. In cases where the heteroaryl substituent is bicyclic and one ring is non-aromatic or contains no heteroatoms, it is understood that attachment is via the aromatic ring or via the heteroatom containing ring, respectively. If the heteroaryl contains nitrogen atoms, it is understood that the corresponding N-oxides thereof are also encompassed by this definition.

The term "alkylheteroaryl" refers to alkyl groups as described above wherein one or more bonds to hydrogen contained therein are replaced by a bond to an heteroaryl group as described above. It is understood that an "alkylheteroaryl" group is connected to a core molecule through a bond from the alkyl group and that the heteroaryl group acts as a substituent on the alkyl group. Examples of alkylheteroaryl moieties include, but are not limited to, —CH$_2$—(C$_5$H$_4$N), —CH$_2$—CH$_2$—(C$_5$H$_4$N) and the like.

The term "heterocycle", "heterocyclyl" or "heterocyclic" refers to a mono- or poly-cyclic ring system which can be saturated or contains one or more degrees of unsaturation and contains one or more heteroatoms. Preferred heteroatoms include N, O, and/or S, including N-oxides, sulfur oxides, and dioxides. Preferably the ring is three to ten-membered and is either saturated or has one or more degrees of unsaturation. The heterocycle may be unsubstituted or substituted, with multiple degrees of substitution being allowed.

Such rings may be optionally fused to one or more of another "heterocyclic" ring(s), heteroaryl ring(s), aryl ring(s), or cycloalkyl ring(s). Examples of heterocycles include, but are not limited to, tetrahydrofuran, pyran, 1,4-dioxane, 1,3-dioxane, piperidine, piperazine, pyrrolidine, morpholine, thiomorpholine, tetrahydrothiopyran, tetrahydrothiophene, 1,3-oxathiolane, and the like.

The alkyl, alkenyl, alkynyl, aryl, heteroaryl and heterocyclyl substituents may be substituted or unsubstituted, unless specifically defined otherwise.

In the compounds of the present invention, alkyl, alkenyl, alkynyl, aryl, heterocyclyl and heteroaryl groups can be further substituted by replacing one or more hydrogen atoms with alternative non-hydrogen groups. These include, but are not limited to, halo, hydroxy, mercapto, amino, carboxy, cyano and carbamoyl.

As used herein, the term "halogen" refers to F, Cl, Br, and I.

As used herein, "heteroalkyl" includes both branched and straight-chain saturated aliphatic hydrocarbon groups having the specified number of carbon atoms and at least 1 heteroatom within the chain or branch.

As used herein, "heterocycle" or "heterocyclyl" as used herein is intended to mean a 5- to 10-membered nonaromatic ring containing from 1 to 4 heteroatoms selected from the group consisting of O, N and S, and includes bicyclic groups. "Heterocyclyl" therefore includes, but is not limited to the following: imidazolyl, piperazinyl, piperidinyl, pyrrolidinyl, morpholinyl, thiomorpholinyl, tetrahydropyranyl, dihydropiperidinyl, tetrahydrothiophenyl and the like. If the heterocycle contains a nitrogen, it is understood that the corresponding N-oxides thereof are also encompassed by this definition.

As sued herein, "cycloalkyl" shall mean cyclic rings of alkanes of three to eight total carbon atoms, or any number within this range (i.e., cyclopropyl, cyclobutyl, cyclopentyl, cyclohexyl, cycloheptyl or cyclooctyl).

As used herein, "monocycle" includes any stable polyatomic carbon ring of up to 10 atoms and may be unsubstituted or substituted. Examples of such non-aromatic monocycle elements include but are not limited to: cyclobutyl, cyclopentyl, cyclohexyl, and cycloheptyl. Examples of such aromatic monocycle elements include but are not limited to: phenyl.

As used herein, "bicycle" includes any stable polyatomic carbon ring of up to 10 atoms that is fused to a polyatomic carbon ring of up to 10 atoms with each ring being independently unsubstituted or substituted. Examples of such non-aromatic bicycle elements include but are not limited to: decahydronaphthalene. Examples of such aromatic bicycle elements include but are not limited to: naphthalene.

The term "ester" is intended to a mean an organic compound containing the R—O—CO—R' group.

The term "amide" is intended to a mean an organic compound containing the R—CO—NH—R' or R—CO—N—R'R" group.

The term "phenyl" is intended to mean an aromatic six membered ring containing six carbons and five hydrogens.

The term "benzyl" is intended to mean a —CH$_2$R$_1$ group wherein the R$_1$ is a phenyl group.

The term "substitution", "substituted" and "substituent" refers to a functional group as described above in which one or more bonds to a hydrogen atom contained therein are replaced by a bond to non-hydrogen or non-carbon atoms, provided that normal valencies are maintained and that the substitution results in a stable compound. Substituted groups also include groups in which one or more bonds to a carbon(s) or hydrogen(s) atom are replaced by one or more bonds, including double or triple bonds, to a heteroatom. Examples of substituent groups include the functional groups described above, and halogens (i.e., F, Cl, Br, and I); alkyl groups, such as methyl, ethyl, n-propyl, isopropryl, n-butyl, tert-butyl, and trifluoromethyl; hydroxyl; alkoxy groups, such as methoxy, ethoxy, n-propoxy, and iso-propoxy; aryloxy groups, such as phenoxy; arylalkyloxy, such as benzyloxy(phenylmethoxy) and p-trifluoromethyl-benzyloxy(4-trifluoromethylphenylmethoxy); heteroaryloxy groups; sulfonyl groups, such as trifluoromethanesulfonyl, methanesulfonyl, and p-toluenesulfonyl; nitro, nitrosyl; mercapto; sulfanyl groups, such as methylsulfanyl, ethylsulfanyl and propylsulfanyl; cyano; amino groups, such as amino, methylamino, dimethylamino, ethylamino, and diethylamino; and carboxyl. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

As used herein, "nucleosides" refers to glycosylamines consisting of a nucleobase bound to a ribose or deoxyribose sugar via a beta-glycosidic linkage. Such "nucleosides" may be naturally occurring or synthetic. Examples of such nucleosides are, but not limited to, 5-fluorocytidine and cytarabine.

As used herein, "dexoynucleosides" refers to nucleosides with at least one less oxygen atom. Such "deoxynucleosides" may be naturally occurring or synthetic. Examples of such deoxynucleosides are, but not limited to, 5'-deoxy-5-fluorouridine and 2'-deoxy-5-fluorocytidine.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

In choosing the compounds of the present invention, one of ordinary skill in the art will recognize that the various substituents, i.e. $R_1$, $R_2$, etc. are to be chosen in conformity with well-known principles of chemical structure connectivity.

The various R groups attached to the aromatic rings of the compounds disclosed herein may be added to the rings by standard procedures, for example those set forth in Advanced Organic Chemistry: Part B: Reaction and Synthesis, Francis Carey and Richard Sundberg, (Springer) 5th ed. Edition. (2007), the content of which is hereby incorporated by reference.

The compounds used in the method of the present invention may be prepared by techniques well known in organic synthesis and familiar to a practitioner ordinarily skilled in the art. However, these may not be the only means by which to synthesize or obtain the desired compounds.

The compounds used in the method of the present invention may be prepared by techniques described in Vogel's Textbook of Practical Organic Chemistry, A. I. Vogel, A. R. Tatchell, B. S. Furnis, A. J. Hannaford, P. W. G. Smith, (Prentice Hall) 5$^{th}$ Edition (1996), March's Advanced Organic Chemistry: Reactions, Mechanisms, and Structure, Michael B. Smith, Jerry March, (Wiley-Interscience) 5$^{th}$ Edition (2007), and references therein, which are incorporated by reference herein. However, these may not be the only means by which to synthesize or obtain the desired compounds.

Another aspect of the invention comprises a compound used in the method of the present invention as a pharmaceutical composition.

In some embodiments, a pharmaceutical composition comprising the compound of the present invention and a pharmaceutically acceptable carrier.

As used herein, the term "pharmaceutically active agent" means any substance or compound suitable for administration to a subject and furnishes biological activity or other direct effect in the treatment, cure, mitigation, diagnosis, or prevention of disease, or affects the structure or any function of the subject.

Pharmaceutically active agents include, but are not limited to, substances and compounds described in the Physicians' Desk Reference (PDR Network, LLC; 64th edition; Nov. 15, 2009) and "Approved Drug Products with Therapeutic Equivalence Evaluations" (U.S. Department Of Health And Human Services, 30$^{th}$ edition, 2010), which are hereby incorporated by reference. Pharmaceutically active agents which have pendant carboxylic acid groups may be modified in accordance with the present invention using standard esterification reactions and methods readily available and known to those having ordinary skill in the art of chemical synthesis. Where a pharmaceutically active agent does not possess a carboxylic acid group, the ordinarily skilled artisan will be able to design and incorporate a carboxylic acid group into the pharmaceutically active agent where esterification may subsequently be carried out so long as the modification does not interfere with the pharmaceutically active agent's biological activity or effect.

The compounds used in the method of the present invention may be in a salt form. As used herein, a "salt" is a salt of the instant compounds which has been modified by making acid or base salts of the compounds. In the case of compounds used to treat an infection or disease caused by a pathogen, the salt is pharmaceutically acceptable. Examples of pharmaceutically acceptable salts include, but are not limited to, mineral or organic acid salts of basic residues such as amines; alkali or organic salts of acidic residues such as phenols. The salts can be made using an organic or inorganic acid. Such acid salts are chlorides, bromides, sulfates, nitrates, phosphates, sulfonates, formates, tartrates, maleates, malates, citrates, benzoates, salicylates, ascorbates, and the like. Phenolate salts are the alkaline earth metal salts, sodium, potassium or lithium. The term "pharmaceutically acceptable salt" in this respect, refers to the relatively non-toxic, inorganic and organic acid or base addition salts of compounds of the present invention. These salts can be prepared in situ during the final isolation and purification of the compounds of the invention, or by separately reacting a purified compound of the invention in its free base or free acid form with a suitable organic or inorganic acid or base, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", *J. Pharm. Sci.* 66:1-19).

As used herein, "treating" means preventing, slowing, halting, or reversing the progression of a disease or infection. Treating may also mean improving one or more symptoms of a disease or infection.

The compounds used in the method of the present invention may be administered in various forms, including those detailed herein. The treatment with the compound may be a component of a combination therapy or an adjunct therapy, i.e. the subject or patient in need of the drug is treated or given another drug for the disease in conjunction with one or more of the instant compounds. This combination therapy can be sequential therapy where the patient is treated first with one drug and then the other or the two drugs are given simultaneously. These can be administered independently by the same route or by two or more different routes of administration depending on the dosage forms employed.

As used herein, a "pharmaceutically acceptable carrier" is a pharmaceutically acceptable solvent, suspending agent or vehicle, for delivering the instant compounds to the animal or human. The carrier may be liquid or solid and is selected with the planned manner of administration in mind. Liposomes are also a pharmaceutically acceptable carrier.

The dosage of the compounds administered in treatment will vary depending upon factors such as the pharmacodynamic characteristics of a specific chemotherapeutic agent and its mode and route of administration; the age, sex, metabolic rate, absorptive efficiency, health and weight of the recipient; the nature and extent of the symptoms; the kind of concurrent treatment being administered; the frequency of treatment with; and the desired therapeutic effect.

A dosage unit of the compounds used in the method of the present invention may comprise a single compound or mixtures thereof with additional antibacterial agents. The compounds can be administered in oral dosage forms as tablets, capsules, pills, powders, granules, elixirs, tinctures, suspensions, syrups, and emulsions. The compounds may also be administered in intravenous (bolus or infusion), intraperitoneal, subcutaneous, or intramuscular form, or introduced directly, e.g. by injection, topical application, or other methods, into or onto a site of infection, all using dosage forms well known to those of ordinary skill in the pharmaceutical arts.

The compounds used in the method of the present invention can be administered in admixture with suitable pharmaceutical diluents, extenders, excipients, or carriers (collectively referred to herein as a pharmaceutically acceptable carrier) suitably selected with respect to the intended form of administration and as consistent with conventional pharmaceutical practices. The unit will be in a form suitable for oral, rectal, topical, intravenous or direct injection or parenteral administration. The compounds can be administered alone or mixed with a pharmaceutically acceptable carrier. This carrier can be a solid or liquid, and the type of carrier is generally chosen based on the type of administration being used. The active agent can be co-administered in the form of a tablet or capsule, liposome, as an agglomerated powder or in a liquid form. Examples of suitable solid carriers include lactose, sucrose, gelatin and agar. Capsule or tablets can be easily formulated and can be made easy to swallow or chew; other solid forms include granules, and bulk powders. Tablets may contain suitable binders, lubricants, diluents, disintegrating agents, coloring agents, flavoring agents, flow-inducing agents, and melting agents. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Oral dosage forms optionally contain flavorants and coloring agents. Parenteral and intravenous forms may also include minerals and other materials to make them compatible with the type of injection or delivery system chosen.

Techniques and compositions for making dosage forms useful in the present invention are described in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol. 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modem Pharmaceutics Drugs and the Pharmaceutical Sciences, Vol 40 (Gilbert S. Banker, Christopher T. Rhodes, Eds.). All of the aforementioned publications are incorporated by reference herein.

Tablets may contain suitable binders, lubricants, disintegrating agents, coloring agents, flavoring agents, flow-inducing agents, and melting agents. For instance, for oral administration in the dosage unit form of a tablet or capsule, the active drug component can be combined with an oral, non-toxic, pharmaceutically acceptable, inert carrier such as lactose, gelatin, agar, starch, sucrose, glucose, methyl cellulose, magnesium stearate, dicalcium phosphate, calcium sulfate, mannitol, sorbitol and the like. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds used in the method of the present invention may also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines. The compounds may be administered as components of tissue-targeted emulsions.

The compounds used in the method of the present invention may also be coupled to soluble polymers as targetable drug carriers or as a prodrug. Such polymers include polyvinylpyrrolidone, pyran copolymer, polyhydroxylpropylmethacrylamide-phenol, polyhydroxyethylasparta-midephenol, or polyethyleneoxide-polylysine substituted with palmitoyl residues. Furthermore, the compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Gelatin capsules may contain the active ingredient compounds and powdered carriers, such as lactose, starch, cellulose derivatives, magnesium stearate, stearic acid, and the like. Similar diluents can be used to make compressed tablets. Both tablets and capsules can be manufactured as immediate release products or as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

For oral administration in liquid dosage form, the oral drug components are combined with any oral, non-toxic, pharmaceutically acceptable inert carrier such as ethanol, glycerol, water, and the like. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents.

Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol. Suitable pharmaceutical carriers are described in Remington's Pharmaceutical Sciences, Mack Publishing Company, a standard reference text in this field.

The compounds used in the method of the present invention may also be administered in intranasal form via use of suitable intranasal vehicles, or via transdermal routes, using those forms of transdermal skin patches well known to those of ordinary skill in that art. To be administered in the form of a transdermal delivery system, the dosage administration will generally be continuous rather than intermittent throughout the dosage regimen.

Parenteral and intravenous forms may also include minerals and other materials to make them compatible with the type of injection or delivery system chosen.

The compounds and compositions of the present invention can be administered in oral dosage forms as tablets, capsules, pills, powders, granules, elixirs, tinctures, suspensions, syrups, and emulsions. The compounds may also be administered in intravenous (bolus or infusion), intraperitoneal, subcutaneous, or intramuscular form, or introduced directly, e.g. by topical administration, injection or other methods, to the afflicted area, such as a wound, including ulcers of the skin, all using dosage forms well known to those of ordinary skill in the pharmaceutical arts.

Specific examples of pharmaceutical acceptable carriers and excipients that may be used to formulate oral dosage forms of the present invention are described in U.S. Pat. No. 3,903,297 to Robert, issued Sep. 2, 1975. Techniques and compositions for making dosage forms useful in the present invention are described-in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modem Pharmaceutics Drugs and the Pharmaceutical Sciences, Vol 40 (Gilbert S. Banker, Christopher T. Rhodes, Eds.). All of the aforementioned publications are incorporated by reference herein.

The term "prodrug" as used herein refers to any compound that when administered to a biological system generates the compound of the invention, as a result of spontaneous chemical reaction(s), enzyme catalyzed chemical reaction(s), photolysis, and/or metabolic chemical reaction(s). A prodrug is thus a covalently modified analog or latent form of a compound of the invention.

The active ingredient can be administered orally in solid dosage forms, such as capsules, tablets, powders, and chewing gum; or in liquid dosage forms, such as elixirs, syrups, and suspensions, including, but not limited to, mouthwash and toothpaste. It can also be administered parentally, in sterile liquid dosage forms.

Solid dosage forms, such as capsules and tablets, may be enteric coated to prevent release of the active ingredient compounds before they reach the small intestine. Materials that may be used as enteric coatings include, but are not limited to, sugars, fatty acids, waxes, shellac, cellulose acetate phthalate (CAP), methyl acrylate-methacrylic acid copolymers, cellulose acetate succinate, hydroxy propyl methyl cellulose phthalate, hydroxy propyl methyl cellulose acetate succinate (hypromellose acetate succinate), polyvinyl acetate phthalate (PVAP), and methyl methacrylate-methacrylic acid copolymers.

The compounds and compositions of the invention can be coated onto stents for temporary or permanent implantation into the cardiovascular system of a subject.

The compounds of the present invention can be synthesized according to general Schemes. Variations on the following general synthetic methods will be readily apparent to those of ordinary skill in the art and are deemed to be within the scope of the present invention.

Each embodiment disclosed herein is contemplated as being applicable to each of the other disclosed embodiments. Thus, all combinations of the various elements described herein are within the scope of the invention.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

Materials and Methods

Those having ordinary skill in the art of organic synthesis will appreciate that modifications to general procedures and synthetic routes contained in this application can be used to yield additional derivatives and structurally diverse compounds. Suitable organic transformations are described in in March's Advanced Organic Chemistry: Reactions, Mechanisms, and Structure (Wiley-Interscience; 6th edition, 2007), the content of which is hereby incorporated by reference.

α-Boc-Lys(ε-Ac)-OH and puromycin dihydrochloride were purchased from Bachem and TOKU-E, respectively. 1-ethyl-3-(3-dimethylaminopropyl) carbodiimide hydrochloride (EDC.HCl) and 1-hydroxybenzotriazole (HOBt.H2O) were purchased from Advanced Chem Tech. Dichloromethane (DCM) and dimethylformamide (DMF) were obtained from EMD chemical. DMF was dried and purified by solvent pushstill (SG water USA LLC, Nashua, N.H.). $^1$H NMR data are reported as chemical shift in ppm (multiplicity, coupling constant in Hz, integration, and tentative assignment. $^{13}$C NMR data are reported as chemical shift in ppm (tentative assignment). Assignments are based on expected chemical shifts, multiplicities, and coupling constants.

Cell Culture

Colon cancer (Caco-2, COCA-10, HCA-7, HT29, HCT116), normal colon CCD841-CoN, pancreatic cancer (MiaPaca-2, BXPC-3), liver cancer HepG2, and cervical cancer HeLa and normal mouse mammary epithelial Eph4 cell lines were maintained in Iscove's Modified Dulbecco's Medium (IMDM, Invitrogen) supplemented with 10% fetal bovine serum and 100 U/ml penicillin/streptomycin at 37° C. with 5% $CO_2$ atmosphere.

Enzymatic Assays

Tissue culture based standard HDAC assays were performed by commercially available fluorimetric HDAC assay kit (SensoLyte, AnaSpec) according to the manufacturer's instruction with modification of using 25 μM Boc-Lys(Ac)-AMC (Bachem) as substrate and measuring parameter (Ex/Em=355 nm/460 nm) for AMC. Basically, HDAC substrate 25 μM Boc-Lys(Ac)-AMC [either with DMSO or 1 μM TSA (Sigma)] was applied to the overnight culture seeded from 6×104 cells in 100 μl medium in 96-well tissue culture plates, followed by 2 to 3 h incubation at 37° C. with 5% $CO_2$ atmosphere. Then the deacetylation reaction was terminated by addition of HDAC developer solution containing cell lysis buffer and trypsin reagents. After 15 m incubation at room temperature, the fluorescent signal of AMC was measured by SpectraMax M5 microplate reader (Molecular Devices) at Ex/Em=355 nm/460 nm. Live cell lysyl endopeptidase assay was performed by applying the substrate 25 μM Boc-Lys-AMC (Bachem) [either with DMSO or 100 μM Z-FY-CHO (EMD)] to the overnight culture seeded from 6×104 cells in 100 μl medium in 96-well tissue culture plates, followed by 20 h incubation at 37° C. with 5% $CO_2$ atmosphere, then the fluorescent signal of AMC was measured. Live cell enzymatic assay using Boc-Lys(Ac)-AMC was performed by applying the substrate 25 μM Boc-Lys (Ac)-AMC (either with DMSO, 1 μM TSA or 100 μM Z-FY-CHO) to the overnight culture seeded from 6×104 cells in 100 μl medium in 96-well tissue culture plates, followed by 20 h incubation at 37° C. with 5% $CO_2$ atmosphere, then the fluorescent signal of AMC was measured. Experiments were repeated at least three times.

Cell Viability Assays

Cell number was determined by cell counting using improved Neubauer hemacytometer. Cell viability was calculated as the number of viable cells divided by the total number of cells using Trypan Blue Stain (Invitrogen) to distinguish non-viable cells. Data were obtained from duplicated samples with quadruplicate measurements. MTS based cell viability assay was performed using CellTiter 96 Aqueous Cell Proliferation Assay (Promega) according to the manufacturer's instruction. Either 1 μl of DMSO alone or variable concentrations of BKAc-Puro or Puro in DMSO were added to the cell lines seeded at 5×104 cells per well in 96-well tissue culture plates in 100 μl of the growth medium, followed by 3-5 d incubation at 37° C. with 5% CO2 atmosphere. Then 20 μl of the MTS reagent was added to each well. After additional 2-3 h incubation, the absorbance of the formazan at 490 nm was measured by the microplate reader. Percent cell viability was expressed relative to the wells containing cells treated with DMSO alone. Data were obtained from triplicate measurements. The $IC_{50}$ values (the concentration resulting in 50% inhibition) of BKAc-Puro were determined by dose-response curve analysis (GraphPad Prism software). Experiments were repeated at least three times. Determination of non-viable cells using PI staining was performed by adding 1 μg/ml of PI solution (Sigma) to the cell culture, prior to the examination under fluorescence microscopy (Axiovert 3, Carl Zeiss) through a×32 objective equipped with a digital imaging processor (Infinity 3, Lumenera).

In Vivo Assay

To assess the in vivo efficacy of the compounds, a BxPC3 xenograft model is used as an established evaluation method for the anticancer drugs against pancreatic cancer (Kano, M. R. et al. 2007; O'Toole, J. M. et al. 2006). The cells are transfected with expression plasmids for GFP and selected for GFP expression in order to mark the tumor cells. The growth inhibitory effects of the compounds on size-matched BxPC3 xenografts are examined by subcutaneous implantation of BxPC3 cells into nude mice. BxPC3 cells are injected subcutaneously and allowed to grow for 2-3 weeks to reach proliferative phase before initiation of drug administration. Mice (5 animals per group) are treated with the vehicle (PBS), the various prodrugs, or 5-FU by intraperitoneal administration every 3 days for a total of 4 doses. The prodrugs are expected to have lower toxicity than the parental 5-FU, thus dose ranges that have been established by others for 5-FU are used (Overholser, J. P. et al. 2000). Then, the mice are imaged over a 3 week period using the Maestro small animal imaging system. This scanner captures tumor growth in the mice by detection of increasing area and intensity of green fluorescence emitted from the GFP. Xenograft tumors are measured externally every second day until day 16-21, and tumor volumes are approximated by using the equation vol=(a×b$^2$)/2, where vol, a, and b represent volume, the length of the major axis, and the length of the minor axis, respectively. Relative tumor volume is calculated by dividing tumor volume by that on day 0 (the day of treatment initiation). The weight of the mice is checked to monitor unfavorable effects by the compounds being tested and upon any indication of distress the mice is humanely euthanized. Statistical significance of the data is evaluated by performing one-way ANOVA with post hoc Turkey's test to compare means (GraphPad Prism software). The efficacy of the compounds is further evaluated in a similar manner by using other pancreatic adenocarcinoma cell lines CFPac-1 and MiaPaCa-2 and the PDA lines in which HDAC3 levels have been reduced.

To assess the in vivo efficacy of the compounds, mouse xenograft model using HCT116 colon cancer cells is used as an established evaluation method for the anticancer drugs against cancer (Cao, Z. A. et al. 2006). The growth inhibitory effects of the compounds on size-matched xenografts are examined by subcutaneous implantation of HCT116 cells into nude mice. HCT116 cells are injected subcutaneously and allowed to develop palpable tumors (50-150 mm$^3$) before initiation of drug administration. Mice (5-10 animals per group) are treated with the vehicle (DMSO or PBS) or the prodrugs by intraperitoneal administration. Dose ranges are determined by the dose escalation studies of the prodrugs. Tumor volumes are approximated by using the equation vol=(a×b$^2$)/2, where vol, a, and b represent volume, the length of the major axis, and the length of the minor axis, respectively. Relative tumor volume is calculated by dividing tumor volume by that on day 0 (the day of treatment initiation). The weight of the mice is checked to monitor unfavorable effects by the compounds being tested and upon any indication of distress the mice is humanely euthanized. Statistical significance of the data is evaluated by performing one-way ANOVA with post hoc Turkey's test to compare means (GraphPad Prism software). The efficacy of the compounds is further evaluated in a similar manner by using other cancer cell lines.

Athymic mice (NCr, female, age 6 weeks, Taconic) were subcutaneously injected with 5×10$^5$ cells (HCT116 or HT29) into the lower flank, then treatment was initiated when small palpable tumors had developed (>3 mm in diameter). Either Boc-KAc-Puro in 150 mM HCl (pH 2 adjusted by NaOH) or acidified saline (pH 2) as control was daily administered intraperitoneally for 10 d. Tumor volumes and body weight were monitored daily. Tumor volume was estimated by the equation vol=(a×b$^2$)/2, where vol, a, and b represent volume (mm3), the length of the major axis (mm), and the length of the minor axis (mm), respectively. Data were expressed as mean±s.d.

Statistical Analyses.

For the in vivo experiments, a two-tailed student's t test was used to calculate statistical significance of the observed differences. P<0.05 was considered statistically significant.

Immunological Detection of Puro-Labeled Proteins.

Cultured cells or tissue samples were sonicated in RIPA lysis buffer (1% NP-40, 0.1% SDS, 50 mM Tris-HCl pH 7.4, 150 mM NaCl, 0.5% sodium deoxycholate, 1 mM EDTA) supplemented with PMSF and protease inhibitor cocktail (Roche) on ice followed by clarification. Protein lysates were separated on sodium dodecyl sulfate-polyacrylamide gels and transferred onto nitrocellulose membranes (Whatman). The primary antibodies used were anti-puromycin (3RH11, KeraFAST) and anti-α-tubulin (Sigma-Aldrich). Proteins of interest were detected with anti-mouse secondary antibody by chemiluminescence (ECL Kit, GE Healthcare Life Sciences).

Example 1. Levels of HDAC in Cancer Cells

To test the hypothesis that cancer cells have elevated levels of HDAC activity, HDAC activity was measured in a panel of human cancer cell lines including colon cancer (Caco-2, COGA-10, HCA-7, HT29, HCT116), pancreatic cancer (BXPC-3, MiaPaca-2), liver cancer (HepG2), and cervical cancer (HeLa), as well as non-tumorigenic human colon epithelial cells (CCD841-CoN) and normal mouse mammary epithelial cells (Eph4) (Mariadason, J. M. et al. 2001; Wegener, D. et al. 2003) (FIG. 1).

Using a standard fluorometric assay, marked high levels of HDAC activity was observed in all malignant cell lines tested but, in clear contrast, low levels in less-tumorigenic and normal cell lines (Caco-2, CCD841-CoN, Ehp4). The specificity of the HDAC activity was confirmed by a HDAC inhibitor Trichostatin A (TSA) (Yoshida, M. et al. 1990). Although Caco-2 cells originated from human colon adenocarcinoma, these cells are known to be less-tumorigenic and behave like normal, differentiated enterocytes in vivo when cultured as confluent cells (Mariadason, J. M. et al. 2001). These results supported our approach to target HDAC activity for cancer therapy and lead us to explore the possibility of designing new anticancer agents by incorporating chemical HDAC substrates into cytotoxic drugs so that their cytotoxicity can be selectively activated in cancer cells in a HDAC dependent manner.

Example 2. Boc-Lys(Ac)-AMC

Typical fluorogenic substrates for class I HDACs are comprised of an s-acetylated lysine residue (alone or in short peptides) coupled to a fluorophor moiety AMC (7-amino-4-methylcoumarin) such as cell-permeable Boc-Lys(Ac)-AMC (Wegener, D. et al. 2003; Bonfils, C. et al. 2008). The standard HDAC assay is based on the two-step conversion of the substrate: 1) HDAC-dependent deacetylation of ε-acetylated lysine, 2) protease-dependent cleavage of Lys-AMC amide bond and subsequent release of free fluorophor AMC, which fluoresces (Wegener, D. et al. 2003). In the tissue culture based assays, the second step is normally performed following cell lysis by addition of excessive amounts of trypsin, which only recognizes and processes deacetylated form of lysine. Given that the Lys-AMC amide bond can be cleaved by other endogenous proteases commonly associated with cancer cells such as lysosomal proteases (Weissleder, R. et al. 1999), it was hypothesized that the second step can occur in live cells without cell lysis and trypsin treatment.

Figure 2:
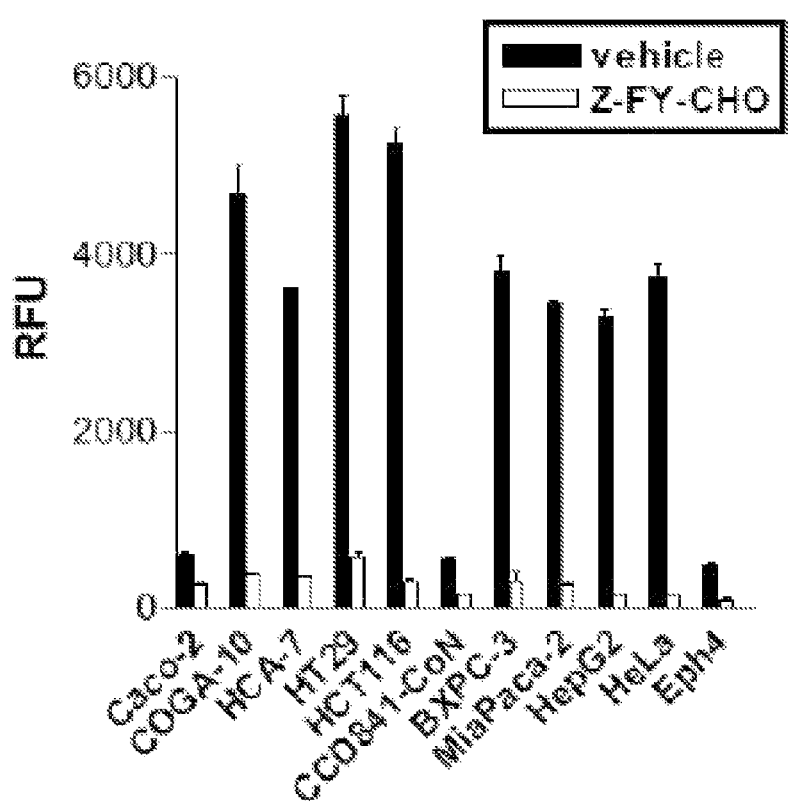
FIG. 2. Comparative live cell lysyl endopeptidase activity of the same cell lines as in FIG. 1 using substrate Boc-Lys-AMC either with vehicle control DMSO or Z-FY-CHO (100 μM). Data represent mean values of triplicate measurements±s.d. RFU, relative fluorescent units.
Figure 3:
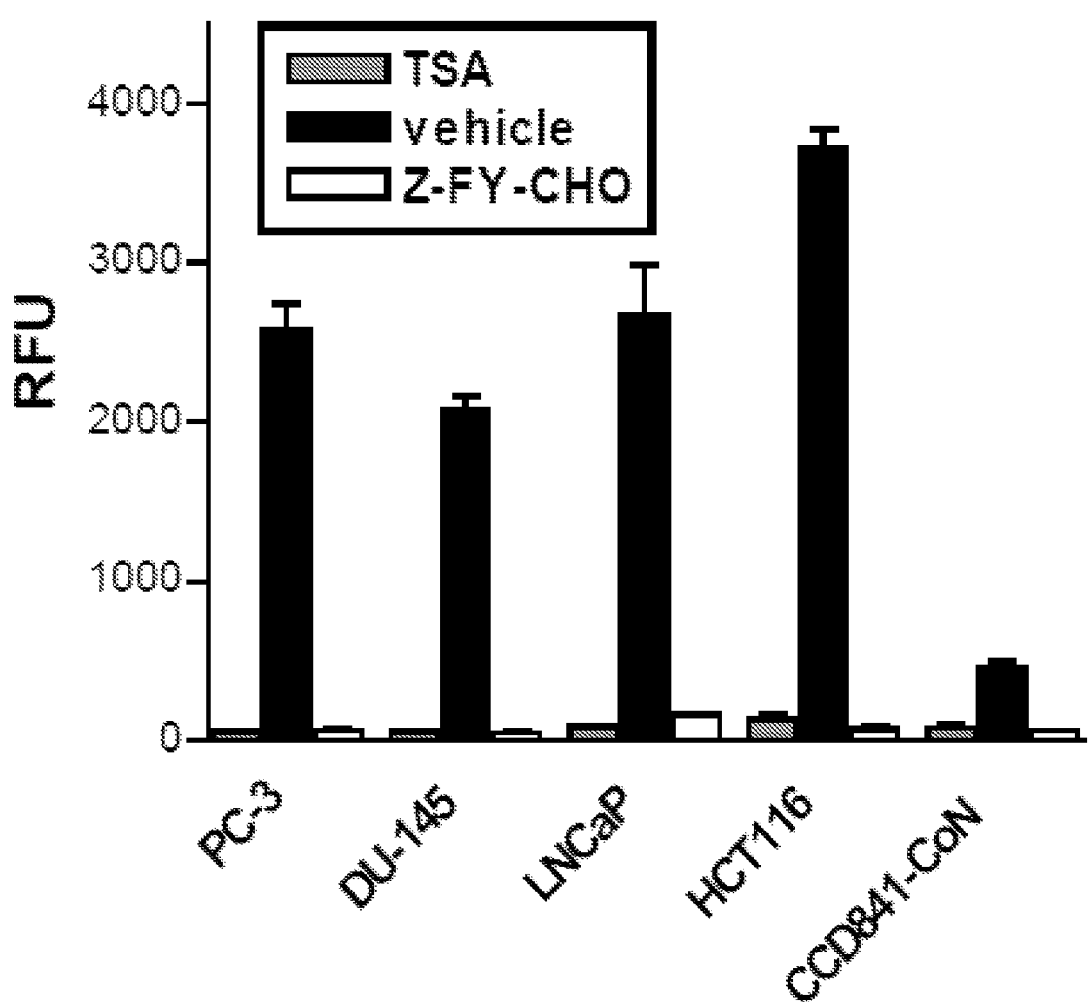
FIG. 3. Prostate cancer cells exhibit high enzymatic activity to convert Boc-Lys(Ac)-AMC releasing AMC in live cells. Comparative live cell enzymatic activity. Prostate cancer (PC-3, DU-145, and LNCaP), colon cancer (HCT116 as a positive control sensitive to the drug), and normal colon (CCD841-CoN as a negative control) cells were analyzed using substrate Boc-Lys(Ac)-AMC either with vehicle control DMSO, TSA (1 μM) or Z-FY-CHO (100 μM). Data represent mean values of triplicate measurements±s.d. RFU, relative fluorescent units.

To test this possibility, levels of lysyl endopeptidase activity in live cells using Boc-Lys-AMC as a substrate was assessed. As shown in FIG. 2, the levels of protease activity were much greater in the malignant cells, whereas those in the less-tumorigenic Caco-2, CCD841-CoN and Eph4 cells were only basal, showing striking correlation between elevated HDAC and lysyl endopeptidase activities in the malignant cells. These results prompted identification of the endogenous protease releasing AMC in live cells. Considering the mode of substrate recognition and elevated activity in malignant cells, Z-FY-CHO, a specific inhibitor of lysosomal cysteine protease catepsin L (CTSL), was tested (Gonzalez-Suarez, I. et al. 2011). CTSL is known to play crucial roles at multiple stages of tumor progression and metastasis (Lankelma, J. M. et al 2010; Jedeszko, C. & Sloane, B. F. 2004). Furthermore, there is growing evidence that upregulation of CTSL is a hallmark of metastatic cancers and could be utilized as a prognostic marker (Gonzalez-Suarez, I. et al. 2011; Joyce, J. A. et al. 2004). In all cases tested, the release of AMC was significantly blocked by Z-FY-CHO (FIGS. 2 & 3), indicating that CTSL is responsible for the second step reaction in the live cell assay.

Figure 4:
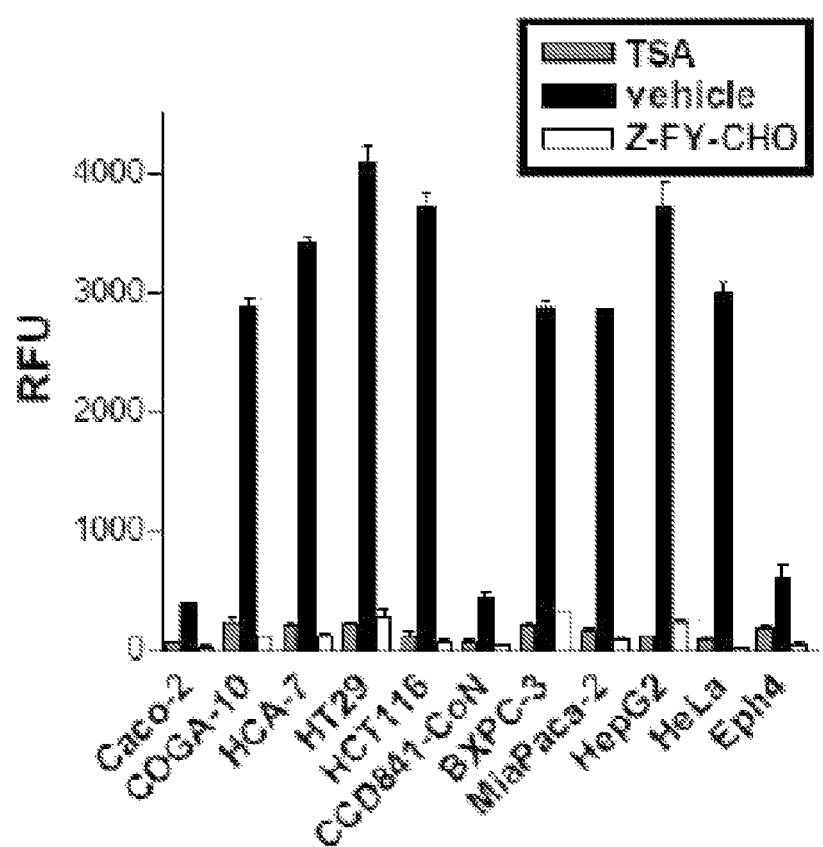
FIG. 4. Comparative live cell enzymatic activity of the same cell lines as in FIG. 1 using substrate Boc-Lys(Ac)-AMC either with vehicle control DMSO, TSA (1 μM) or Z-FY-CHO (100 μM). Data represents mean values of triplicate measurements±s.d. RFU, relative fluorescent units.

To confirm if the two-step conversion of the HDAC substrate seamlessly proceeded in live cells, the levels of released AMC using Boc-Lys(Ac)-AMC was monitored (FIG. 4). Consistent with the levels of HDAC and CTSL activities, selectively higher levels of AMC were detected in all malignant cell lines tested. The observed effects shown in the presence of TSA or Z-FY-CHO confirmed that both HDAC and CTSL activities were required for the release of AMC in live cells (FIG. 4). The data clearly indicated that the HDAC substrate can be selectively processed in live cells, further supporting the approach to create HDAC activity based anticancer agents.

Example 3. Boc-Lys(Ac)-AMC vs. Ac-Arg-Gly-Lys(Ac)-AMC

Commercially available fluorescent compounds were used to measure HDAC activity in cells to obtain important preliminary data. Established substrates for the sensitive fluorogenic assay of class I HDACs are comprised of a short peptide sequences coupled with an s-acetylated lysine residue followed by a fluorophor moiety (Wegener, D. et al 2003). Such substrates include Boc-Lys(Ac)-X and Ac-Arg-Gly-Lys(Ac)-X, where X represents fluorophor moiety such as AMC. The assay was also based on the two-step conversion of the fluorogenic peptide substrate: 1) Intracellular HDAC-dependent deacetylation of ε-acetylated lysil moiety, 2) protease-dependent cleavage of Lys-X amide bond and subsequent release of free fluorophor. The second step required cell lysis followed by addition of excessive amounts of exogenous proteases (commonly trypsin) to the reaction.

Fluorescence measurement was done at $\lambda_{ex}$=390 nm and $\lambda_{em}$=460 nm for AMC. FIG. 4A shows the standard assay using these compounds, which were incubated with cells for various times, in this case 2.5 hr, during which time they were readily taken up by the cells and the endogenous HDAC enzymes deacetylate the lysine residues. Cells were then lysed and the lysates incubated with exogenously added excess trypsin to cleave only those lysine residues that are deacetylated and activate fluorescence. As tumor cells are known to frequently exhibit increased levels of intracellular protease activity, it was postulated that intracellular tumor-associated protease activity would be able to cleave the exposed lysine residue in live cells and release the fluorescent compounds. This live cell reaction would clearly not be indicative of total cellular HDAC activity as it would now also depend on access of the compounds to cellular proteases and also require the proteases to be able to cleave the lysine in its specific context.

Figure 5:
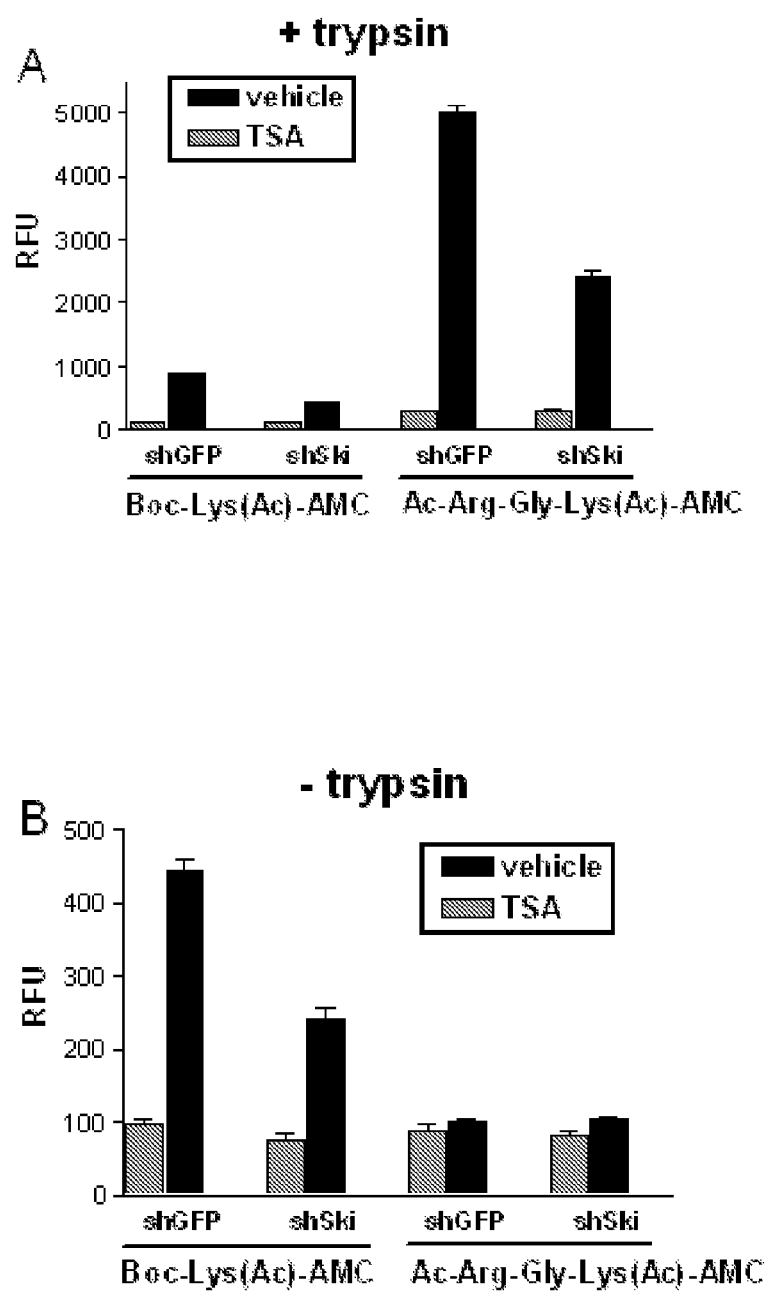
FIG. 5. A. HDAC assay using different substrates in BxPC3 cells (shGFP and shSki). Cells were incubated with Boc-Lys(Ac)-AMC or Ac-Arg-Gly-Lys(Ac)-AMC (25 μM) for 1 hr with DMSO (vehicle) or TSA (1 μM) as indicated, followed by cell lysis and trypsin treatment, and fluorescence measurements. Data represent mean values of triplicate measurements±standard deviation. RFU, relative fluorescent units. B. Similar experiment was done as in A but without cell lysis and trypsin treatment. Cells were incubated with the substrates for 2.5 hr.

Nevertheless if fluorescence was activated it would indicate that the live PDA (Pancreatic ductal adenocarcinoma) cells had the necessary enzymatic activities to activate these compounds and provide key evidence that they should also be able to activate the pro-drugs described above. FIG. 5 shows a comparison of the normal assay (A) in which cells are lysed and then incubated with trypsin with a similar experiment (B) in which live cells were incubated with the same fluorescent compounds. Two substrates were compared, one substrate that just had a single acetylated lysine residue, Boc-Lys(Ac)-AMC, with one that has a three amino acid peptide, Ac-Arg-Gly-Lys(Ac)-AMC. Note the scales on the two graphs differ by a factor of ten. As can be seen in FIG. 5A, both compounds measured total HDAC activity, albeit with differing sensitivities, and again showed that Ski knockdown by shRNA against Ski lowers the HDAC activity. More importantly as shown in FIG. 4B, in which live cells were incubated with the two substrates, the Boc-Lys (Ac)-AMC was activated in a HDAC and Ski-dependent manner to approximately 50% of total HDAC activity, whereas the other substrate was not activated at all. This experiment demonstrated that live PDA cells have the necessary enzymatic activities (HDAC plus proteolytic) to activate acetylated-lysine substrates and that the context of the acetylated-lysine was important for the proteolytic cleavage activation step. This data also indicated that it should be possible to synthesize prodrugs of similar structures that can deliver cytotoxic compounds inside cells whose activation is dependent on intracellular HDAC and protease activities and the drugs can be varied in both payload and peptide side chains to generate maximal tumor specific activity.

To address possible intracellular proteases that may be responsible for the activation of the substrate it was noted that a lysosomal cystein protease cathepsin L has been studied as a tumor associated protease, and it's utility as a prognostic marker has been evaluated for numerous different tumor types including pancreatic cancers (Joyce, J. A. et al. 2004; Von Burstin, J. et al. 2008; Niedergethmann, M. et al. 2004). Thus, a highly specific inhibitor of cathepsin L, Z-FY-CHO was tested in the live cell assay (Pacheco, F. J. et al. 2005). As shown in FIG. 6A, incubation of the cells with the cathepsin L inhibitor completely abrogated the activation of the substrate. Thus, cathepsin L was targeted as a candidate enzyme for the second necessary step in the prodrug activation reaction. This experiment also confirmed that both HDAC and protease activities are required for activation as HDAC inhibition (TSA) and protease inhibition (Z-FY-CHO) completely inhibited activation. In addition, a time course experiment showed that AMC was released linearly over the time (20 hr), while in the presence of TSA, AMC release was inhibited (FIG. 6B), demonstrating that cathepsin L hardly cleaves Boc-Lys(Ac)-AMC even after longer incubation periods.

Example 4. Boc-Lys(Ac)-Puromycin

Synthesis Boc-Lys(Ac)-Puromycin

Figure 7:
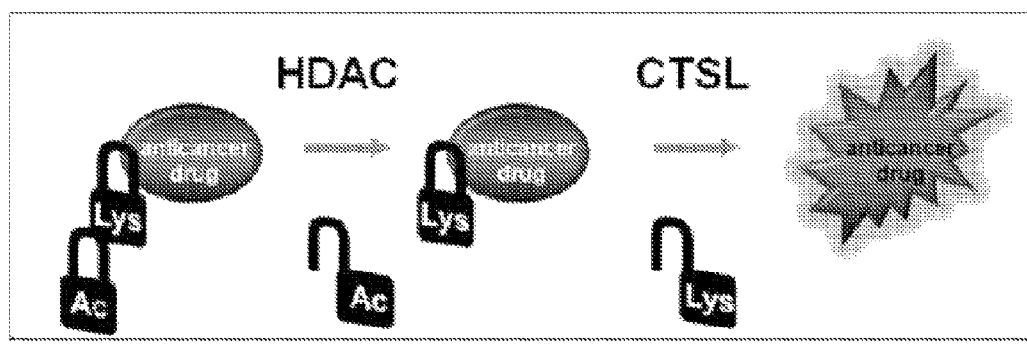
FIG. 7. A scheme of the selective two-step drug activation in cancer cells by HDAC and CTSL.
Figure 8A:
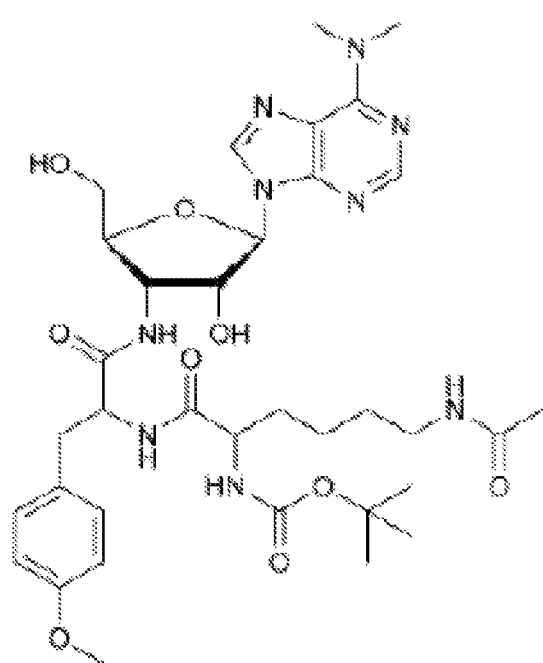
FIG. 8. Boc-Lys(Ac)-Puromycin, Spectral data for Boc-KAc-Puro. (a) $^1$H NMR (500 MHz, DMSO-d6). (b) $^{13}$C NMR (101 MHz, DMSO-d6).
Figure 8B:
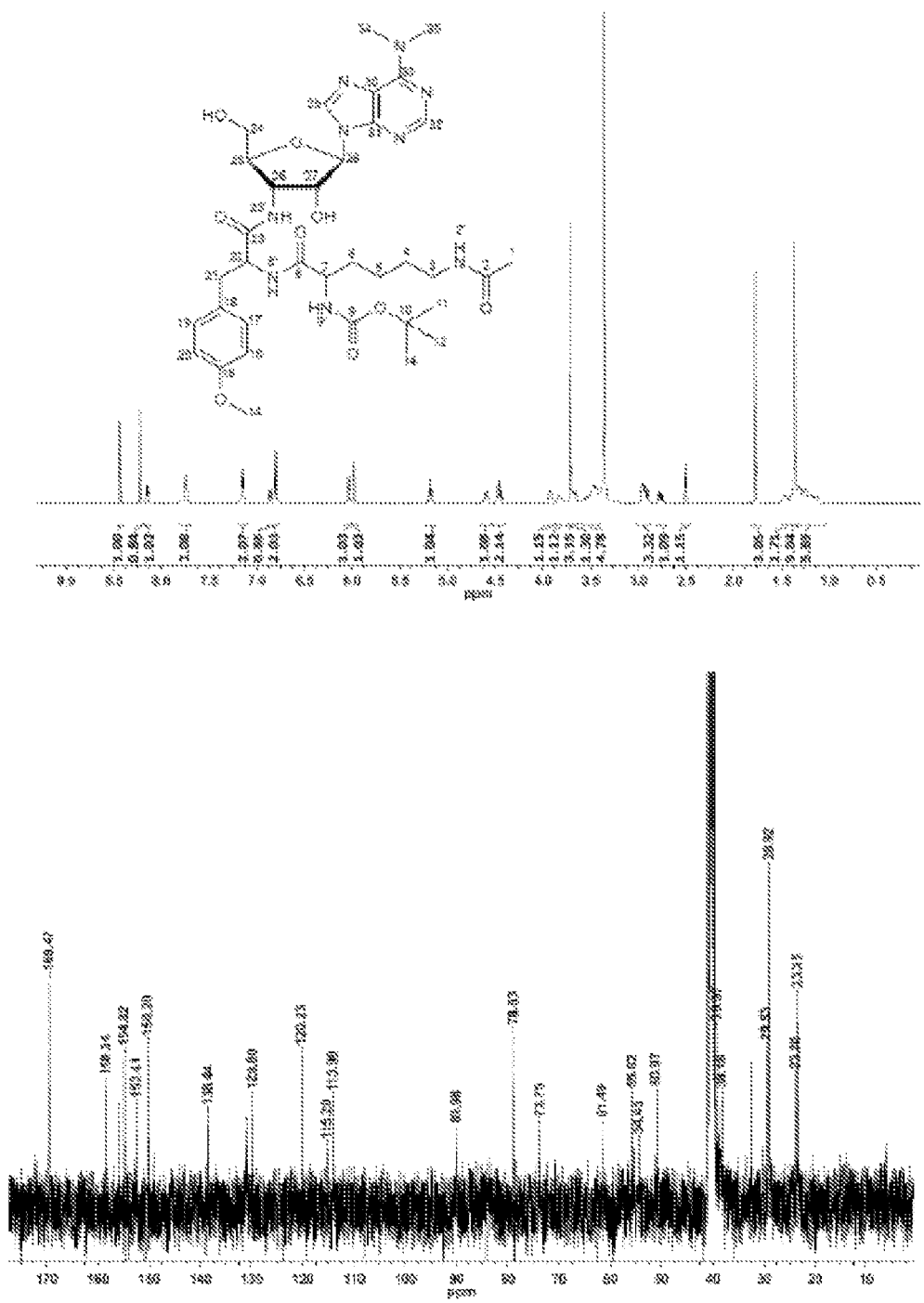

Having established the utility of the HDAC substrate Boc-Lys(Ac)-AMC in live cells, a compound was synthesized by applying the HDAC substrate into cytotoxic drugs (FIG. 7). Among many cytotoxic drugs, puromycin (Pure), an aminonucleoside antibiotic produced by the bacterium Streptomyces alboniger and a potent protein synthesis inhibitor that causes premature termination of growing polypeptide chains on ribosome was selected (Vara, J. A. et al. 1986). Puro is a potent translational inhibitor in both prokaryotic and eukaryotic cells. Resistance to Puro is conferred by the puromycin N-acetyltransferase gene, pac, which is widely used as a selection marker for gene transfer (Vara, J. A. et al. 1986). Given that the cytotoxicity of Puro is completely inactivated by the acetylation of its amino group by the pac gene product, it was reasoned that this antibiotic would be an ideal candidate for the evaluation of the HDAC dependent release of cytotoxicity. Thus, Boc-Lys (Ac)-puromycin (BKAc-Puro) was synthesized by conjugating Boc-Lys(Ac)-OH with the amino group of Puro (FIG. 8).

N-[3'-(α-Amino-p-methoxyhydrocinnamamido)-3'-deoxy-N,N-dimethyldenosinyl]-N-α-(t-butoxycarbonyl)-N-ε-acetyl-L-lysineamide (Boc-Lys(Ac)-Puromycin): A mixture of puromycin dihydrochloride (50 mg, 0.092 mmol), α-Boc-Lys(ε-Ac)-OH (31 mg, 0.11 mmol), EDC.HCl (21 mg, 0.11 mmol), HOBt.H$_2$O (17 mg, 0.11 mmol), and DIEA (N,N-diisopropylethylamine) (18 μL, 0.11 mmol) was stirred in DMF (10 ml) at rt for 18 h. After concentrating the solution under reduced pressure, the residue was dissolved in DCM. The DCM solution was washed with H$_2$O three times, dried over Na$_2$SO$_4$, and concentrated. The crude oil was purified by silica gel column chromatography using a linear gradient from 5 to 10% MeOH in DCM and dried to yield α-Boc-Lys(s-Ac)-Puromycin as a white solid (55 mg, 75% yield): mp: 182-183° C.; $^1$H NMR (500 MHz, DMSO) δ 8.43 (s, 1H, H-29), 8.22 (s, 1H, H-32), 8.15 (d, J=7.7 Hz, 1H, H-8'), 7.74 (d, J=7.1 Hz, 2H, H-2', H-23'), 7.15 (d, J=8.4 Hz, 2H, H-17), 6.86 (d, J=8.3 Hz, 1H, H-9'), 6.80 (d, J=8.6 Hz, 2H, H-16, H-20), 6.03 (d, J=4.6 Hz, 1H, H-28), 5.98 (d, J=2.8 Hz, 1H, H-27), 5.18 (t, J=5.4 Hz, 1H, H-22), 4.60 (dd, J=13.6, 8.1 Hz, 1H, H-7), 4.52-4.39 (m, 2H, H-25, H-26), 3.98-3.76 (m, 2H, H-24), 3.70 (s, 3H, H-14), 3.69-3.40 (m, 6H, H-34, H-35), 3.02-2.86 (m, 3H, H-3, H-21), 2.76 (dd, J=13.7, 8.7 Hz, 1H, H-21), 1.77 (s, 3H, H-1), 1.52-1.38 (m, 2H, H-6), 1.38-1.32 (s, 9H, H-11, H-12, H-13), 1.33-1.05 (m, 6H, H-4, H-5) ppm. $^{13}$C NMR (101 MHz, DMSO) δ 169.5 (C-8, C-23), 158.4 (C-9), 155.8 (C-2), 154.8 (C-33), 152.4 (C-32), 150.2 (C-31), 138.4 (C-29), 138.3 (C-15), 131.0 (C-17, C-19), 129.8 (C-18), 120.2 (C-30), 114.0 (C-16, C-20), 90.0 (C-28), 78.8 (C-10, C-25), 73.8 (C-27), 61.5 (C-24), 55.6 (C-26), 55.3 (C-7), 54.5 (C-22), 51.0 (C-14), 40 ((C-34, C-35, underneath DMSO peak), 39.1 (C-3), 38.2 (C-21), 32.5 (C-6), 29.5 (C-4), 28.9 (C-11, C-12, C-13), 23.7 (C-5), 23.4 (C-1); MS (m/z): [M]$^+$ calcd. for $C_{35}H_{51}N_9O_9$, 742.38; found, 742.47.

Biological Data

Figure 9:
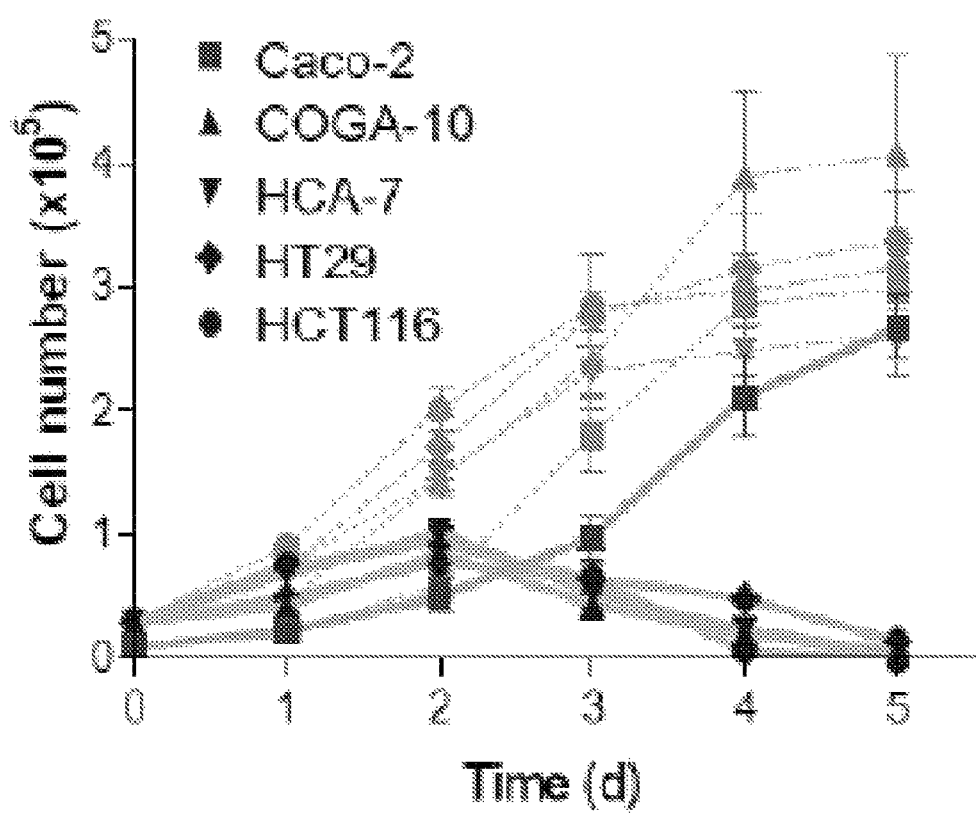
FIG. 9. The colon cancer cell lines were grown for 5 d either with vehicle control DMSO (gray symbols) or 54 μM BKAc-Puro (red and blue symbols), and cell number was determined at the indicated time points.
Figure 10:
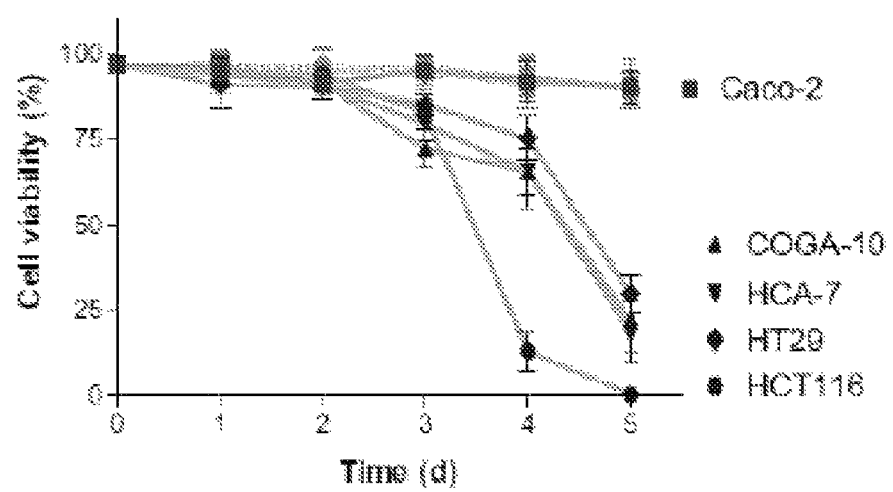
FIG. 10. The cell lines were grown as in FIG. 8, cell viability was determined by trypan blue at the indicated time points, and is presented as the percentage of live cells treated with vehicle control (gray symbols) or BKAc-Puro (red and blue symbols).
Figure 11:
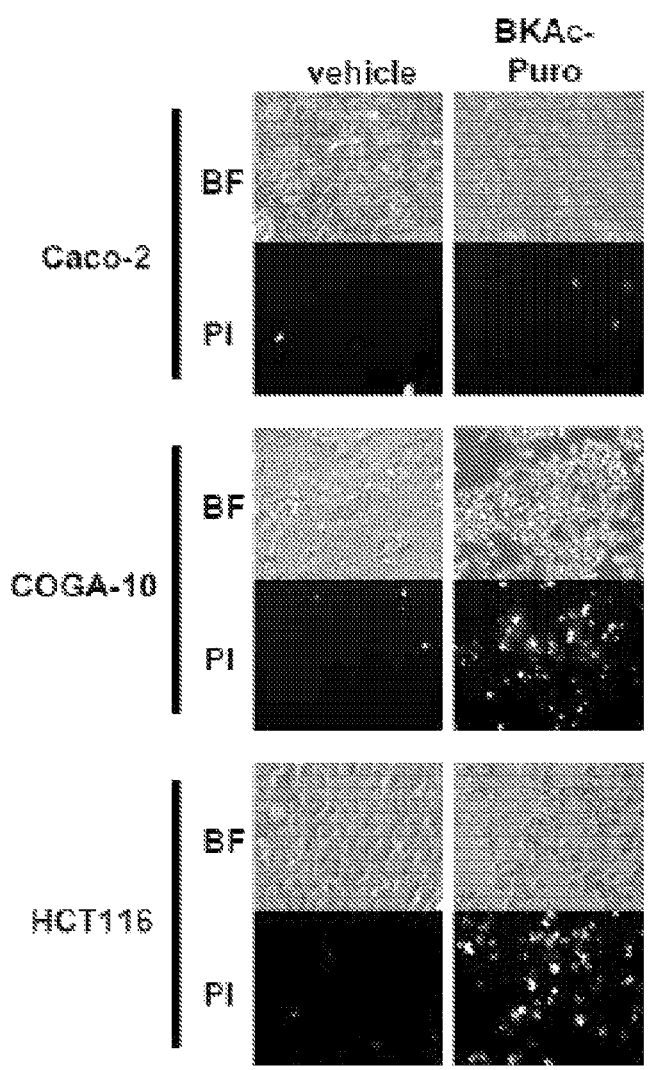
FIG. 11. The cell lines were grown as in FIG. 8, and dead cells were determined after 80 h by PI signal under fluorescent microscope. BF, bright field. PI, fluorescent PI channel.
Figure 12:
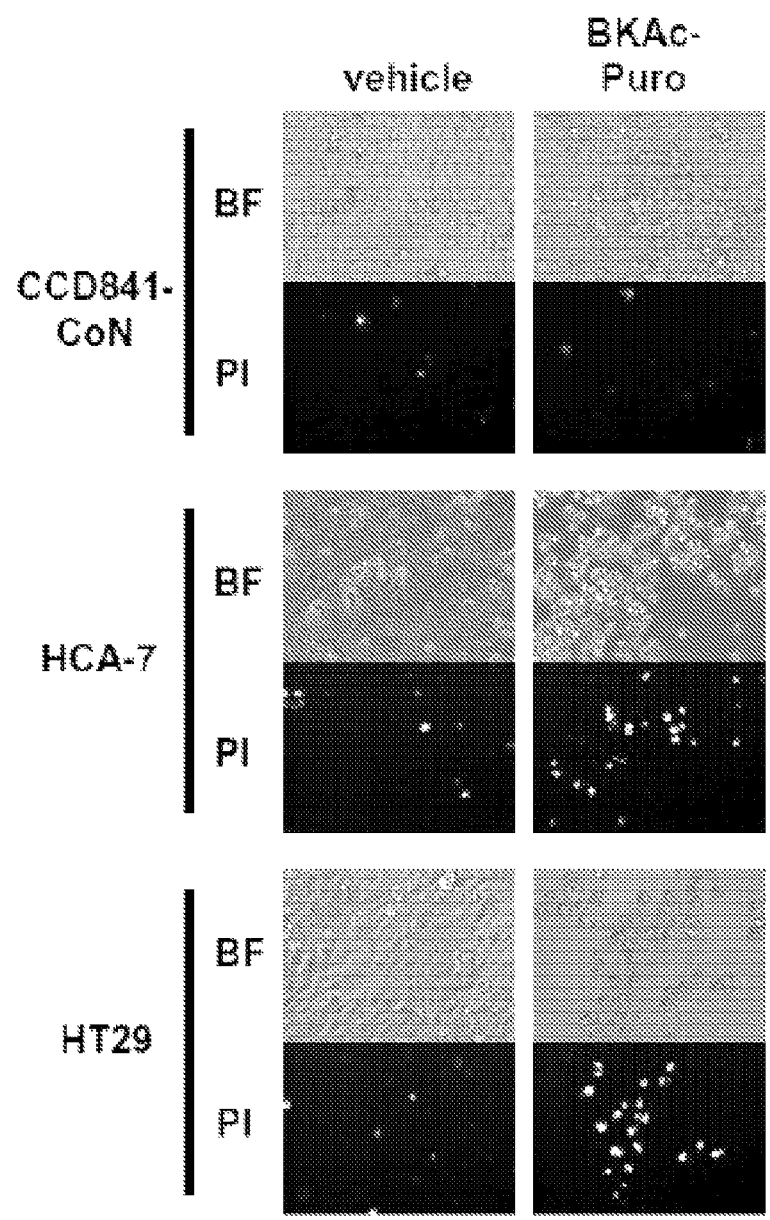
FIG. 12. Selective cytotoxicity by BKAc-Puro. The cell lines were grown and analyzed as in FIG. 10. BF, bright field. PI, fluorescent PI channel.

Anticancer properties of BKAc-Puro in a panel of colon cell lines were assessed. The agent impaired the proliferation of all four malignant cells with high HDAC and CTSL activity (FIG. 9), while in non-malignant Caco-2 cells, it allowed them to proliferate to confluency, showing a noteworthy feature distinguished from the general cytostatic effect on normal cells by most widely used antimetabolite cancer drugs and HDACi (Mark, P. A. & Xu, W. S. 2009). Consistent with the effect on cell proliferation, massive cell death wass detected only in the malignant cells as judged by trypan blue exclusion (FIG. 10), morphological changes under phase contrast and propidium iodide (PI) staining (FIGS. 11-12). The results indicated that the antiproliferative and cytotoxic effects of BKAc-Puro was selective to malignant cells and exclusively associated with HDAC activity.

Figure 13:
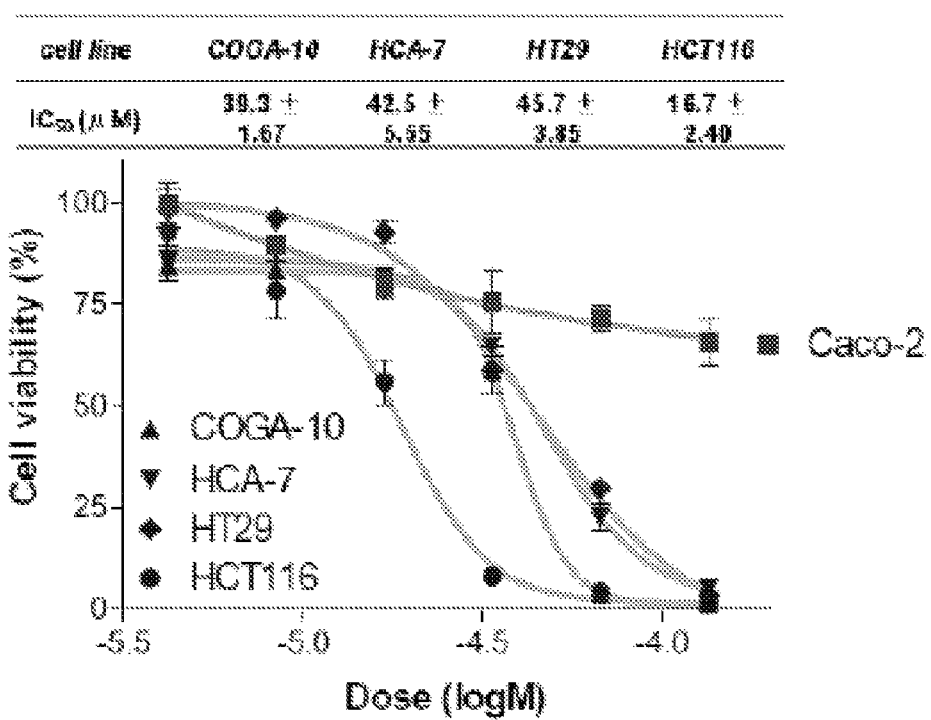
FIG. 13. Inhibition of cell viability by BKAc-Puro is presented in dose-response curve format for the same cell lines as in FIG. 8. The cell lines were treated with DMSO or the indicated doses of agent (4.22, 8.44, 16.9, 33.8, 67.5, or 135 μM) for 5 d followed by MTS assay. Data represent mean values of triplicate mesurements±s.d. (n=3). $IC_{50}$ values were fit by logistic regression.
Figure 14:
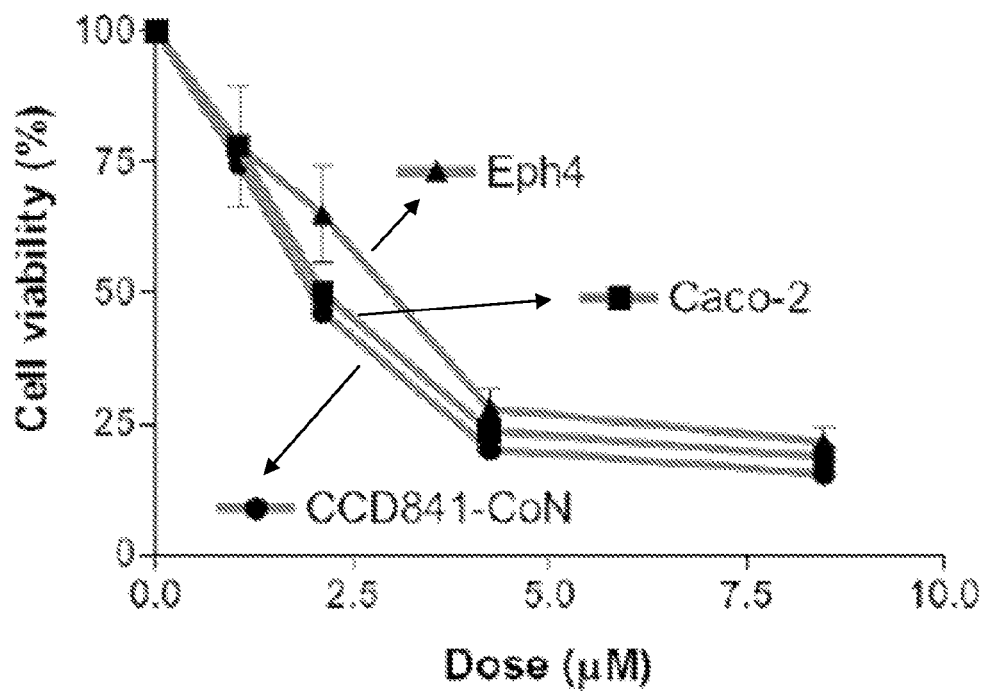
FIG. 14. Inhibition of cell viability by parental Puro. The cell lines were treated with the indicated doses of Puro (0, 1.1, 2.1, 4.2, or 8.4 μM) for 3 d followed by MTS assay. Data represent mean values of triplicate mesurements±s.d.
Figure 15:
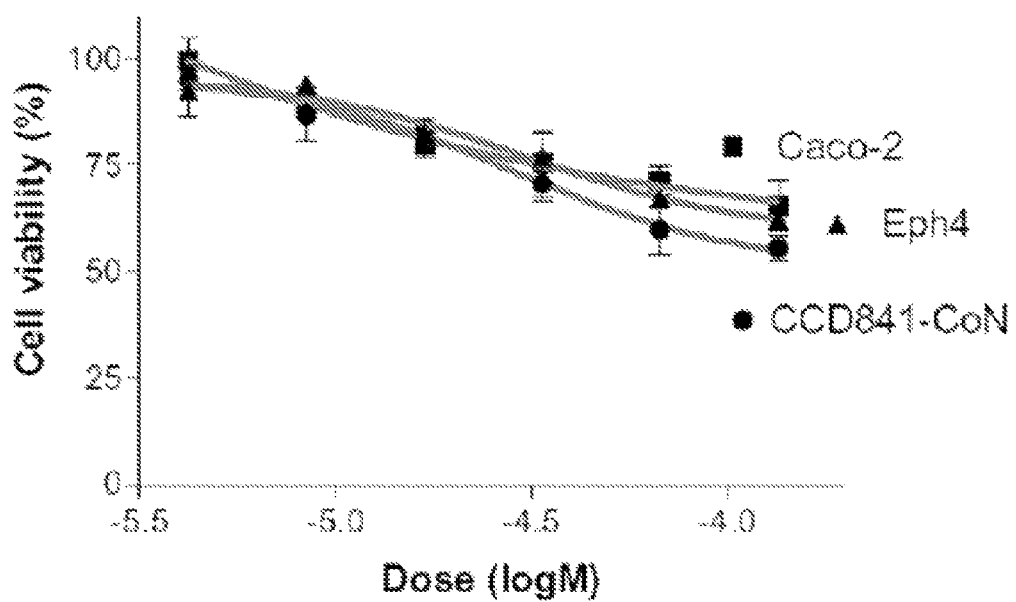
FIG. 15. Inhibition of cell viability by BKAc-Puro. The cell lines were grown and analyzed as in FIG. 12.
Figure 16:
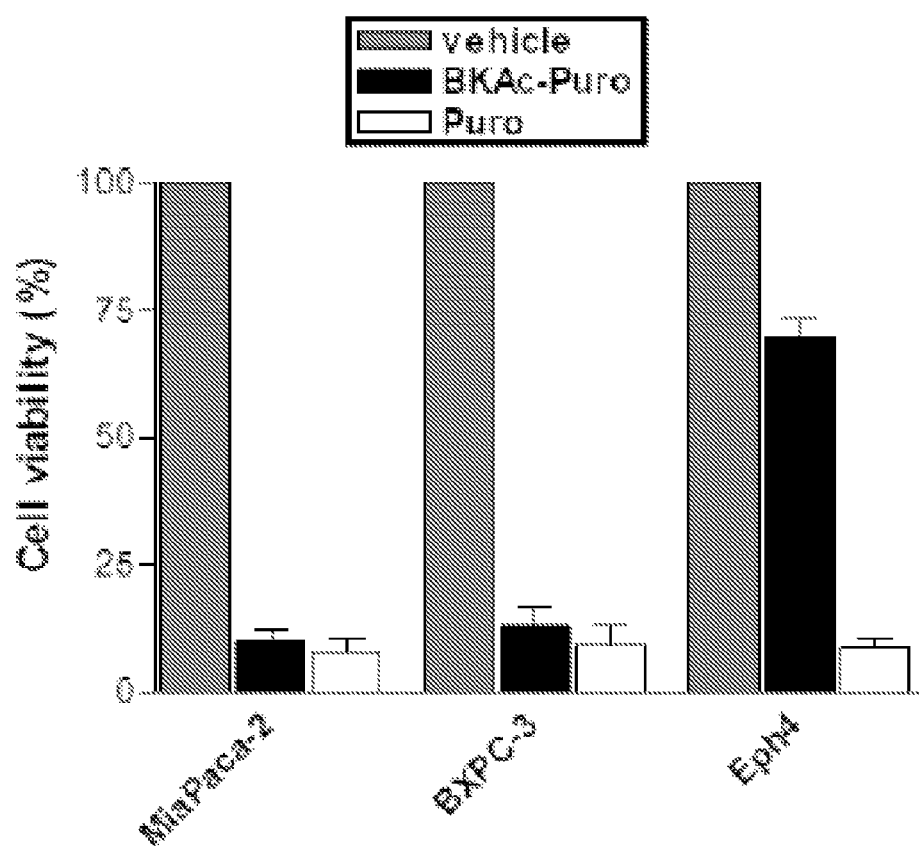
FIG. 16. Anticancer effect of BKAc-Puro on pancreatic cell lines. The cell lines were treated with DMSO (vehicle), BKAc-Puro (54 μM), or Puro (4.2 μM) for 5 d followed by MTS assay. Normal Eph4 (non-pancreatic) cells are shown as control. Data represent mean values of triplicate mesurements±s.d.

To further evaluate the anticancer efficacy of BKAc-Puro, cell viability assays using MTS, 3-(4,5-dimethylthiazol-2-yl)-5-(3-carboxymethoxyphenyl)-2-(4-sulfophenyl)-2H-tetrazolium were performed (FIG. 13). The dose-response curves obtained from the panel of colon cell lines indicate comparable values of $IC_{50}$ ($10^1$ μM range) for the malignant cell lines with high HDAC and CTSL activity. In striking contrast, the $IC_{50}$ values for non-malignant Caco-2 cells were not available, as sufficient inhibition of cell viability was not achieved with doses up to 135 μM, more than 30 times higher dose of parental Puro effective to these cells (FIG. 14). Normal cell lines with low HDAC activity (CCD841-CoN and Eph4) showed similar pattern of dose-response to Caco-2 (FIG. 15), proving that the observed inactivity of the agent is not limited to Caco-2. Furthermore, the BKAc-Puro was also effective to other malignant cell lines including pancreatic cancer (FIG. 16), consistent with their increased HDAC and CTSL activities (FIGS. 1-3), suggesting that the agent could be effective to a broad spectrum of cancers. Taken together, these results demonstrated that the BKAc-Puro exhibits high grade of selectivity toward cells with high HDAC and CTSL activity, which is the characteristic of malignant cancer, while securing tight protection to non-malignant and normal cells with low (basal) HDAC and CTSL activity.

Figure 17:
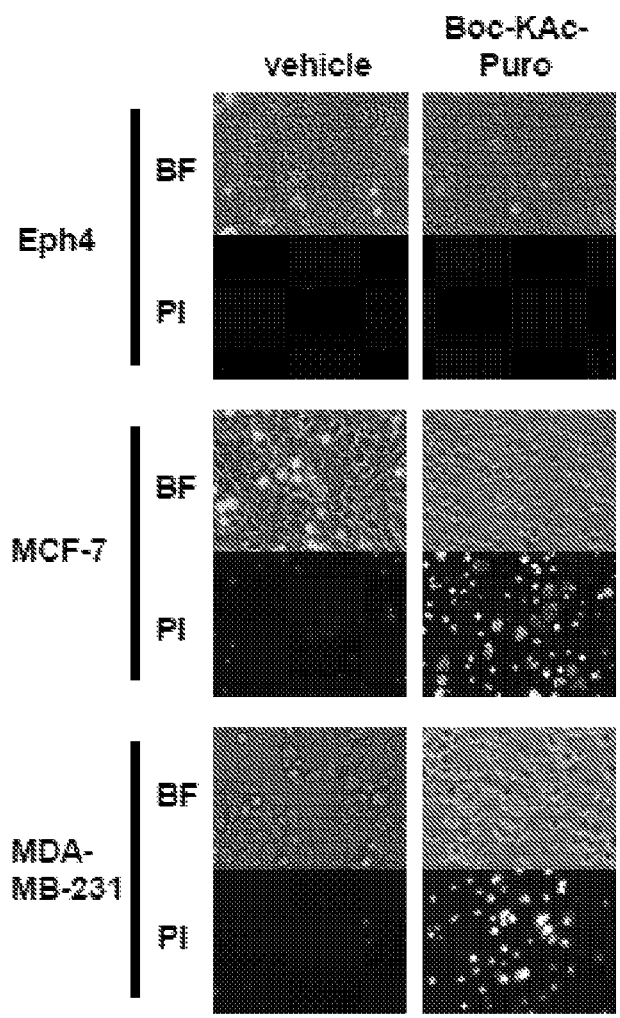
FIG. 17. Selective cytotoxicity by BKAc-Puro on breast cancer cells. Normal mammary gland epithelial cells (Eph4) and breast cancer cells (MCF-7 and MDA-MB-231) were grown and analyzed as in FIG. 10. BF, bright field. PI, fluorescent PI channel. BKAc-Puro can selectively cause cell death in breast cancer cells (MCF-7 and MDA-MB-231) while leaving normal Eph4 cells unharmed.
Figure 18:
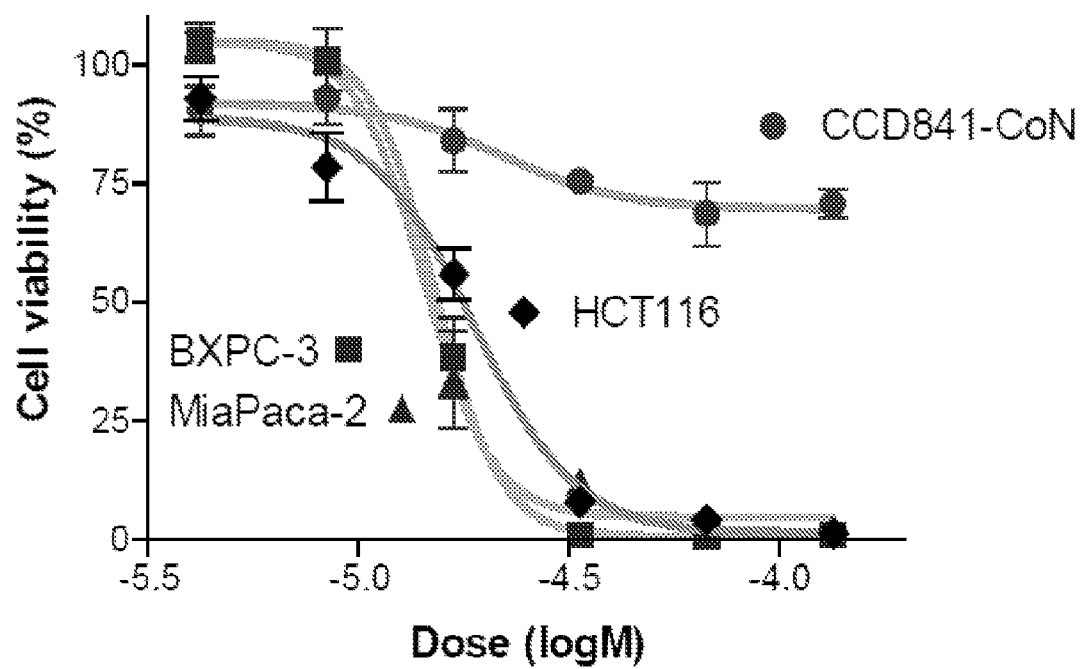
FIG. 18. Selective cytotoxicity by BKAc-Puro on pancreatic cancer cells. Pancreatic cancer (BXPC-3 and Miapaca-2), colon cancer (HCT116 as a positive control sensitive to the drug), and normal colon (CCD841-CoN as a negative control) cells were grown and analyzed as in FIG. 13. BKAc-Puro can effectively cause cell death on pancreatic cancer cells (BXPC-3 and MiaPaca-2) that are known to resistant to conventional chemotherapeutic drugs including 5-FU and Gemicitabine.
Figure 19:
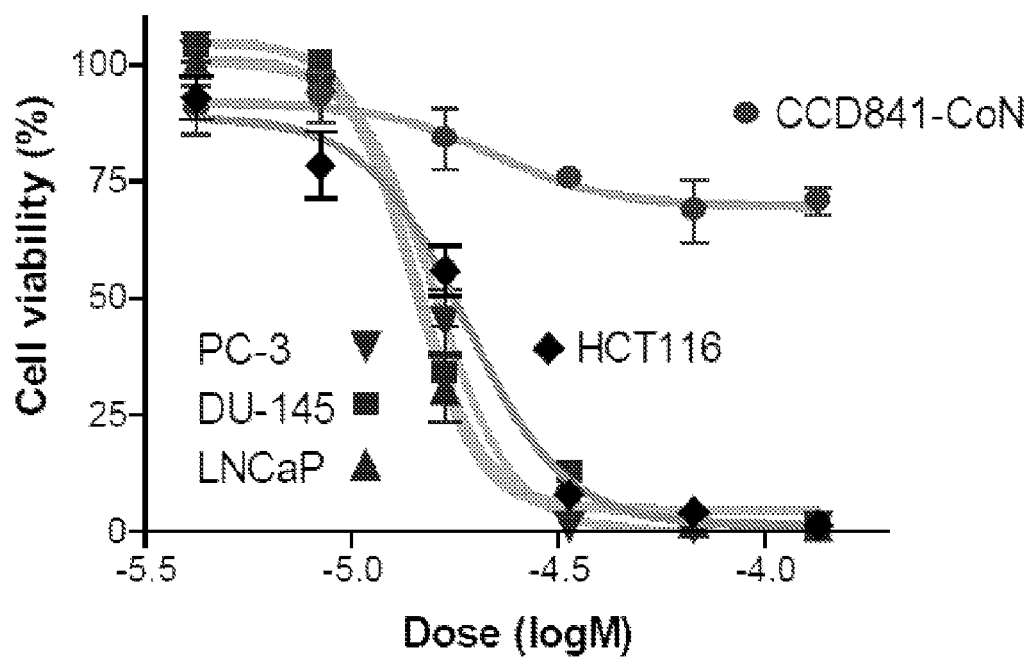
FIG. 19. Selective cytotoxicity by BKAc-Puro on prostate cancer cells. Prostate cancer (PC-3, DU-145, and LNCaP), colon cancer (HCT116 as a positive control sensitive to the drug), and normal colon (CCD841-CoN as a negative control) cells were grown and analyzed as in FIG. 13. BKAc-Puro can effectively cause cell death on prostate cancer cells.

BKAc-Puro selectively caused cell death in breast cancer cells (MCF-7 and MDA-MB-231) while leaving normal mammary gland epithelial cells (Eph4) unharmed (FIG. 17). BKAc-Puro effectively caused cell death in pancreatic cancer cells (BXPC-3 and MiaPaca-2) that are known to resistant to conventional chemotherapeutic drugs including 5-FU and Gemicitabine while having relatively little effect on normal colon cells unharmed (FIG. 18). BKAc-Puro effectively caused cell death in prostate cancer cells (PC-3, DU-145 and LNCaP) while having relatively little effect on normal colon cells unharmed (FIG. 19).

Figure 20:
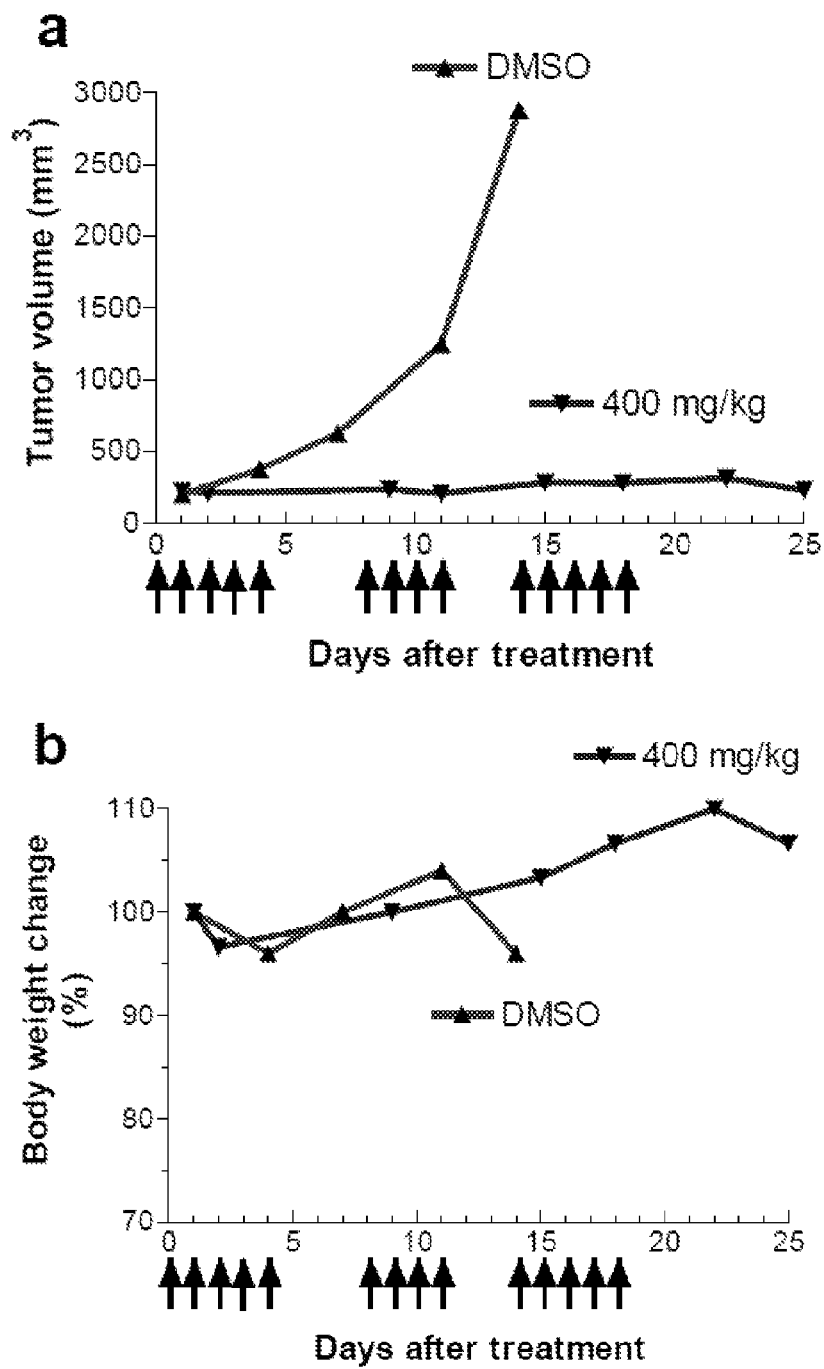
FIG. 20. In vivo anticancer efficacy of BKAc-Puro. (a) Inhibition of tumor growth in mouse xenograft model. HCT116 cells were implanted subcutaneously into female nude mice. When the developed tumors reached 200 mm$^3$, animals were intraperitoneally injected by the indicated dose of the compound or vehicle control (DMSO). Tumor volume was estimated by the equation vol=(a×b$^2$)/2, where vol, a, and b represent volume, the length of the major axis, and the length of the minor axis, respectively. Arrows indicate the time points of treatment. (b) Body weight change during the treatment in a. Value is expressed in percent change compared to the day of the first treatment. In vivo anticancer efficacy of BKAc-Puro was demonstrated by the inhibition of tumor growth in mouse xenograft model. No toxicity was observed in the group treated with 400 mg/kg of the drug during and after 14 times injections.

In vivo anticancer efficacy of BKAc-Puro was demonstrated by the inhibition of tumor growth in a mouse xenograft model. No toxicity was observed in the group treated with 400 mg/kg of the drug during and after 14 injections (FIG. 20A-B). Further, in vivo anticancer efficacy of BKAc-Puro was demonstrated by the inhibition of tumor incidence in mouse xenograft model (FIG. 21). When treated with 200 mg/kg, no tumors greater than 300 mm$^2$ were observed. Consistent with the data presented above, no toxicity was observed in the groups treated with the drug.

Figure 22:
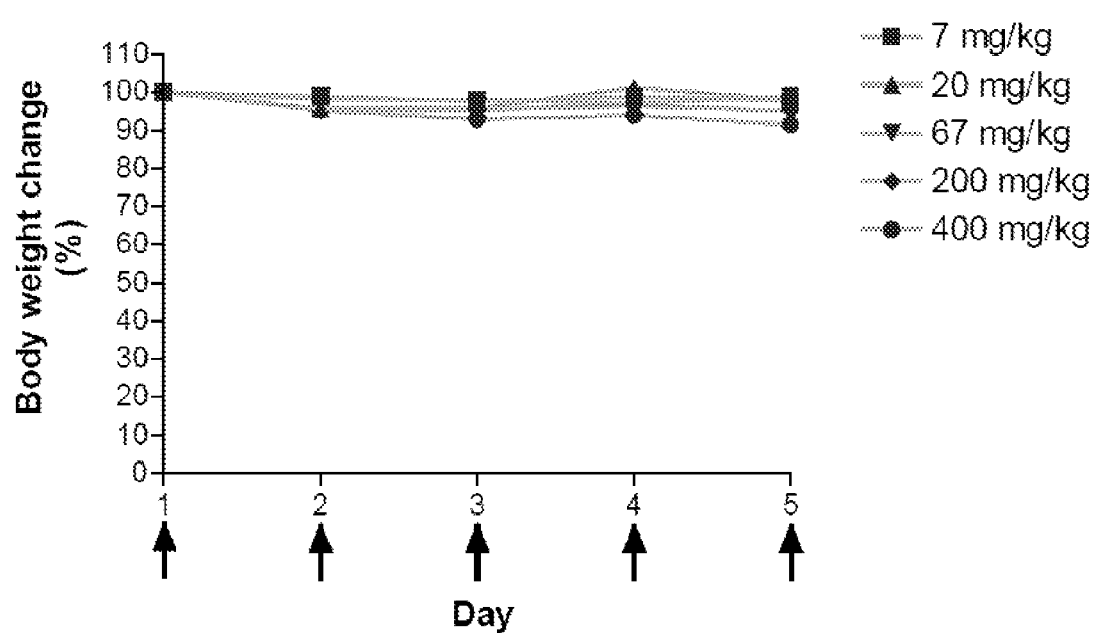
FIG. 22. Dose escalation toxicity study. Female nude mice (8-10 weeks old) were treated with the indicated dose of BKAc-Puro (7, 20, 67, 200, and 400 mg/kg; n=3 in each treatment group). Body weight change during the treatment is expressed in percent change compared to the day of the first treatment. Arrows indicate the time points of treatment. Data represent mean values±s.d. (n=3). No severe systemic toxicity was observed up to 400 mg/kg from 5 consecutive daily injections. Considering that the LD50 values for single administration of unmasked puromycin are 335 mg/kg (intravenously), 580 mg/kg (intraperitoneally), and 720 mg/kg (orally) [ABANAE Antibiotics Annual, 1954/1955], BKAc-Puro appears to be well-protected and well-tolerated in animals.

No severe systemic toxicity was observed up to 400 mg/kg from 5 consecutive daily injections (FIG. 22). Considering that the LD50 values for single administration of unmasked puromycin are 335 mg/kg (intravenously), 580 mg/kg (intraperitoneally), and 720 mg/kg (orally) [ABANAE Antibiotics Annual, 1954/1955], BKAc-Puro appears to be well-protected and well-tolerated in animals.

Example 5. Boc-Lys(Ac)-5-Fluorocytidine

Synthesis of Boc-Lys(Ac)-5-fluorocytidine

Boc-Lys(Ac)-5-fluorocytidine (BKAc-5FCR) was synthesized by conjugating Boc-Lys(Ac)-OH with the amino group of 5-fluorocytidine (5FCR) (FIG. 23A).

t-butyl (6-acetamido-1-((1-((2R,3R,4S,5R)-3,4-dihydroxy-5-(hydroxymethyl)tetrahydrofuran-2-yl)-5-fluoro-2-oxo-1,2-dihydropyrimidin-4-yl)amino)-1-oxohexan-2-yl) carbamate (Boc-Lys(Ac)-5-fluorocytidine): A mixture of 5-fluorocytidine, N-α-(t-butoxycarbonyl)-N-ε-acetyl-L-lysine (Boc-Lys(Ac)-OH), 1-ethyl-3-(3-dimethylaminopropyl)carbodiimide hydrochloride (EDC.HCl), 1-hydroxybenzotriazole (HOBt), and N,N-diisopropylethylamine were stirred in DMF (dimethylformamide) for 18 h. Water was then added and the organic soluble part was extracted with methylene chloride. Then the compound was purified by silica gel column chromatography using 5-10% MeOH in methylene chloride and dried to give Boc-Lys(Ac)-5-fluorocytidine.

Biological Data

The in vitro efficacy of the compounds in a series of BxPC3 and CFPac-1 derivatives with reduced Class I HDAC activity following Ski knockdown (shSki), HDAC3 knockdown and control (shGFP) was assessed. The growth inhibitory/viability effects of the compounds ($IC_{50}$ value, the concentration resulting in 50% growth inhibition) on the various cell lines were determined by dose response curve analysis (GraphPad Prism software) of MTT [3-(4,5dimethylthiazol-2-yl)-2,5-diphenyl-tetrazolium bromide] cell viability assay. If the prodrugs are activated in an HDAC-dependent manner, the cells with reduced HDAC activity would be predicted to be more resistant to the prodrug treatment than control cells, while the effect of free parental drugs on both cells would be expected to be similar.

Figure 24:
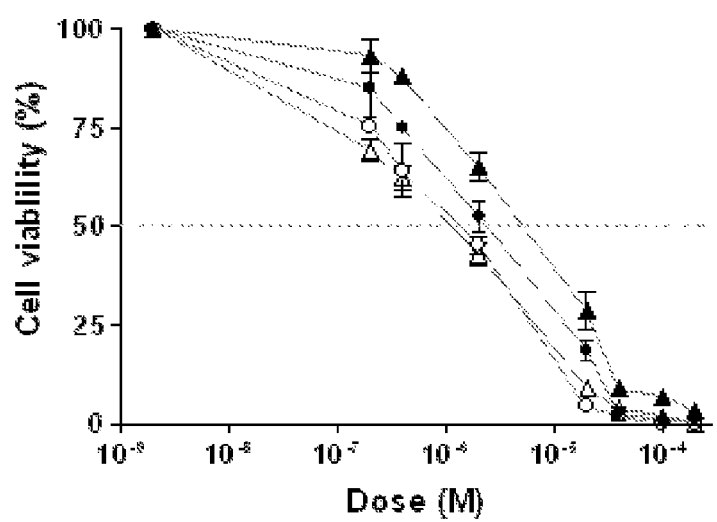
FIG. 24. Effect of the prodrug on cell viability of BxPC3 cells (shGFP and shSki). Cells were treated with the indicated dose of drugs (BKAc-5FCR or 5FCR) for 72 hr followed by MTT assay. Data represent mean values of triplicate measurements±standard deviation. IC$_{50}$ values were derived from nonlinear curve fit of the dose response data using an outlier's exclusion, variable slope model (GraphPad Prism software). All values are means of at least two independent experiments.

$IC_{50}$ values were determined for compound Boc-Lys(Ac)-5-fluorocytidine (BKAc-5FCR) and it's parental drug 5FCR in BxPC3 cells stably expressing shRNas against either GFP or Ski (shGFP and shSki). Consistent with the 50-60% difference in HDAC activity in these cells (FIGS. 4-5), a moderate but significant reduction in drug response was seen in BxPC3 shSki cells treated with BKAc-5FCR over shGFP control cells, (FIG. 24), which showed a two-fold difference in $IC_{50}$ values, shSki: 5.2 versus shGFP: 2.6. In contrast, no significant changes in IC$_{50}$ values were observed in the same cells treated with 5FCR (shSki: 1.2 versus shGFP: 1.3).

Figure 25:
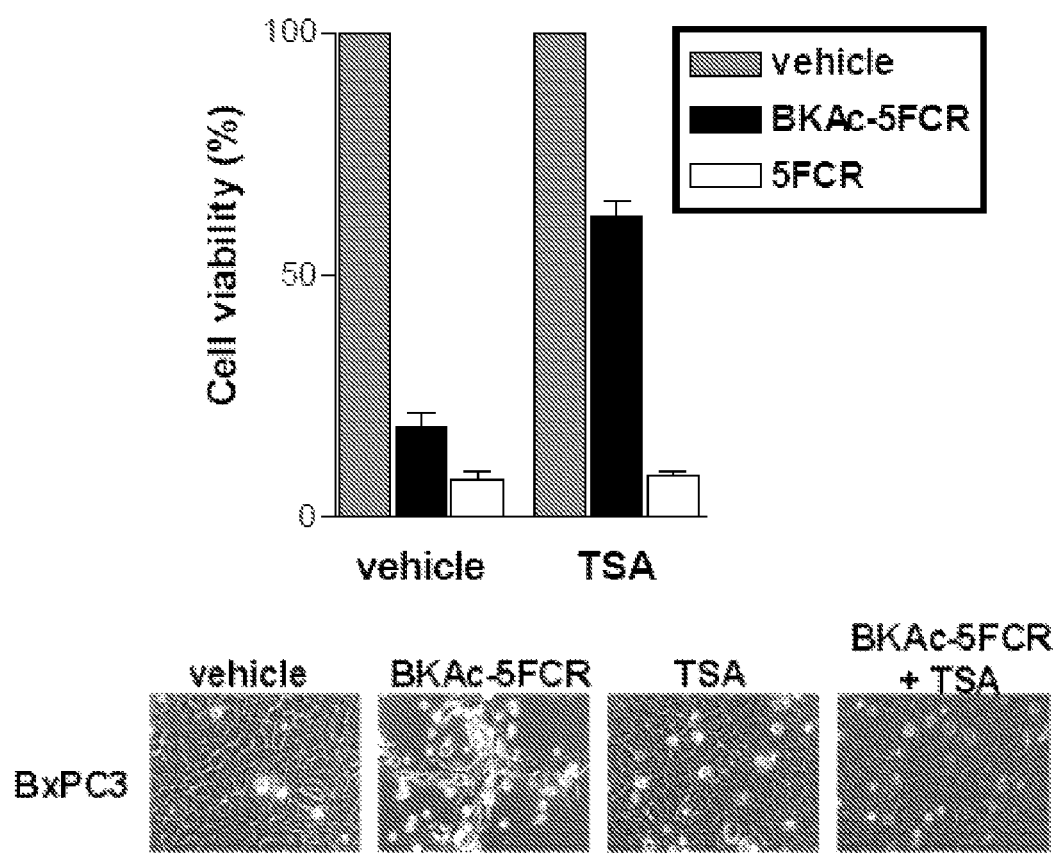
FIG. 25. Selective cytotoxicity by BKAc-5FCR. Human pancreatic BXPC3 cells were treated with DMSO (vehicle), BKAc-5FCR (20 μM), or 5FCR (20 μM) for 72 hr with or without TSA (50 μM) followed by MTS cell viability assay. Representative phase contrast images of cells treated with DMSO (vehicle) or BKAc-5FCR (20 μM) for 72 hr with or without TSA (50 μM) are shown. The HDAC-dependent activation of BKAc-5FCR in BXPC-3 cells was further demonstrated in the presence of HDAC inhibitor TSA where the cytotoxic effect of BKAc-5FCR was substantially compromised.

The HDAC-dependent activation of BKAc-5FCR in BXPC-3 cells was further demonstrated in the presence of HDAC inhibitor TSA where the cytotoxic effect of BKAc-5FCR was substantially compromised (FIG. 25).

Example 6. Additional Prodrugs

Figure 6:
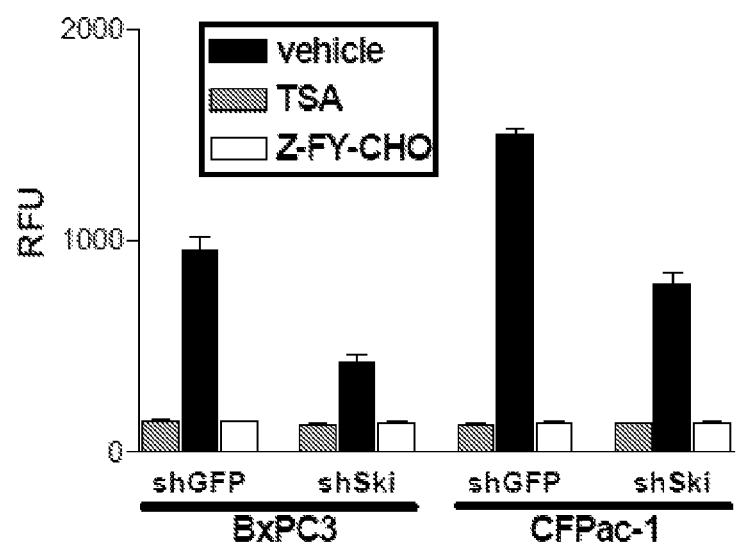
FIG. 6. A. Release of AMC by combined HDAC and endogenous protease-dependent enzymatic reaction in BxPC3 and CFPac-1 cells (shGFP and shSki). Cells were incubated with substrate Boc-Lys(Ac)-AMC (25 μM) for 6 hr with DMSO (vehicle), TSA (1 μM), or Z-FY-CHO (10 μM) as indicated, followed by fluorescence measurements. Data represent mean values of triplicate measurements±standard deviation. RFU, relative fluorescent units. B. Time course of AMC release in BxPC3 cells (shGFP and shSki). Each cells were incubated with Boc-Lys(Ac)-AMC (25 μM) for 2.5, 6.0, and 23 hr with DMSO (vehicle) or TSA (1 μM) as indicated.
Figure 6:
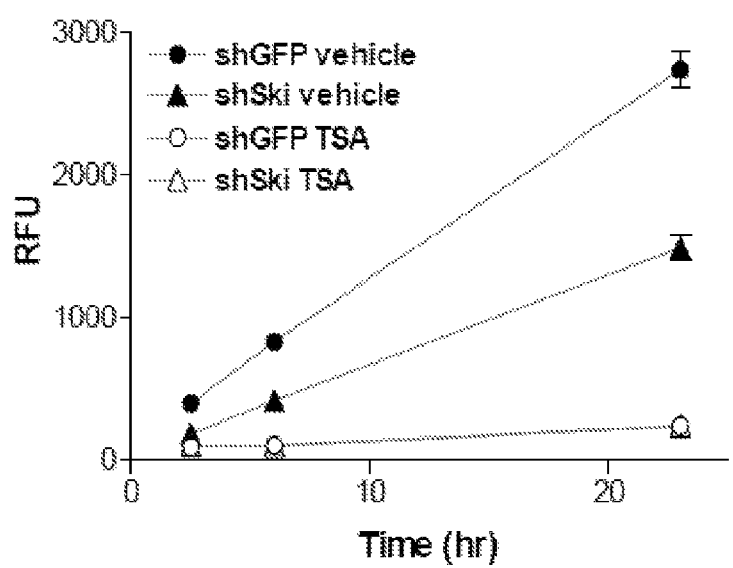

The recognition of ε-acetylated lysine residue by class I HDACs is rather insensitive to changes in sequence context. As a result, it is possible to design peptide substrates optimized with respect to the second step in the reaction, namely proteolysis. During the course of our study on characterizing HDAC activity in pancreatic cancer cell lines, we noticed that the Lys-AMC amide bond can be cleaved by endogenous proteases without adding trypsin (FIGS. 5B and 6). However this cleavage is completely inhibited by TSA treatment, indicating that TSA sensitive HDAC activity is a prerequisite.

By using pancreatic cancer cell lines such as BxPC3 and CFPac-1 cells, kinetic parameters of cleavage of the following available substrates are analyzed for cathepsin L conjugated to AMC: Z-Phe-Lys-, Boc-Phe-Lys-, Ac-Phe-Lys-, HCO-Phe-Lys-, Z-Lys-, Boc-Lys-, Ac-Lys-, HCO-Lys-, where Z (benzyloxy-carbonyl), Boc (tert-butoxycarbonyl), Ac (acetyl), and HCO (formyl) represent α-amino protecting groups.

Most of these substrates are also recognized by another lysosomal cystein protease cathepsin B, and both amino acid sequence and α-amino protecting group were reported to affect kinetic parameters of clevage, yielding substrates that represent fast ($t_{1/2}$=~10 min), medium ($t_{1/2}$=1-3 hr), and slow ($t_{1/2}$=8-10 hr) cleavage reaction (Dubowchik, G. M. & Firestone, R. A. 1998). Based on the similarity in substrate recognition by cathepsin B and L, we the speed of drug activation is controlled by selecting some of the above substrates to optimize overall efficacy of the drugs. Having identified a peptide sequence, additional prodrugs are synthesized as described previously. The procedure is simple and straightforward and does not require special concerns. In fact, similar amide coupling reactions have been reported (Manfredini, S. et al. 2000; Balajthy, Z. et al. 1992).

Figure 26:
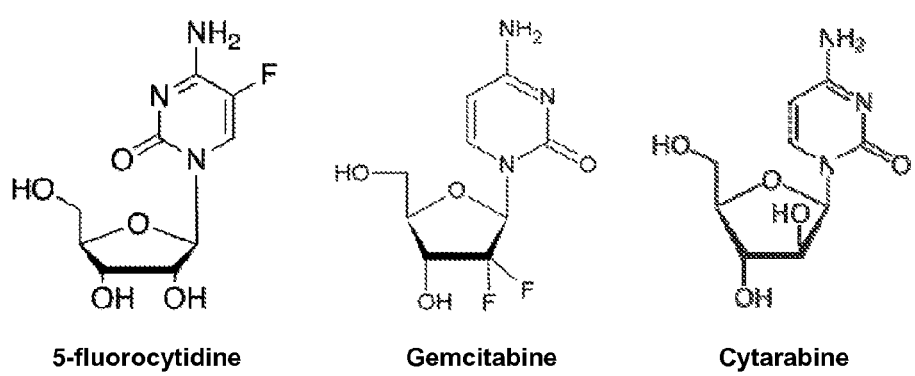
FIG. 26. Nucleoside antimetabolite analogs.

An additional aspect of the invention provides compounds with variable peptide substrates and variable parental amine-containing and non-amine containing nucleosides and deoxynucleosides including 2'-deoxy-5-fluorocytidine, 5'-deoxy-5-fluorocytidine (precursors of 5-FU), Gemicitabine, and Cytarabine (FIG. 26). Such compounds are synthesized by a similar amide coupling and are expected to function analogously to compound BKAc-5FCR and BKAc-Puro.

An additional aspect of the invention provides compounds with variable peptide substrates and variable parental amine-containing containing chemotherapeutic agents and are synthesized by a similar amide coupling. Such compounds are expected to function analogously to compound BKAc-5FCR and BKAc-Puro.

An additional aspect of the invention provides compounds with variable peptide substrates and variable non-amine containing chemotherapeutic agents and are synthesized by an amide coupling of the peptide substrate to a "Y" linker which is attached to the chemotherapeutic agent. Compounds with a variety of "Y" linkers are expected to function analogously to compound BKAc-5FCR and BKAc-Puro. The linker "Y" may be a "self-immolative" linker, which cleaves spontaneously after the carrier-linker bond, i.e. the amide bond, is broken. Example of such a "self-immolative" linker includes, nut is not limited to, a para-aminobenzyl alcohol linker (Richard, J. et al. 2008).

An additional aspect of the invention provides compounds with variable peptide substrates and variable chemotherapeutic agents that are customized to act as selective substrates for any of the specific HDACi, e.g., HDAC3.

An additional aspect of the invention provides compounds with variable peptide substrates and variable therapeutic agents that are customized to act as therapeutics for any disease that is associated with elevated levels of HDACs, proteases or both, Such diseases include, but are not limited to, neurodegenerative diseases (Chuang, D. et al. 2009), Alzheimers disease, Parkinson's disease, neuropsychiatric diseases (Fischer, A. et al. 2010), infectious disease such as HIV/AIDS (Andrew, K. T. et al. 2012), parasitic diseases (Andrew, K. T. et al. 2012) or inflammatory diseases (Halili, M. A. et al. 2009).

Example 7. Additional Biological Studies

Other Cell Lines

The prodrugs are evaluated by determining IC$_{50}$ values in other cancer cell lines. It is expected that cells which have the lowest HDAC levels, either due to improved knockdown of Ski levels or as a direct result of shRNA directed against HDAC3 (and potentially other HDACs) would be more resistant to the prodrugs. Conversely, it is expected that cells which have the highest HDAC levels would be less resistant to the prodrugs.

Monitoring of Prodrugs by HPLC

To confirm that the prodrugs are processed by HDACs and cathepsin L, commercially available purified enzymes (class I HDACs and cathepsin L are available from TEBU-BIO) are used either alone or in combination with each other, as well as assaying directly cell extracts after drug treatment. The processing of the prodrugs is monitored by HPLC (C-18 column) or TLC. In addition, hydrolysis studies are performed by measuring enzymatic and non-enzymatic stability of the prodrugs in human plasma, tissue culture medium containing 20% fetal calf serum, and defined buffer solutions with variable pH.

Example 8. Cell Death Induced by Boc-Lys(Ac)-Puromycin

Figure 27:
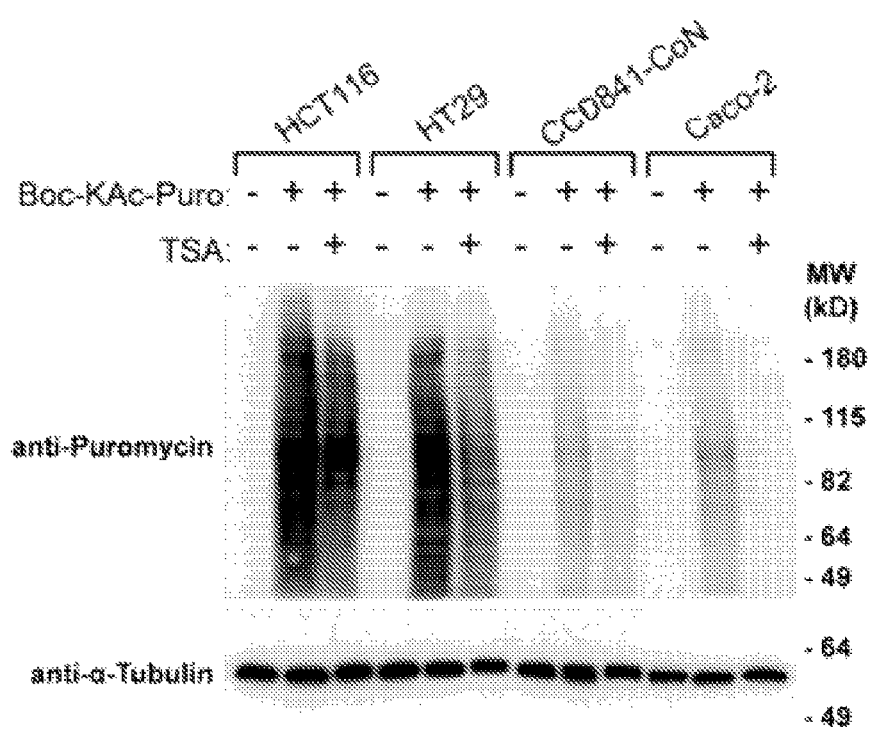
FIG. 27. Levels of Puro-incorporated proteins in the cells were monitored by immunoblotting. Indicated cell lines were treated either with vehicle control DMSO or Boc-KAc-Puro (16.9 μM) in the presence or absence of TSA (0.5 μM) for 20 h, followed by preparation of cell lysates. The lower panel (anti-α-Tubulin) serves as a loading control.
Figure 28:
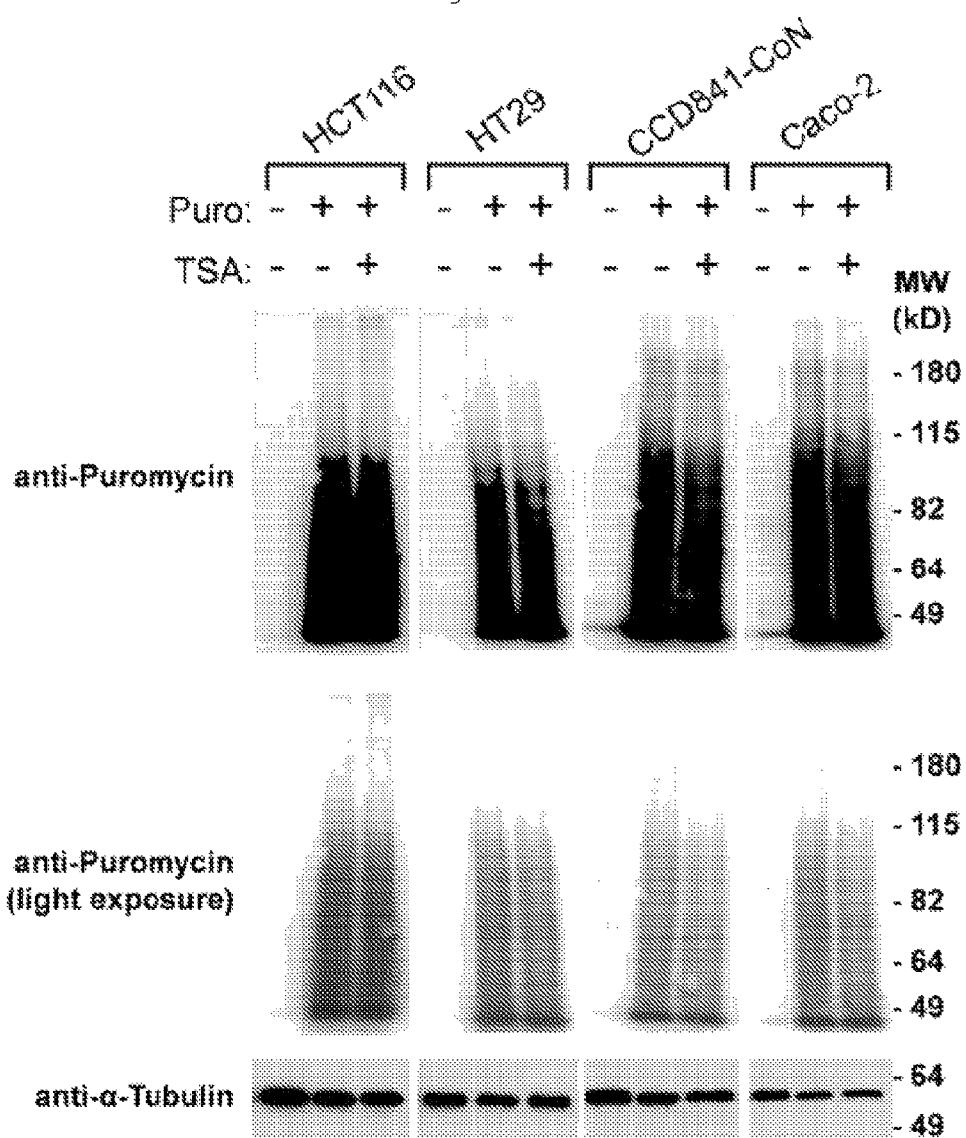
FIG. 28. Levels of Puro-incorporated proteins in the cells were monitored by immunoblotting. Indicated cell lines were treated either with vehicle control DMSO or Puro (2.1 μM) in the presence or absence of TSA (0.5 μM) for 16 h, followed by preparation of cell lysates. The middle panel shows lighter exposure of the same blot in the top panel. The lower panel (anti-α-Tubulin) serves as a loading control.

The mechanism of cell death induced by Boc-KAc-Puro was examined. As a Tyr-tRNA mimetic, Puro enters the ribosome A site and blocks peptide chain elongation by covalent incorporation into the C terminus of nascent polypeptide chains (Pestka, S. et al. 1972). In contrast, the prodrug is unable to do so since its active center amino group is masked. This allows for the monitoring of active Puro conversion in cells by immunological detection of Puro-labeled proteins using anti-Puro antibody (Schmidt, E. K. et al. 2009). To confirm that Boc-KAc-Puro is selectively converted into Puro in malignant cancer cells resulting in their death, the level of Puro incorporation was assessed by immunoblotting using cell lysates from cells treated with the agent. The intensity of Puro incorporation was substantially greater in malignant cancer cells (HCT116 and HT29) compared with normal and non-malignant cells (CCD841-CoN and Caco-2) (FIG. 27) in accordance with their sensitivity to the agent. The compromised intensity in the presence of TSA was at least partially attributable to the specific requirement of HDAC activity for the prodrug activation. When these cells were treated with parental Puro, there was no difference in terms of Puro incorporation regardless of TSA treatment (FIG. 28). This is consistent with the ability of parental Puro to kill all of these cells examined. The results indicated that the agent can be selectively converted into Puro in malignant cancer cells leading to their death by a Puro-dependent mode of action.

Example 9. Tumor Growth Inhibition by Boc-Lys(Ac)-Puromycin

Figure 29E:
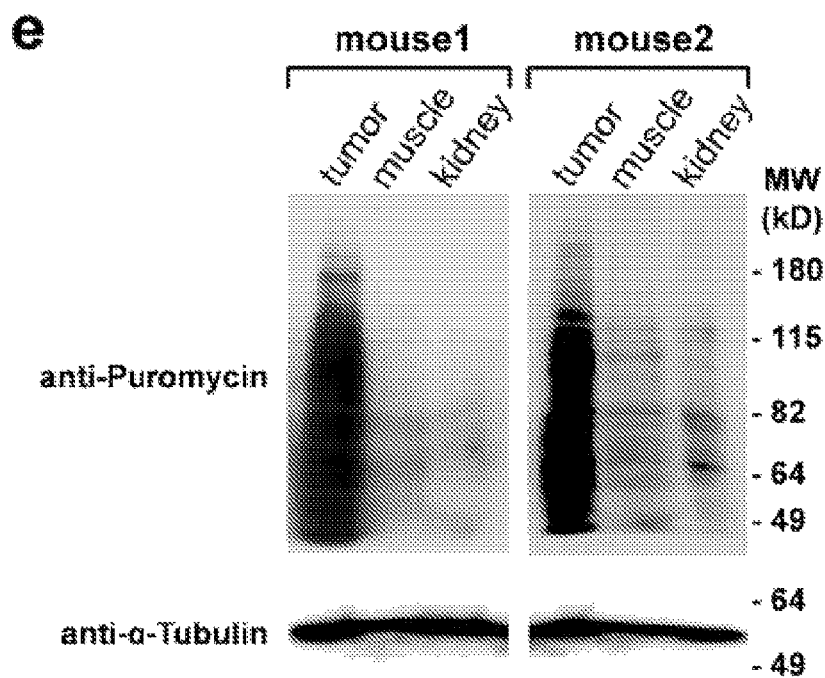
FIG. 29. In vivo anticancer efficacy of Boc-KAc-Puro. (a) Tumor growth in HCT116 xenograft model. Animals were treated with acidified saline control or Boc-KAc-Puro (50 or 150 mg/kg). Values are mean±s.d. (n=5 mice per group). *P<0.001 compared to the control group. P=0.000716 (50 mg/kg), P=0.000349 (150 mg/kg) at 10 d. (b) Body weight change during the treatment in a was monitored as a sign of general animal health. Values are mean±s.d. (c) Tumor growth in HT29 xenograft model. Animals were treated with acidified saline control or Boc-KAc-Puro (150 mg/kg). Values are mean±s.d. (n=5 mice per group). *P<0.001 compared to the control group. P=0.000514 (150 mg/kg) at 10 d. (d) Body weight change during the treatment in c was monitored as a sign of general animal health. Values are mean±s.d. (e) Levels of Puro-incorporated proteins were monitored by immunoblotting. Animals bearing HT29 xenograft tumor were given daily intraperitoneal administration of the prodrug at 150 mg/kg/dose for 3 d, followed by preparation of tissue lysates. The lower panel (anti-α-Tubulin) served as a loading control.

To assess in vivo anticancer efficacy of the agent, mouse xenograft models bearing human colon cancer cell lines were used (HCT116 and HT29). First, HCT116 cells were subcutaneously injected into the lower flank of mice, then dosing was initiated when small palpable tumors had developed (>3 mm in diameter). Boc-KAc-Puro was daily administered intraperitoneally at 50 and 150 mg/kg/dose for 10 d. The agent caused a dose-dependent inhibition of tumor growth (FIG. 29A). In this model, animals treated with the prodrug developed significantly smaller tumor mass in comparison to the animals treated with acidified saline control (P<0.001). Furthermore, daily intraperitoneal administration of the prodrug as high as 150 mg/kg/dose for 10 d appeared well-tolerated as judged by weight loss determination (FIG. 29B). Similar results were obtained using HT29 cells at 150 mg/kg/dose (FIG. 29C-D). These results clearly demonstrated in vivo anticancer efficacy of the prodrug Boc-KAc-Puro without severe off-target systemic toxicity.

To assess if the prodrug is selectively activated at tumor sites in vivo, levels of Puro incorporation into polypeptides in tumors and normal tissues were monitored, including muscle underneath the tumors and kidney, one of the major excretion sites for drug metabolites. Animals bearing HT29 xenograft tumor were given daily intraperitoneal administration of the prodrug at 150 mg/kg/dose for 3 d followed by preparation of tissue lysates for immunological detection of Puro-labeled proteins. The intensity of Puro incorporation was substantially greater in tumors compared with normal muscle and kidney (FIG. 29E), further supporting tumor specific activation of the agent in vivo. The results indicated that the agent can be selectively converted into Puro in tumor tissues leading to their growth inhibition by Puro-dependent mode of action.

Discussion

Histone deacetylases (HDACs) are the key enzymes involved in the epigenetic regulation of histone and non-histone proteins by modulating protein structure and function through deacetylation of lysine residues (Witt, O. et al. 2009). Protein lysine acetylation is tightly regulated by HDACs and histone acetyltransferases (HATs), which influence chromatin dynamics, protein turnover and DNA damage response (Witt, O. et al. 2009; Lee, K. K. & Workman, J. L. 2007; Choudary, C. et al. 2009). Thus disregulation of these enzymes could lead to a broad spectrum of human diseases including cancer. Accumulating evidence indicate pro-proliferative and pro-survival roles of HDACs to support tumor initiation, progression and metastasis (Haberland, et al. 2009; Mariadason, J. M. 2008; Wu, M. Z. et al. 2011).

In order to develop better therapeutics to take advantage of HDACs, a new approach is needed. Instead of using HDAC inhibitors (Minucci, S. et al. 2006), intrinsically elevated HDAC activity can be taken advantage of in order to selectively deliver cytotoxicity to the tumor cells. Since certain tumor cells are reliant on their elevated levels of HDACs to survive and proliferate under stressful conditions, a chemical HDAC substrate coupled to a therapeutic agent can preferentially cause lethality in cells with high, but not low, HDAC activity. Upon deacetylation by HDAC, the HDAC substrate is, in turn, recognized as a substrate by specific intracellular proteases that cleave amide bonds, which ultimately results in release of the therapeutic agent. Although many peptide-based prodrugs activated by tumor-associated proteases have been developed (Choi, K. Y. et al. 2012), stability and nonspecific activation of parental drugs due to ubiquitous proteases are key factors limiting their clinical efficacy. By introducing an s-acetylated lysine as the first requirement, the results disclosed herein show that the resulting prodrug can be well-protected from proteolytic cleavage until it is deacetylated by the intracellular HDAC, and thus enable highly selective drug activation in tumor tissues.

This approach allows for the targeting of two independent enzymes aberrantly activated in tumor cells, providing better selectivity. In addition, because HDAC activity is undetectable in plasma, and the amide bond between HDAC substrate and therapeutic agent is hardly cleaved by ubiquitous proteases in cytoplasm or plasma, this approach also minimizes the known drawbacks of peptide-based prodrugs.

Described herein is a new approach for selective cancer therapy by targeting increased histone deacetylase (HDAC) and increased protease activity in certain cells. Therefore, the prodrug itself or the therapeutic agent X should not be an HDACi or protease inhibitor. This approach is promising strategy for the next generation of selective anticancer drugs.

In order to develop better and more selective therapeutic approaches targeting HDACs, we took advantage of certain tumor cells that are more reliant on their elevated level of HDAC and CTSL to survive and proliferate under stressful conditions. The elevated level of HDACs in tumor cells result in cells that are highly sensitive to HDACi. Thus, instead of inhibiting HDACs, novel activity based agents wer designed that selectively eliminate cancer cells by taking advantage of their elevated HDAC activity.

Although nucleosides such as gemicitabine (Heunemann, V. et al. 2011) and 5-FU (5-fluorouracil) (Lamont, E. B. et al. 1999) are current standard therapeutic regimens for pancreatic tumors, their efficacy is far from an ideal treatment for this devastating disease. Thus, there is an urgent need to develop drugs that are more effective than these conventional drugs. As explained herein, elevated HDAC activity, which is mediated by Ski oncoprotein in pancreatic ductal adenocarcinoma (PDA) can provide a therapeutic target.

Selective prodrugs incorporating nucleoside parent agents were designed and synthesized. These prodrugs were synthesizied by coupling "nonselective" nucleoside antimetabolite analogs such as 5-fluorocytidine and puromycin to HDAC substrates to produce prodrugs BKAc-5FCR and BKAc-puro, respectively. The prodrugs were activated by HDACs and proteases, which resulted in selective delivery of the parent drug to the cancer cells.

Since a free N4-amino group of the parental drug of BKAc-5FCR is required for cytotoxicity, this group was protected by conjugating a peptide HDAC substrate containing ε-acetylated lysine residue through amide coupling. In this way, the activation of prodrugs was executed by a HDAC-dependent two-step enzymatic reaction. In the first step catalyzed by HDACs, acetate is released from ε-acetylated lysine. In the next step, the deacetylated lysine is recognized as substrate by specific intracellular proteases that cleave carboxyl terminal lysil amide bonds, releasing active drugs with the free N4-amino group. This approach targeted two independent key enzymes aberrantly activated in tumor cells, providing better selectivity. In addition, because HDAC activity is undetectable in plasma, and the amide bond between ε-acetylated lysine and parental drugs is hardly cleaved by proteases, our approach minimizes the known drawbacks of peptide-based prodrugs such as non-specific activation by ubiquitous proteases in cytoplasm or plasma.

Although peptide-based nucleoside analogs activated by tumor associated proteases were developed previously (Carl, P. L. et al. 1980; Dubowchik, G. M. et al. 1998; Dubowchik, G. M. & Firestone, R. A. 1998; Balajthy, K. et al. 1992), we identified that nonspecific release of parental drugs by ubiquitous proteases in cell cytoplasm or plasma was a major drawback. To address such drawbacks and further improve selectivity in tumor cells, we designed prodrugs that were activated by two independent enzymatic reactions: HDACs and tumor associated proteases. By targeting these key enzymes that act in epigenetic and proteolytic pathways in tumors, we have developed prodrugs for selective cancer chemotherapy.

The prodrugs that are synthesized may have some basal level of cytotoxicity before they are activated by HDAC3. One way to determine the $IC_{50}$ values of the uncleaved forms of the prodrugs would be to use HDAC inhibitors both in vitro and in vivo. In preliminary in vitro experiments, TSA was used to inhibit HDACs in the cells, unfortunately due to the cytotoxic effect of TSA at 1 μM over the 72 hr time period, $IC_{50}$ values were not obtained. To overcome this difficulty, TSA concentration is reduced by titrating to levels (10-50 nM) that should maintain maximal HDAC inhibition and minimal cytotoxicity. HDAC1, 2, 3, and 6, among others, are potential candidate enzymes capable of prodrug activation and they are all known to be TSA sensitive (Bradner, J. E. et al. 2010), hence this range of TSA concentration should sufficiently inhibit all of these enzymes. Should it prove impossible to find a range of TSA that allows 72 hr cell toxicity assays, the use of other HDAC inhibitors is explored by routine experimentation. For example, among available HDAC inhibitors, SAHA (Vorinostat), a FDA approved pharmaceutical HDAC inhibitor (Bradner, J. E. et al. 2010), is known to inhibit all of these HDACs with much lower cytotoxicity than TSA. Thus, SAHA is an alternative HDAC inhibitor for the prodrug evaluation as well. By comparing the prodrug $IC_{50}$ values for cytotoxicity under conditions of HDAC inhibition with those values where HDACs are active we are able to provide data on the HDAC dependence of our new class of prodrugs.

Figure 23:
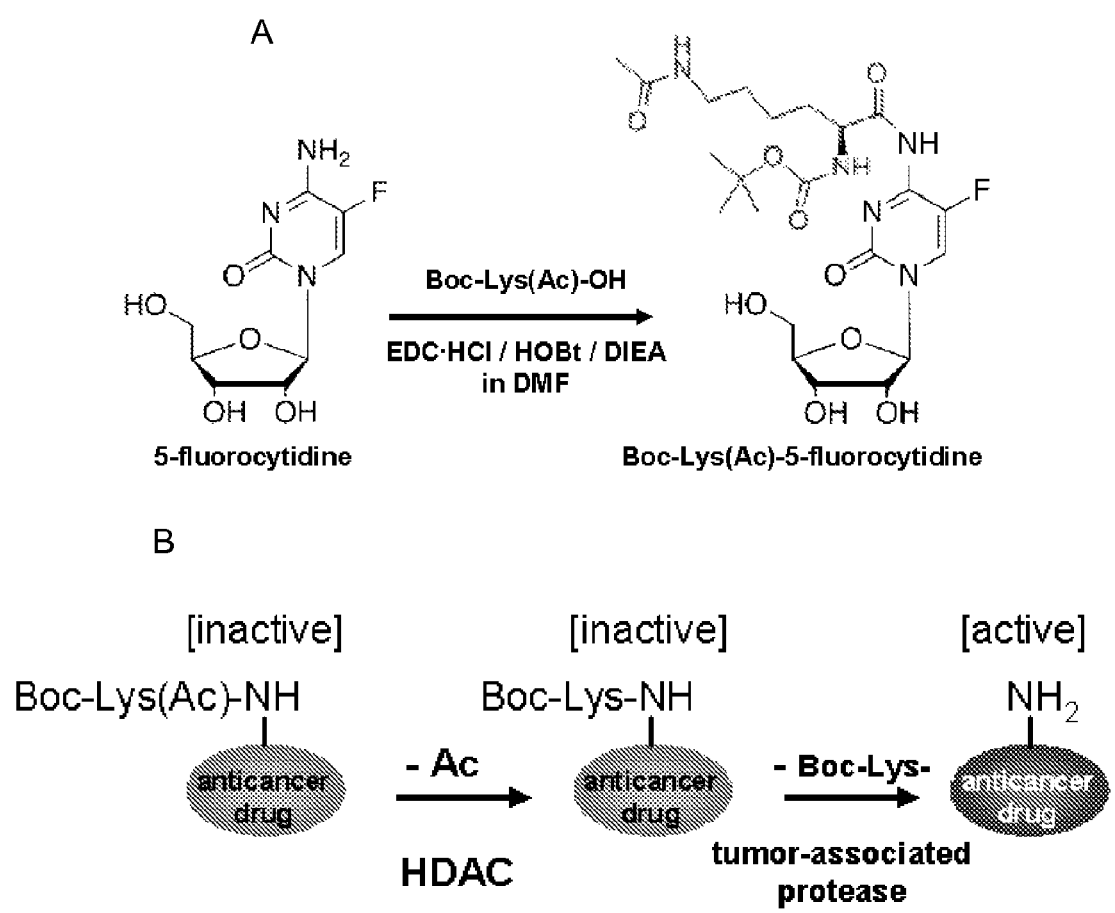
FIG. 23. A. Synthesis of Boc-Lys(Ac)-5-fluorocytidine (BKAc-5FCR). B. Mechanism of prodrug activation by HDAC and tumor-associated protease.

Although the evaluation method using AMC-conjugated peptide substrates is rapid, highly sensitive and accurate, HPLC (high-performance liquid chromatography) or TLC (thin-layer chromatography) methods are used to directly evaluate the kinetics of the activation of the substrates conjugated to the parental drugs. As already noted in FIG. 5 and as depicted in FIG. 23, the peptide sequence can influence the ability of the compounds to be recognized by HDAC and activated by the cellular proteases. Therefore different peptide sequences are used which result in compounds with more specificity. It is also possible that because different tumor cells express different proteases or different levels of tumor-associated proteases there may be some cell-specific aspects to the prodrug activation. Therefore, an expanded cohort of PDA cell lines is evaluated.

Disclosed herein is the design, synthesis and characterization of Boc-KAc-Puro, a novel prodrug targeting increased HDAC and CTSL activities in malignant tumors. Anticancer efficacy of the agent is evidenced by its ability to inhibit tumor growth in vivo without severe adverse effects. Targeting elevated HDAC and CTSL activities in malignant cancer cells has been established as a strategy for anticancer drug development. Notably, this approach is advantageous because the simple small molecule masking group could be readily applied to many other cytotoxic agents to confer selectivity that substantially improves their therapeutic index. A potent and selective anticancer agent has been developed from a mere general cytotoxic drug Puro.

Both amino acid sequence and α-amino protecting group were reported to affect kinetic parameters of peptide-based prodrug activation by cathepsin B30. Based on the similarity in substrate recognition by cathepsin B and L, it is possible to optimize the speed of drug activation for overall efficacy. Additional embodiments could be achieved by the modification of the masking group Boc-Lys(Ac). The anticancer efficacy may be improved by introducing different peptide substrates that speed up drug activation (Wegener, D. et al. 2003).

The strategy disclose herein is applied to many chemotherapeutic drugs currently used in the clinics aiming to improve their anticancer efficacy and safety. For example, amide coupling-based prodrugs of gemcitabine and cytarabine were developed by masking their amino group (Bender, D. M. et al. 2009; Cheon, E. P. et al. 2006). Thus introduction of the Boc-Lys(Ac) group to their amino group is feasible for evaluation of their improved efficacy. The observation that malignant cancer cells exhibit high levels of HDAC and CTSL activities has important implications for the potential use of their combined enzymatic activities as a selective modality for delivering therapeutics to their targets. By utilizing a small molecule masking group, a prototypic agent was specifically activated by these enzymes in cancer cells. Such agents have the potential to improve clinical outcomes as well as quality of life for the patients.

Eradication of tumor cells while minimizing damage to healthy cells is a primary goal of cancer therapy. A new prodrug strategy has been developed herein for selective cancer therapy that utilizes increased histone deacetylase (HDAC) and tumor-associated protease activities produced in malignant cancer cells. By coupling an acetylated lysine, a requirement for HDAC with an endogenous protease cathepsin L (CTSL), a masked cytotoxic agent puromycin selectively causes lethality in human cancer cell lines with high HDAC and CTSL activities. In vivo studies confirmed tumor growth inhibition due to selective drug activation in the prodrug treated mice bearing human colon cancer xenografts.

REFERENCES

Andrews, K. T. HDAC inhibitors in parasitic diseases. Immunol Cell Biol. 90, 1, 66-77 (2012).

Balajthy, Z., Aradi, J., Kiss, I. T. & Elodi, P. Synthesis and functional evaluation of a peptide derivative of 1-beta-D-arabinofuranosylcytosine. J Med Chem 35, 3344-3349 (1992).

Bhaskara, S. et al. HDAC3 is essential for the maintenance of chromatin structure and genome stability. Cancer Cell 18, 436-447 (2010).

Bolden, J. E., Peart, M. J. & Johnstone, R. W. Anticancer activities of histone deacetylase inhibitors. Nat Rev Drug Discov 5, 769-784 (2006).

Bonfils, C. et al. Evaluation of the pharmacodynamic effects of MGCD0103 from preclinical models to human using a novel HDAC enzyme assay. Clin Cancer Res 14, 3441-3449 (2008).

Bradner, J. E. et al. Chemical phylogenetics of histone deacetylases. Nat Chem Biol 6, 238-243 (2010).

Cao, Z. A. et al. CRA-026440: a potent, broad-spectrum, hydroxamic histone deacetylase inhibitor with antiproliferative and antiangiogenic activity in vitro and in vivo. Molecular cancer therapeutics 5, 1693-1701 (2006).

Carl, P. L., Chakravarty, P. K., Katzenellenbogen, J. A. & Weber, M. J. Protease-activated "prodrugs" for cancer chemotherapy. Proc Natl Acad Sci USA 77, 2224-2228 (1980).

Cheon, E. P., Hong, J. H. & Han, H. K. Enhanced cellular uptake of Ara-C via a peptidomimetic prodrug, L-valyl-ara-C in Caco-2 cells. The Journal of pharmacy and pharmacology 58, 927-932 (2006).

Choi, K. Y., Swierczewska, M., Lee, S. & Chen, X. Protease-activated drug development. Theranostics 2, 156-178 (2012).

Choudhary, C. et al. Lysine acetylation targets protein complexes and co-regulates major cellular functions. Science 325, 834-840 (2009).

Chuang, D. et al. Multiple roles of HDAC inhibition in neurodegenerative conditions. Trends Neurosci. 32, 591-601 (2009).

Collette, J. et al. Enhanced cathepsin L expression is mediated by different Ras effector pathways in fibroblasts and epithelial cells. Int J Cancer 112, 190-199 (2004).

Denhardt, D. T., Greenberg, A. H., Egan, S. E., Hamilton, R. T. & Wright, J. A. Cysteine proteinase cathepsin L expression correlates closely with the metastatic potential of H-ras-transformed murine fibroblasts. Oncogene 2, 55-59 (1987).

Dubowchik, G. M. & Firestone, R. A. Cathepsin B-sensitive dipeptide prodrugs. 1. A model study of structural requirements for efficient release of doxorubicin. Bioorg Med Chem Lett 8, 3341-3346 (1998).

Dubowchik, G. M., Mosure, K., Knipe, J. O. & Firestone, R. A. Cathepsin B-sensitive dipeptide prodrugs. 2. Models of anticancer drugs paclitaxel (Taxol), mitomycin C and doxorubicin. Bioorg Med Chem Lett 8, 3347-3352 (1998).

Fischer, A. Targeting the correct HDAC(s) to treat cognitive disorders. Trends Pharmacol Sci. 31, 12 (2010).

Gonzalez-Suarez, I. et al. A new pathway that regulates 53BP1 stability implicates cathepsin L and vitamin D in DNA repair. EMBO J 30, 3383-3396 (2011).

Goulet, B., et al. A cathepsin L isoform that is devoid of a signal peptide localizes to the nucleus in S phase and processes the CDP/Cux transcription factor. Molecular cell 14, 207-219 (2004).

Goulet, B., et al. Increased expression and activity of nuclear cathepsin L in cancer cells suggests a novel mechanism of cell transformation. Molecular cancer research: MCR 5, 899-907 (2007).

Grotsky, D. A., et al. BRCA1 loss activates cathepsin L-mediated degradation of 53BP1 in breast cancer cells. J Cell Biol 200, 187-202 (2013).

Haberland, M., Johnson, A., Mokalled, M. H., Montgomery, R. L. & Olson, E. N. Genetic dissection of histone deacetylase requirement in tumor cells. Proc Natl Acad Sci USA 106, 7751-7755 (2009).

Halili, M. A. et al. Histone Deacetylase Inhibitors In Inflammatory Disease. Curr Top Med Chem. 9, 309-319 (2009).

Heinemann, V. Gemcitabine: progress in the treatment of pancreatic cancer. Oncology 60, 8-18 (2001).

Jedeszko, C. & Sloane, B. F. Cysteine cathepsins in human cancer. Biol Chem 385, 1017-1027 (2004).

Joseph, L. J., Chang, L. C., Stamenkovich, D. & Sukhatme, V. P. Complete nucleotide and deduced amino acid sequences of human and murine preprocathepsin L. An abundant transcript induced by transformation of fibroblasts. J Clin Invest 81, 1621-1629 (1988).

Joyce, J. A. et al. Cathepsin cysteine proteases are effectors of invasive growth and angiogenesis during multistage tumorigenesis. Cancer Cell 5, 443-453 (2004).

Kano, M. R. et al. Improvement of cancer-targeting therapy, using nanocarriers for intractable solid tumors by inhibition of TGF-beta signaling. Proc Natl Acad Sci USA 104, 3460-3465 (2007).

Lankelma, J. M. et al. Cathepsin L, target in cancer treatment? Life Sci 86, 225-233 (2010).

Lee, J. H., Choy, M. L., Ngo, L., Foster, S. S. & Marks, P. A. Histone deacetylase inhibitor induces DNA damage, which normal but not transformed cells can repair. Proc Natl Acad Sci USA 107, 14639-14644 (2010).

Lee, K. K. & Workman, J. L. Histone acetyltransferase complexes: one size doesn't fit all. Nat Rev Mol Cell Biol 8, 284-295 (2007).

Manfredini, S. et al. Peptide T-araC conjugates: solid-phase synthesis and biological activity of N4-(acylpeptidyl)-araC. Bioorg Med Chem 8, 539-547 (2000).

Marks, P. A. & Xu, W. S. Histone deacetylase inhibitors: Potential in cancer therapy. J Cell Biochem 107, 600-608 (2009).

Mariadason, J. M., Velcich, A., Wilson, A. J., Augenlicht, L. H. & Gibson, P. R. Resistance to butyrate-induced cell differentiation and apoptosis during spontaneous Caco-2 cell differentiation. Gastroenterology 120, 889-899 (2001).

Mariadason, J. M. HDACs and HDAC inhibitors in colon cancer. Epigenetics 3, 28-37 (2008).

Minucci, S. & Pelicci, P. G. Histone deacetylase inhibitors and the promise of epigenetic (and more) treatments for cancer. Nat Rev Cancer 6, 38-51 (2006).

Miyamoto-Sato E, Nemoto N, Kobayashi K, Yanagawa H (2000). Specific bonding of puromycin to full-length protein at the C-terminus. Nucleic Acids Res 28: 1176-1182.

Niedergethmann, M. et al. Prognostic impact of cysteine proteases cathepsin B and cathepsin L in pancreatic adenocarcinoma. Pancreas 29, 204-211 (2004).

Oft, M., et al. TGF-beta1 and Ha-Ras collaborate in modulating the phenotypic plasticity and invasiveness of epithelial tumor cells. Genes Dev 10, 2462-2477 (1996).

O'Toole, J. M. et al. Therapeutic implications of a human neutralizing antibody to the macrophage-stimulating protein receptor tyrosine kinase (RON), a c-MET family member. Cancer Res 66, 9162-9170 (2006).

Overholser, Prewett, M. C., Hooper, A. T., Waksal, H. W. & Hicklin, D. J. Epidermal growth factor receptor blockade by antibody IMC-C225 inhibits growth of a human pancreatic carcinoma xenograft in nude mice. Cancer 89, 74-82 (2000).

Pacheco, F. J. et al. Involvement of lysosomal cathepsins in the cleavage of DNA topoisomerase I during necrotic cell death. Arthritis Rheum 52, 2133-2145 (2005).

Pestka, S., Rosenfeld, H., Harris, R. & Hintikka, H. Studies on transfer ribonucleic acid-ribosome complexes. XXI. Effect of antibiotics on peptidyl-puromycin synthesis by mammalian polyribosomes. J Biol Chem 247, 6895-6900 (1972).

Richard, J. et al. Latent Fluorophores Based on a Self-Immolative Linker Strategy and Suitable for Protease Sensing. Bioconjugate Chem 19, 1707-1718 (2008).

Schmidt, E. K., Clavarino, G., Ceppi, M. & Pierre, P. SUnSET, a nonradioactive method to monitor protein synthesis. *Nature methods* 6, 275-277 (2009).
Tian, Y., Bova, G. S. & Zhang, H. Quantitative glycoproteomic analysis of optimal cutting temperature-embedded frozen tissues identifying glycoproteins associated with aggressive prostate cancer. *Analytical chemistry* 83, 7013-7019 (2011). Vara, J. A., Portela, A., Ortin, J. & Jimenez, A. Expression in mammalian cells of a gene from Streptomyces alboniger conferring puromycin resistance. Nucleic Acids Res 14, 4617-4624 (1986).
Vecsey-Semjen, B., et al. Novel colon cancer cell lines leading to better understanding of the diversity of respective primary cancers. *Oncogene* 21, 4646-4662 (2002).
von Burstin, J. et al. Highly sensitive detection of early-stage pancreatic cancer by multimodal near-infrared molecular imaging in living mice. Int J Cancer 123, 2138-2147 (2008).
Wagner, J. M., Hackanson, B., Lubbert, M. & Jung, M. Histone deacetylase (HDAC) inhibitors in recent clinical trials for cancer therapy. Clin Epigenetics 1, 117-136 (2010).
Wegener, D., Wirsching, F., Riester, D. & Schwienhorst, A. A fluorogenic histone deacetylase assay well suited for high-throughput activity screening. Chem Biol 10, 61-68 (2003).
Weissleder, R., Tung, C. H., Mahmood, U. & Bogdanov, A., Jr. In vivo imaging of tumors with protease-activated near-infrared fluorescent probes. Nat Biotechnol 17, 375-378 (1999).
Witt, O., Deubzer, H. E., Milde, T. & Oehme, I. HDAC family: What are the cancer relevant targets? Cancer Lett 277, 8-21 (2009).
Wu, M. Z. et al. Interplay between HDAC3 and WDR5 is essential for hypoxia-induced epithelial-mesenchymal transition. Mol Cell 43, 811-822 (2011).
Yoshida, M., Kijima, M., Akita, M. & Beppu, T. Potent and specific inhibition of mammalian histone deacetylase both in vivo and in vitro by trichostatin A. J Biol Chem 265, 17174-17179 (1990).

What is claimed is:

1. A compound having the structure:

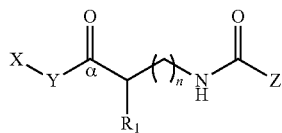

wherein
X is a chemotherapeutic agent,
  wherein the chemotherapeutic agent is a nucleoside or deoxynucleoside;
Y is a chemical linker,
  wherein Y is absent;
Z is $CH_3$ or $CF_3$;
$R_1$ is $-NR_2R_3$, $-NH-C(=O)-R_4$ or $-NH-C(=O)-OR_4$,
  wherein $R_2$, $R_3$ and $R_4$, are each, independently, $-H$, $C_{1-6}$ alkyl, $C_{2-6}$ alkenyl, $C_{2-6}$ alkynyl, heteroalkyl, cycloalkyl, heterocyclyl, aryl, alkylaryl, heteroaryl, alkylheteroaryl, an amino acid or an oligopeptide;
    wherein the amine of the amino acid or oligopeptide is substituted or unsubstituted; and
n is 4,
or a diastereomer, enantiomer or pharmaceutically acceptable salt of the compound.

2. The compound of claim 1 having the structure:

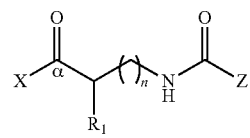

wherein
X is a chemotherapeutic agent containing at least one amine nitrogen and the amine nitrogen on the chemotherapeutic agent covalently bonds directly to carbon α,
  wherein the chemotherapeutic agent is a nucleoside or deoxynucleoside;
Z is $CH_3$ or $CF_3$;
$R_1$ is $-NR_2R_3$, $-NH-C(=O)-R_4$ or $-NH-C(=O)-OR_4$,
  wherein $R_2$, $R_3$ and $R_4$, are each, independently, $-H$, $C_{1-6}$ alkyl, $C_{2-6}$ alkenyl, $C_{2-6}$ alkynyl, heteroalkyl, cycloalkyl, heterocyclyl, aryl, alkylaryl, heteroaryl, alkylheteroaryl, an amino acid or an oligopeptide;
    wherein the amine of the amino acid or oligopeptide is substituted or unsubstituted; and
n is 4,
or a diastereomer, enantiomer or pharmaceutically acceptable salt of the compound.

3. The compound of claim 2 having the structure:

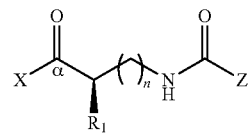

wherein
X is a chemotherapeutic agent containing at least one amine nitrogen and the amine nitrogen on the chemotherapeutic agent covalently bonds directly to carbon α,
  wherein the chemotherapeutic agent is a nucleoside or deoxynucleoside;
Z is $CH_3$ or $CF_3$;
$R_1$ is $-NR_2R_3$, $-NH-C(=O)-R_4$ or $-NH-C(=O)-OR_4$,
  wherein $R_2$, $R_3$ and $R_4$, are each, independently, $-H$, $C_{1-6}$ alkyl, $C_{2-6}$ alkenyl, $C_{2-6}$ alkynyl, heteroalkyl, cycloalkyl, heterocyclyl, aryl, alkylaryl, heteroaryl, alkylheteroaryl, an amino acid or an oligopeptide;
    wherein the amine of the amino acid or oligopeptide is substituted or unsubstituted; and
n is 4,
or a diastereomer, enantiomer or pharmaceutically acceptable salt of the compound.

4. The compound of claim 2 having the structure:

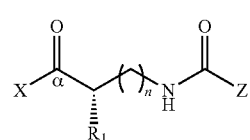

wherein
X is a chemotherapeutic agent containing at least one amine nitrogen and the amine nitrogen on the chemotherapeutic agent covalently bonds directly to carbon α, wherein the chemotherapeutic agent is a nucleoside or deoxynucleoside;

Z is CH₃ or CF₃;

R₁ is —NR₂R₃, —NH—C(=O)—R₄ or —NH—C(=O)—OR₄, wherein R₂, R₃ and R₄ are each, independently, —H, $C_{1-6}$ alkyl, $C_{2-6}$ alkenyl, $C_{2-6}$ alkynyl, heteroalkyl, cycloalkyl, heterocyclyl, aryl, alkylaryl, heteroaryl, alkylheteroaryl, an amino acid or an oligopeptide;

wherein the amine of the amino acid or oligopeptide is substituted or unsubstituted; and n is 4, or a diastereomer, enantiomer or pharmaceutically acceptable salt of the compound.

5. The compound of claim 2,
wherein R₁ is

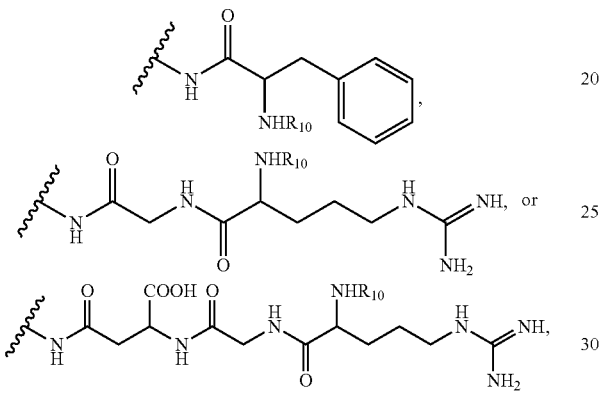

wherein R₁₀ is —H, —CH₃, Ac, —C(O)-Ot-Bu, —C(O)—OCH₂Ph, —CHO, phenyl, or benzyl, or a diastereomer, enantiomer or pharmaceutically acceptable salt of compound.

6. The compound of claim 2,
wherein X is puromycin, 5-fluorocytidine, 2'-deoxy-5-fluorocytidine, 5'-deoxy-5-fluorocytidine, gemcitabine, cytarabine, cladribine, troxacitabine, azacitidine, clofarabine, decitabine, fludarabine, fludarabine phosphate, gemcitabine hydrochloride, or nelarabine, or a diastereomer, enantiomer or pharmaceutically acceptable salt of the compound.

7. The compound of claim 2 having the structure:

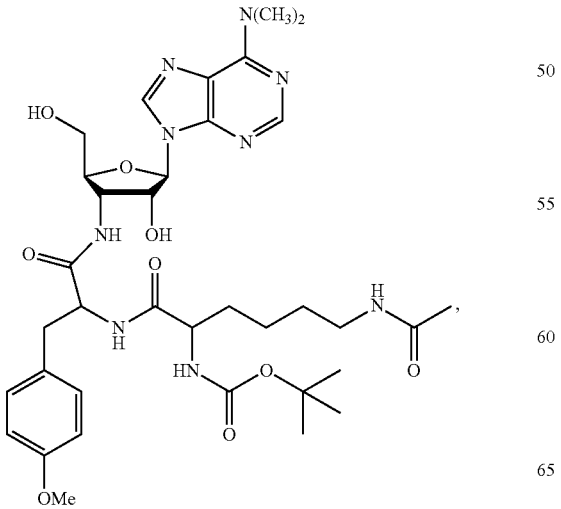

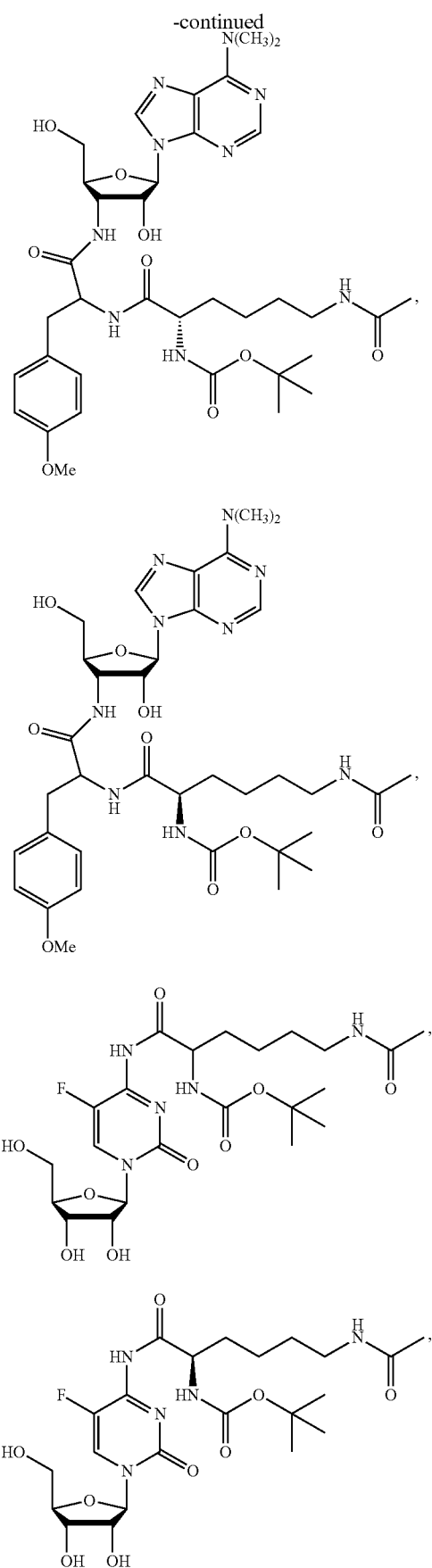

| 55 | 56 |
|---|---|
| -continued | -continued |
| 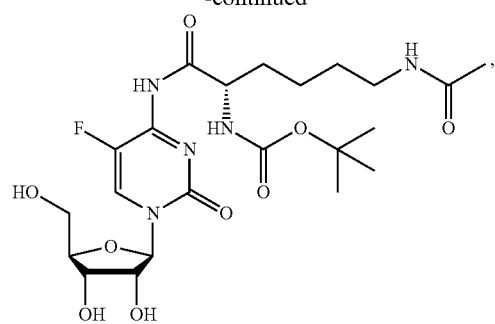 | 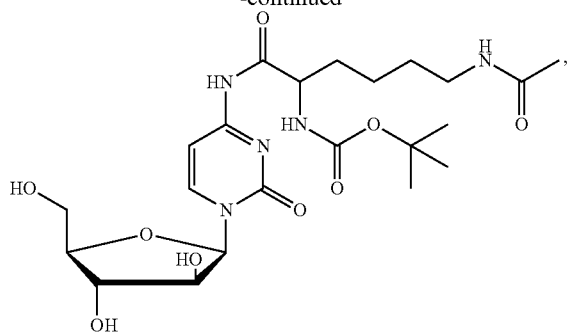 |
| 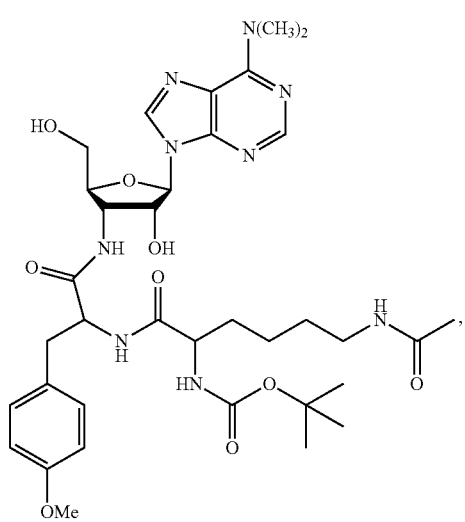 | 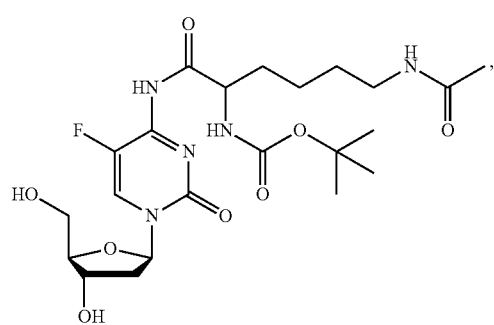 |
| | 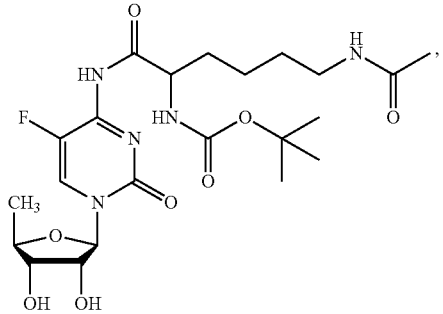 |
| 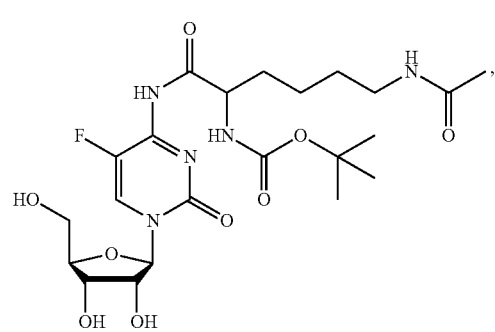 | |
| 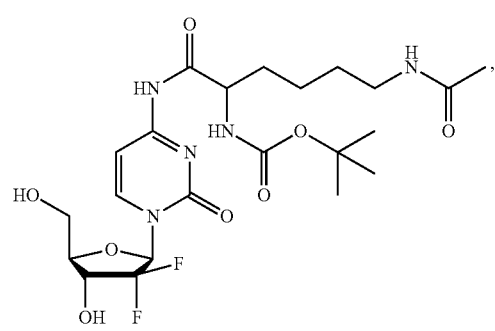 | 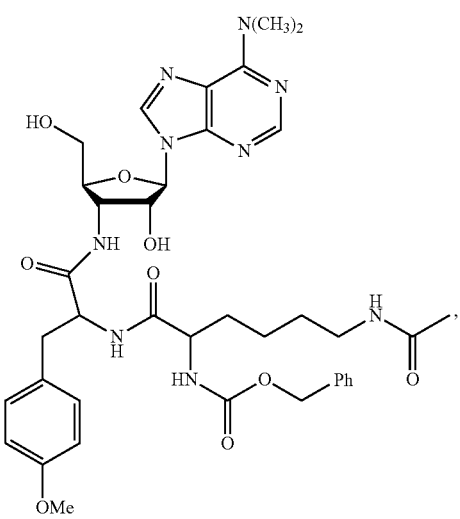 |

-continued
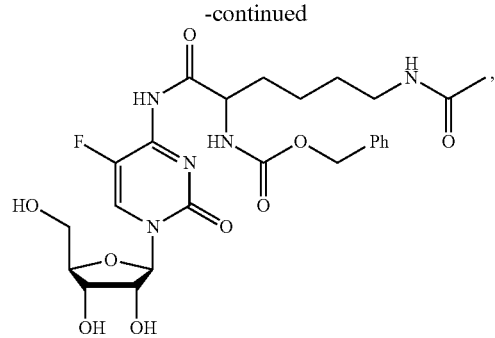
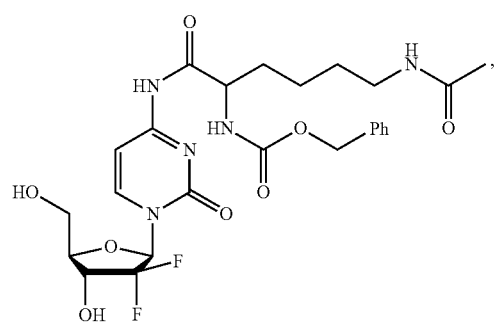
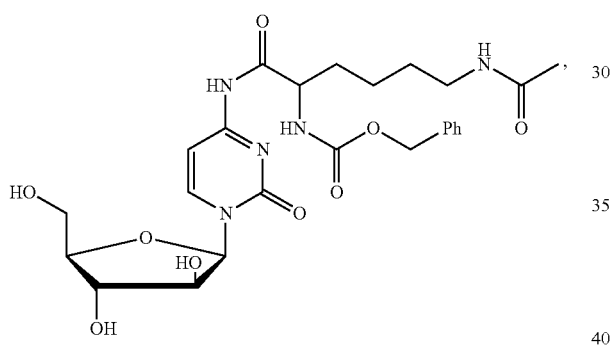
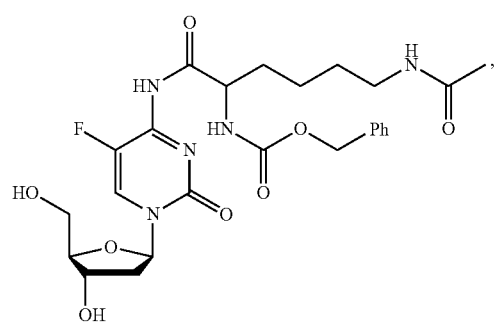
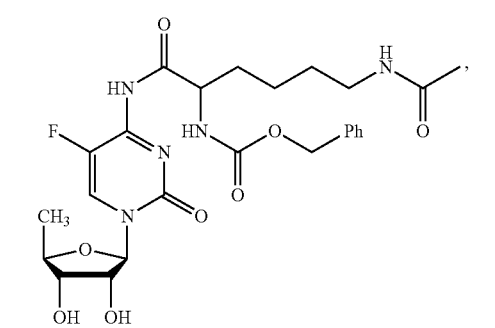
-continued
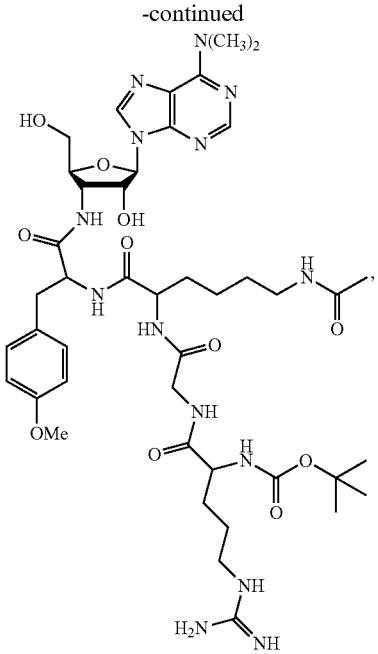
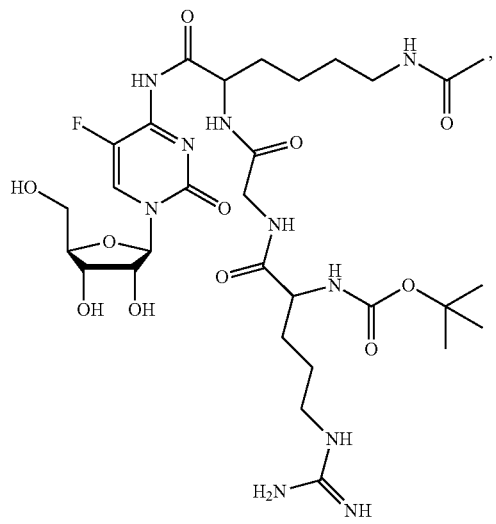

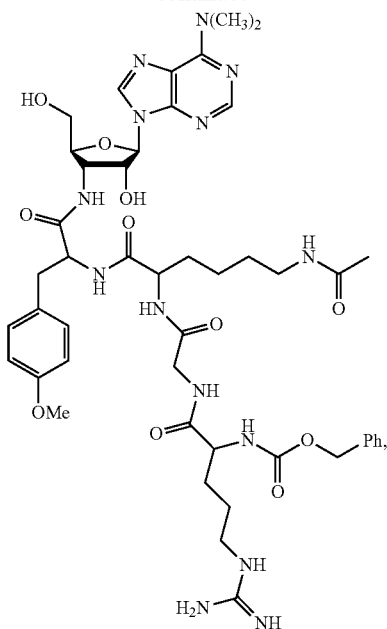

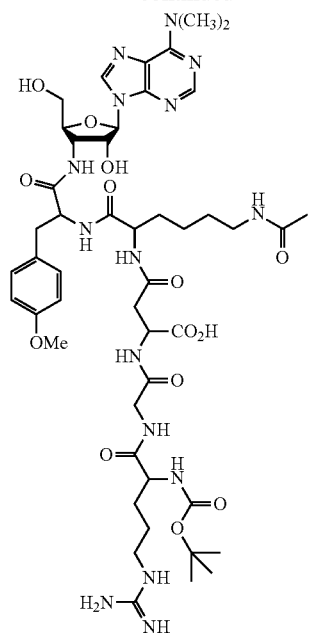

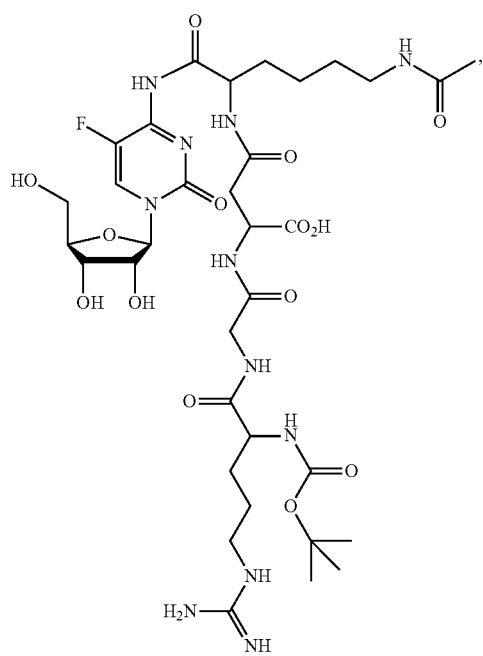

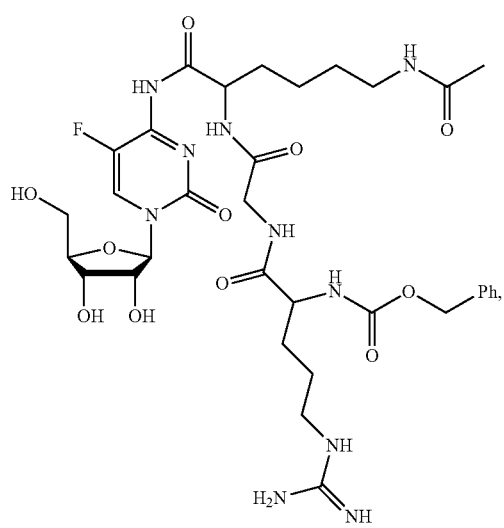

or a diastereomer, enantiomer or pharmaceutically acceptable salt of the compound.

8. A pharmaceutical composition comprising the compound of claim 1 and a pharmaceutically acceptable carrier.

9. The compound of claim 2,
wherein X is puromycin, 5-fluorocytidine, 2'-deoxy-5-fluorocytidine, 5'-deoxy-5-fluorocytidine, gemcitabine or cytarabine, or a diastereomer, enantiomer or pharmaceutically acceptable salt of the compound.

10. The compound of claim 1,
wherein $R_1$ is

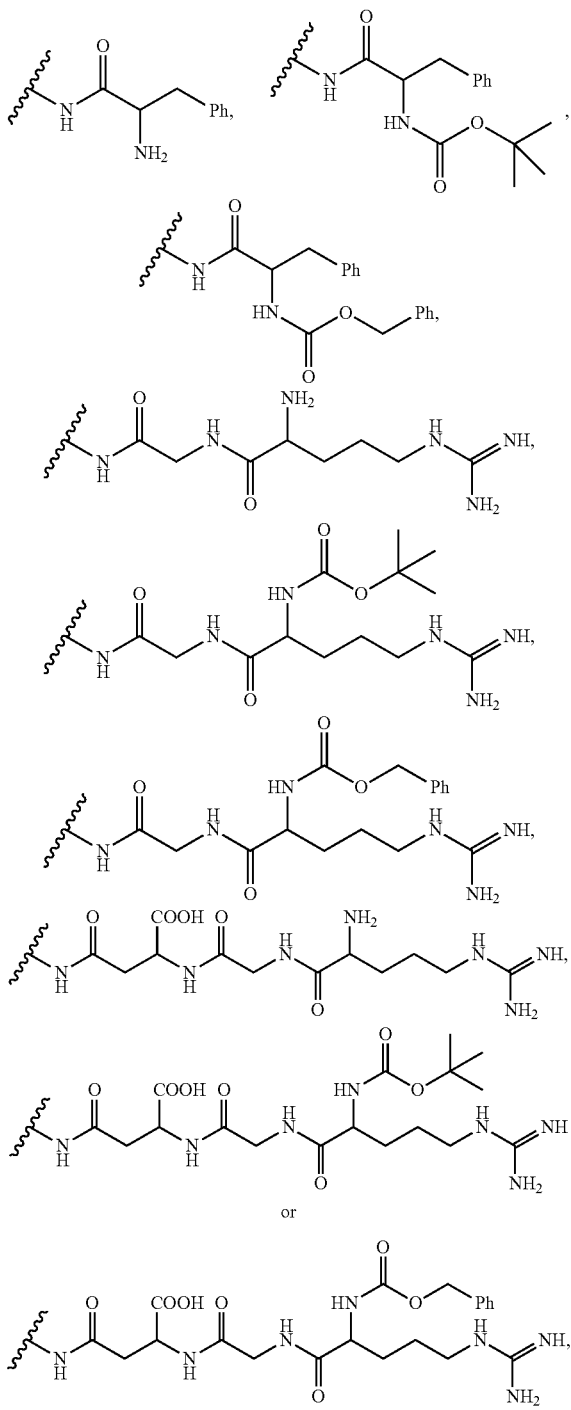

or a diastereomer, enantiomer or pharmaceutically acceptable salt of the compound.

11. The compound of claim 1,
wherein
$R_1$ is —NHBoc;
n is 4;
X is puromycin or 5-fluorocytidine; and
Z is $CH_3$,
or a diastereomer, enantiomer or pharmaceutically acceptable salt of the compound.

12. The compound of claim 1,
wherein Z is $CF_3$,
or a diastereomer, enantiomer or pharmaceutically acceptable salt of the compound.

13. A compound having the structure:

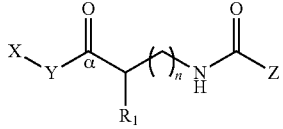

wherein
X is a chemotherapeutic agent,
 wherein the chemotherapeutic agent is a nucleoside or deoxynucleoside;
Y is a chemical linker,
 wherein Y is absent;
Z is $CH_3$ or $CF_3$;
$R_3$ is —$NR_2R_3$,
 wherein
 $R_2$ is —H; and
 $R_3$ is an amino acid or oligonucleotide,
  wherein the amino acid is bonded to the nitrogen through an amide bond, or
$R_1$ is

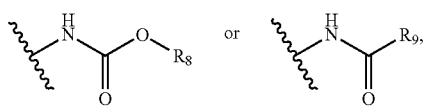

wherein $R_8$ and $R_9$ are each independently —H, —$CH_3$, t-butyl, phenyl, or benzyl; and
n is 4,
or a diastereomer, enantiomer or pharmaceutically acceptable salt of the compound.

14. The compound of claim 13 having the structure:

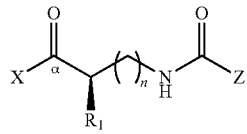

wherein
X is a chemotherapeutic agent,
 wherein the chemotherapeutic agent is a nucleoside or deoxynucleoside;
Y is a chemical linker,
 wherein Y is absent;
Z is $CH_3$ or $CF_3$;
$R_1$ is —$NR_2R_3$,
 wherein
 $R_2$ is —H; and
 $R_3$ is an amino acid or oligonucleotide,
  wherein the amino acid is bonded to the nitrogen through an amide bond, or
$R_1$ is

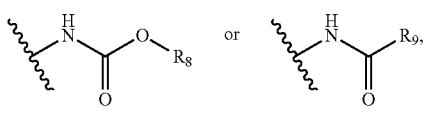

wherein $R_8$ and $R_9$ are each independently —H, —$CH_3$, t-butyl, phenyl, or benzyl; and
n is 4,
or a diastereomer, enantiomer or pharmaceutically acceptable salt of the compound.

15. The compound of claim 13 having the structure:

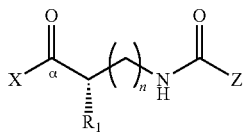

wherein
X is a chemotherapeutic agent,
  wherein the chemotherapeutic agent is a nucleoside or deoxynucleoside;
Y is a chemical linker,
  wherein Y is absent;
Z is $CH_3$ or $CF_3$;
$R_1$ is $-NR_2R_3$,
  wherein
  $R_2$ is $-H$; and
  $R_3$ is an amino acid or oligonucleotide, wherein the amino acid is bonded to the nitrogen through an amide bond, or
$R_1$ is

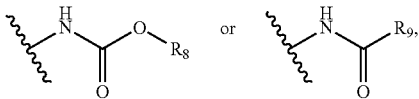

wherein $R_8$ and $R_9$ are each independently $-H$, $-CH_3$, t-butyl, phenyl, or benzyl; and
n is 4,
or a diastereomer, enantiomer or pharmaceutically acceptable salt of the compound.

16. A pharmaceutical composition comprising the compound of claim 7 and a pharmaceutically acceptable carrier.

* * * * *

UNITED STATES PATENT AND TRADEMARK OFFICE
CERTIFICATE OF CORRECTION

PATENT NO. : 9,872,919 B2
APPLICATION NO. : 14/428501
DATED : January 23, 2018
INVENTOR(S) : Nobuhide Ueki and Michael J. Hayman Page 1 of 1

It is certified that error appears in the above-identified patent and that said Letters Patent is hereby corrected as shown below:

In the Specification

In Column 1, Lines 13-15, the Federal sponsorship statement of the second paragraph should be revised to read:
This invention was made with government support under CA009176 and CA042573 awarded by the National Institutes of Health. The government has certain rights in the invention.

Signed and Sealed this
Nineteenth Day of February, 2019

Andrei Iancu
*Director of the United States Patent and Trademark Office*